US011306360B2

(12) United States Patent
Van Ooijen et al.

(10) Patent No.: US 11,306,360 B2
(45) Date of Patent: *Apr. 19, 2022

(54) ASSESSMENT OF CELLULAR SIGNALING PATHWAY ACTIVITY USING LINEAR COMBINATION(S) OF TARGET GENE EXPRESSIONS

(71) Applicant: KONINKLIJKE PHILIPS N.V., Eindhoven (NL)

(72) Inventors: Hendrik Jan Van Ooijen, Wijken Aalburg (NL); Wilhelmus Franciscus Johannes Verhaegh, Heusden gen.Asten (NL); Paul Arnold Van De Wiel, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 696 days.

This patent is subject to a terminal disclaimer.

(21) Appl. No.: 14/652,805

(22) PCT Filed: Dec. 18, 2013

(86) PCT No.: PCT/IB2013/061066
§ 371 (c)(1),
(2) Date: Jun. 17, 2015

(87) PCT Pub. No.: WO2014/102668
PCT Pub. Date: Jul. 3, 2014

(65) Prior Publication Data
US 2015/0347672 A1    Dec. 3, 2015

Related U.S. Application Data

(60) Provisional application No. 61/745,839, filed on Dec. 26, 2012.

(51) Int. Cl.
*G01N 33/48* (2006.01)
*C12Q 1/6886* (2018.01)
*G06N 5/04* (2006.01)
*G16B 5/00* (2019.01)
*G16B 25/00* (2019.01)
*G16B 25/10* (2019.01)
*G16B 40/00* (2019.01)

(52) U.S. Cl.
CPC .......... *C12Q 1/6886* (2013.01); *G06N 5/048* (2013.01); *G16B 5/00* (2019.02); *G16B 25/00* (2019.02); *G16B 25/10* (2019.02); *C12Q 2600/106* (2013.01); *C12Q 2600/118* (2013.01); *C12Q 2600/158* (2013.01); *C12Q 2600/16* (2013.01); *G16B 40/00* (2019.02)

(58) Field of Classification Search
None
See application file for complete search history.

(56) References Cited

U.S. PATENT DOCUMENTS

| 7,741,046 B2 | 6/2010 | Larsen | |
| 2008/0317745 A1* | 12/2008 | Boruchov | C07K 16/283 424/133.1 |
| 2010/0153018 A1* | 6/2010 | Bussemaker | G06F 19/18 702/19 |
| 2011/0142941 A1* | 6/2011 | Davis | A61K 9/5153 424/489 |
| 2012/0158391 A1 | 6/2012 | Vaske et al. | |
| 2014/0051746 A1* | 2/2014 | Naar | G01N 33/92 514/44 A |
| 2014/0156200 A1 | 6/2014 | Verhaegh | |

FOREIGN PATENT DOCUMENTS

| EP | 2549399 A1 | 1/2013 |
| JP | 06204354 B2 | 9/2017 |
| WO | 2004022575 A2 | 3/2004 |
| WO | 2005055113 A2 | 6/2005 |
| WO | 2007136787 A2 | 11/2007 |
| WO | 2009059994 A2 | 5/2009 |
| WO | 2011139345 A2 | 11/2011 |
| WO | 2012147016 A1 | 11/2012 |
| WO | 2013011479 A2 | 1/2013 |

OTHER PUBLICATIONS

Van Ooijen, H., et al. "Assessment of Functional Phosphatidylinositol 3-Kinase Pathway Activity in Cancer Tissue Using Forkhead Box-O Target Gene Expression in a Knowledge-Based Computational Model." The American Journal of Pathology 188.9 (2018): 1956-1972.*
Edwards, David, Lei Wang, and Peter Sørensen. "Network-enabled Gene Expression Analysis." BMC bioinformatics 13 (2012): 167.*
Yang, Ruoting et al "Core Module Network Construction for Breast Cancer Metastasis", Proceedings of the 10th World Congress on Intelligent Control and Automation, 2012.
Yu, Hui et al "Combinatorial Network of Transcriptional Regulation and MicroRNA regulation in Human Cancer", BMC Systems Biology, 2012.
Krishnan, Sasirekha et al "The Role of Signaling Pathways in the Expansion of Corneal Epithelial Cells in Serum-Free B27 Supplemented Medium", Molecular Vision, vol. 16, pp. 1169-1177, 2010.
Cheng, Chao et al "Understanding Transcriptional Regluation by Integrative Analysis of Transcription Factor Binding Data", Genome Research 2012.
Jariwala, Unnati et al "Identification of Novel Adnrogen Receptor Target Genes in Prostate Cancer", Molecular Cancer, Biomed Central , 2007.

(Continued)

Primary Examiner — Anna Skibinsky

(57) ABSTRACT

The present application mainly relates to specific methods for inferring activity of a cellular signaling pathway in tissue and/or cells of a medical subject based at least on expression levels of one or more target gene(s) of the cellular signaling pathway measured in an extracted sample of the tissue and/or cells of the medical subject, an apparatus comprising a digital compressor configured to perform such methods and a non-transitory storage medium storing instructions that are executable by a digital processing device to perform such methods.

21 Claims, 30 Drawing Sheets

Specification includes a Sequence Listing.

(56) References Cited

OTHER PUBLICATIONS

Harris, Lillianne G. et al "Hedgehog Signaling: Networking to Nurture a Promalignant Tumor Microenbironment", Molecular Cancer Research, 2011.
Bourdeau, Veronique et al "Mechanisms of Primary and Secondary Estrogen Target Gene Regulation in Breast Cancer Cells", Nucleic Acids Research, vol. 36, No. 1, 2008.
Segditsas, Stefania et al "Putative Direct and Indiect Wnt Targets Identified trhough Consistent Gene Expression Changes in APC-Mutant Intestinal Adenomas from Humans and Mice", Human Molecular Genetics, vol. 17, No. 24, 2008.
Sacedon, Rosa et al "Expression of Hedgehog Proteins in the Human Thymus", The Journal of Histochemistry & Cytochemistry, vol. 51, No. 11, 2003.
Rogers, Simon et al "Bayesian Model-based Inference of Transcription Factor Activity", BMC Bioinformatics, vol. 8, No. 2, May 2007.
Barker, N., et al.; Mining the Wnt pathway for cancer therapeutics; 2006; Nature Publishing Group: Nature Reviews/Drug Discovery; vol. 5:997-1014.
Boorsma, A., et al.; Inferring Condition-Specific Modulation of Transcription Factor Activity in Yeast through Regulon-Based Analysis of Genomewide Expression; 2008; PLoS One; 3(9)e3112-e3121.
DeSousa, F. E. M., et al.; Methylation of Cancer-Stem-Cell-Associated Wnt Target Genes Predicts Poor Prognosis in Colorectal Cancer Patients; 2011; Cell Stem Cell; 9:476-485.
Fertig, E. J., et al.; Gene expression signatures modulated by epidermal growth factor receptor activation and their relationship to cetuximab resistance in head and neck squamous cell carcinoma; 2012; BMG Genomics; 13:160-170.
Hatzis, P., et al.; Genome-Wide Pattern of TCF7L2/TCF4 Chromatin Occupancy in Colorectal Cancer Cells; 2008; Molecular and Cellular Biology; 28(8)2732-2744.
Kestler, H. A., et al.; From individual Wnt pathways towards a Wnt signalling network; 2008; Philosophical Transactions of the Royal Society B Biological Sciences; 363(1495)1333-1347.
Nusse, R.; Wnt Target Genes; May 2015; the Wnt homepage; http://www.stanford.edu/group/nusselab/cgi-bin/wnt/target_genes retrieved Jun. 16, 2015.
Ochs, M. F., et al.; Detection of Treatment-Induced Changes in Signaling Pathways in Gastrointestinal Stromal Tumors Using Transcriptomic Data; 2009; Cancer Research; 69(23)9125-9132.
Schulz, M. H., et al.; DREM 2.0: Improved reconstruction of dynamic regulatory networks from time-series expression data; 2012; BMC Systems Biology; 6(1)104-112.
Soderberg, O., et al.; Direct observation of individual endogenous protein complexes in situ by proximity ligation; 2006; Nature Methods; 3:995-1000.
Wang, S-Q., et al.; Bayesian inference based modelling for gene transcriptional dynamics by integrating multiple source of knowledge; 2012; BMC Systems Biology; 6(Suppl 1)53-65.
Robinson, Mark D. et al "A Comparison of Affymetrix Gene Expression Arrays", BMC Bioinformatics, Nov. 2017.
Cheng, Chao et al "Inferring Activity Changes of Transcription Factors by Binding Association with Sorted Expression Profiles", BMC Bioinformatics, vol. 8, No. 1, 2007, pp. 452.
Asif, H.M. Shahzad et al "TFinfer: a Tool for Propabilistic Inference of Transcription Factor Activies", Bioinformatics, vol. 26, No. 20, Aug. 2010, pp. 2635-2636.
Lee, Eunjung et al "Inferring Pathway Activity toward Precise Disease Classification", PLoS Computational Biology, vol. 4, No. 11, Nov. 2008.
Boulesteix, Anne-Laure et al "Predicting Transcription Factor Activities from Combined Analysis of Microarray and ChIP Data: A Partial Least squares approach", Theoretical Biology ABD Medical Modelling, Jun. 2005.
Wei, Zhi, "Nonparametric Pathway-based Regression MOdels for Analysis of Genomic Data" Biostatistics, vol. 8, No. 2, Apr. 2007, pp. 265-284.
Van De Stolpe, Anja et al "RNA Based Approaches to Profile Oncogenic Pathways from Low Quanity Samples to Drive Precision Oncology Strategies", Methods, Frontiers in Genetics, vol. 11, Feb. 2021.
Verhaegh, Wim et al "Knowledge-based Computational Models", Oncotarget, vol. 5, No. 14, 2014.
Verhaegh, Wim et al, "Selection of Personalized Patient Therapy through the use of Knowledge-Based Computational Models that Identify Tumor-Driving Signal Transduction Pathways", Cancer Research, Integrated Systems and Technologies: Mathematical Oncology, vol. 74, No. 11, Jun. 2014.
"Measuring Functional Activity of Signal Transduction Pathways from target Gene mRNA Levels", Philips Molecular Pathway DX, Oct. 2020.

* cited by examiner

Evidence curated list

Broad literature list

Evidence curated list

Broad literature list

ASSESSMENT OF CELLULAR SIGNALING PATHWAY ACTIVITY USING LINEAR COMBINATION(S) OF TARGET GENE EXPRESSIONS

CROSS REFERENCE TO RELATED APPLICATIONS

This application is a national filing of PCT application Serial No. PCT/IB2013/061066, filed Dec. 18, 2013 published as WO 2014/102668 A2 on Jul. 3, 2014, which claims the benefit of U.S. provisional application Ser. No. 61/745,839 filed Dec. 26, 2012, which is incorporated herein by reference.

The subject matter described herein mainly relates to bioinformatics, genomic processing arts, proteomic processing arts, and related arts.

Genomic and proteomic analyses have substantial realized and potential promise for clinical application in medical fields such as oncology, where various cancers are known to be associated with specific combinations of genomic mutations/variations and/or high or low expression levels for specific genes, which play a role in growth and evolution of cancer, e.g. cell proliferation and metastasis. For example, the Wnt signaling pathway affects regulation of cell proliferation, and is highly regulated. High Wnt pathway activity due to loss of regulation has been correlated to cancer, among which with malignant colon tumors. While not being limited to any particular theory of operation, it is believed that deregulation of the Wnt pathway in malignant colon cells leads to high Wnt pathway activity that in turn causes cell proliferation of the malignant colon cells, i.e. spread of colon cancer. On the other hand, abnormally low pathway activity might also be of interest, for example in the case of osteoporosis.

Technologies for acquiring genomic and proteomic data have become readily available in clinical settings. For example, measurements by microarrays are routinely employed to assess gene expression levels, protein levels, methylation, and so forth. Automated gene sequencing enables cost-effective identification of genetic variations in DNA and mRNA. Quantitative assessment of mRNA levels during gene sequencing holds promise as yet another clinical tool for assessing gene expression levels.

In spite of (or, perhaps, because of) these advances, clinical application of genomic and proteomic analyses faces a substantial hurdle—data overload. For example, the number of identifiable mutations in a single clinical sample can number in the hundreds of thousands or more. Most of these mutations are so called bystander mutations without specific contribution to cancer growth, and only a few do contribute to cancer growth and functional evolution, and these present the targets for effective treatment. A single microarray can generate gene expression levels for tens of thousands of genes. Processing these large quantities of data to identify clinically useful information, like for example in the application of choosing the right therapy, is difficult.

One approach is to limit the analysis to a few canonical or standardized tests, such as tests approved by the U.S. Food and Drug Administration (FDA). In such an approach, a specific indicator or combination of indicators (e.g., mutations and/or specified high or low gene expression levels) is detected in order to test "positive" for the indicated disease condition (e.g., a particular type of cancer). The canonical test is supported by clinical studies that have shown strong correlation with the disease condition or with treatment efficacy. This approach is useful only for those clinical conditions for which a canonical test has been developed, e.g. specific diagnosis of a disease, or predicting response to a drug in a specific cancer type at a specific stage, and is also rigid as it is only applicable for the canonical conditions.

Another approach is based on identification of functionally related groups of genomic or proteomic indicators. For example, the Wnt pathway comprises a cascade of proteomic reactions. Major components of this chain include (but are not limited to) binding of the Wnt signaling protein to a frizzled surface receptor of the cell which causes activation of proteins of the disheveled family of proteins which in turn impact the level of transcription agents such as β-catenin/TCF4 based protein complexes in the cell nucleus. These transcription agents, in turn, control transcription of target mRNA molecules that in turn are translated into target proteins of the Wnt pathway. Clinical studies have shown some correlations between regulatory proteins of the Wnt pathway and the activity of the Wnt pathway.

However, applying such clinical study results to the diagnosis and clinical evaluation of a specific patient is difficult due to the complexity of signaling pathways, e.g. the Wnt pathway. As a simple example, measurement of the expression level of a protein that is "upstream" in the Wnt pathway may fail to detect abnormal behavior of a protein that is "downstream" in the Wnt pathway. It is believed that the Wnt pathway includes numerous feedback mechanisms and the simplified concept of "upstream" and "downstream" may be inapplicable for a substantial portion of the Wnt pathway; more generally, abnormal behavior in one portion of the protein cascade comprising the Wnt pathway may have more or less effect on other portions of the protein cascade, and on the activity of the Wnt pathway as a whole. Still further, in some clinical studies protein expression levels for regulatory proteins of the signaling cascade are assessed by measuring mRNA expression levels of the genes that encode for the regulatory proteins. This is an indirect measurement that may not accurately assess the regulatory protein expression level, and hardly ever reflects the amount of active proteins (after a specific post-translational modification like phosphorylation).

The main problem underlying the present invention was thus to provide suitable methods and means for performing genomic and, respectively, proteomic analyses. Specific aspects of the underlying problem as well as further objections in connection with the present invention become apparent when studying the description, the examples provided herein and, in particular, when studying the attached claims.

The present invention provides new and improved methods and apparatuses as disclosed herein.

In accordance with a main aspect of the present invention, the above problem is solved by a specific method for assessing cellular signaling pathway activity using linear combination(s) of target gene expressions, namely a method comprising:

inferring activity of a cellular signaling pathway in tissue and/or cells of a medical subject based at least on expression levels (in particular on mRNA and/or protein (activity) level) of one or more target gene(s) of the cellular signaling pathway measured in an extracted sample of the tissue and/or cells of the medical subject, wherein the inferring comprises:

determining a level of a transcription factor (TF) element in the extracted sample of the tissue and/or cells of the medical subject, the TF element controlling transcription of the one or more target gene(s) of the cellular signaling pathway, the determining being based at least in part on evaluating a mathematical model relating expression levels of the one or more target gene(s) of the cellular signaling pathway to the level of the TF element, the model being based at least in part on one or more linear combination(s) of expression levels of the one or more target gene(s); and inferring the activity of the cellular signaling pathway in the tissue and/or cells of the medical subject based on the determined level of the TF element in the extracted sample of the tissue and/or cells of the medical subject; and determining whether the cellular signaling pathway is operating abnormally in the tissue and/or cells of the medical subject based on the inferred activity of the cellular signaling pathway in the tissue and/or cells of the medical subject;

wherein the inferring is performed by a digital processing device using the model of the cellular signaling pathway.

The medical subject may be a human or an animal. Moreover, the "target gene(s)" may be "direct target genes" and/or "indirect target genes" (as described herein).

Preferred is a method wherein for each of the one or more target gene(s) one or more expression level(s) measured in the extracted sample of the tissue and/or cells of the medical subject are provided, and wherein the one or more linear combination(s) comprise a linear combination of all expression levels of the one or more expression level(s) provided for the one or more target gene(s).

Also preferred is a method wherein for each of the one or more target gene(s) one or more expression level(s) measured in the extracted sample of the tissue and/or cells of the medical subject are provided, and wherein the one or more linear combination(s) comprise a linear combination including for each of the one or more target gene(s) a weighted term, each weighted term being based on only one expression level of the one or more expression level(s) provided for the respective target gene.

Also preferred is a method wherein for each of the one or more target gene(s) one or more expression level(s) measured in the extracted sample of the tissue and/or cells of the medical subject are provided, wherein the one or more linear combination(s) comprise for each of the one or more target gene(s) a first linear combination of all expression levels of the one or more expression level(s) provided for the respective target gene, and wherein the model is further based at least in part on a further linear combination including for each of the one or more target gene(s) a weighted term, each weighted term being based on the first linear combination for the respective target gene.

The cellular signaling pathway may be a Wnt pathway, an ER (Estrogen Receptor) pathway, an AR (Androgen Receptor) pathway or an HH (Hedgehog) pathway.

Thus, according to a preferred embodiment the cellular signaling pathway comprises a Wnt pathway, an ER pathway, an AR pathway or an HH pathway.

Particularly suitable target genes are described in the following text passages as well as the examples below (see e.g. Tables 1-9).

Thus, according to a preferred embodiment the target gene(s) is/are selected from the group comprising or consisting of target genes listed in Table 1 or Table 6 (for Wnt pathway), target genes listed in Table 2, Table 5 or Table 7 (for ER pathway), target genes listed in Table 3 or Table 8 (for HH pathway) and target genes listed in Table 4 or Table 9 (for AR pathway).

Particularly preferred is a method wherein the inferring comprises:
inferring activity of a Wnt pathway in the tissue and/or cells of the medical subject based at least on expression levels of one or more, preferably at least three, target gene(s) of the Wnt pathway measured in the extracted sample of the tissue and/or cells of the medical subject selected from the group comprising or consisting of: KIAA1199, AXIN2, RNF43, TBX3, TDGF1, SOX9, ASCL2, IL8, SP5, ZNRF3, KLF6, CCND1, DEFA6 and FZD7.

Further preferred is a method, wherein the inferring is further based on expression levels of at least one target gene of the Wnt pathway measured in the extracted sample of the tissue and/or cells of the medical subject selected from the group comprising or consisting of: NKD1, OAT, FAT1, LEF1, GLUL, REG1B, TCF7L2, COL18A1, BMP7, SLC1A2, ADRA2C, PPARG, DKK1, HNF1A and LECT2.

Particularly preferred is a method wherein the inferring comprises:
inferring activity of an ER pathway in the tissue and/or cells of the medical subject based at least on expression levels of one or more, preferably at least three, target gene(s) of the ER pathway measured in the extracted sample of the tissue and/or cells of the medical subject selected from the group comprising or consisting of: CDH26, SGK3, PGR, GREB1, CA12, XBP1, CELSR2, WISP2, DSCAM, ERBB2, CTSD, TFF1 and NRIP1.

Further preferred is a method, wherein the inferring is further based on expression levels of at least one target gene of the ER pathway measured in the extracted sample of the tissue and/or cells of the medical subject selected from the group comprising or consisting of: AP1B1, ATP5J, COL18A1, COX7A2L, EBAG9, ESR1, HSPB1, IGFBP4, KRT19, MYC, NDUFV3, PISD, PRDM15, PTMA, RARA, SOD1 and TRIM25.

A method wherein the inferring comprises
inferring activity of an HH pathway in the tissue and/or cells of the medical subject based at least on expression levels of one or more, preferably at least three, target gene(s) of the HH pathway measured in the extracted sample of the tissue and/or cells of the medical subject selected from the group comprising or consisting of: GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN and CTSL1, is also preferred.

Further preferred is a method, wherein the inferring is further based on expression levels of at least one target gene of the HH pathway measured in the extracted sample of the tissue and/or cells of the medical subject selected from the group comprising or consisting of: BCL2, FOXA2, FOXF1, H19, HHIP, IL1R2, JAG2, JUP, MIF, MYLK, NKX2.2, NKX2.8, PITRM1 and TOM1.

A method wherein the inferring comprises
inferring activity of an AR pathway in the tissue and/or cells of the medical subject based at least on expression levels of one or more, preferably at least three, target gene(s) of the AR pathway measured in the extracted sample of the tissue and/or cells of the medical subject selected from the group comprising or consisting of: KLK2, PMEPA1, TMPRSS2, NKX3_1, ABCC4, KLK3, FKBP5, ELL2, UGT2B15, DHCR24, PPAP2A, NDRG1, LRIG1, CREB3L4, LCP1, GUCY1A3, AR and EAF2, is also preferred.

Further preferred is a method, wherein the inferring is further based on expression levels of at least one target gene of the AR pathway measured in the extracted sample of the tissue and/or cells of the medical subject selected from the group comprising or consisting of: APP, NTS, PLAU, CDKN1A, DRG1, FGF8, IGF1, PRKACB, PTPN1, SGK1 and TACC2.

Another aspect of the present invention relates to a method (as described herein), further comprising:
recommending prescribing a drug for the medical subject that corrects for abnormal operation of the cellular signaling pathway;
wherein the recommending is performed only if the cellular signaling pathway is determined to be operating abnormally in the tissue and/or cells of the medical subject based on the inferred activity of the cellular signaling pathway.

The present invention also relates to a method (as described herein) comprising:
inferring activity of a Wnt pathway in tissue and/or cells of a medical subject based at least on expression levels of two, three or more target genes of a set of target genes of the Wnt pathway measured in an extracted sample of the tissue and/or cells of the medical subject
and/or
inferring activity of an ER pathway in tissue and/or cells of a medical subject based at least on expression levels of two, three or more target genes of a set of target genes of the ER pathway measured in an extracted sample of the tissue and/or cells of the medical subject
and/or
inferring activity of an HH pathway in tissue and/or cells of a medical subject based at least on expression levels of two, three or more target genes of a set of target genes of the HH pathway measured in an extracted sample of the tissue and/or cells of the medical subject,
and/or
inferring activity of an AR pathway in tissue and/or cells of a medical subject based at least on expression levels of two, three or more target genes of a set of target genes of the AR pathway measured in an extracted sample of the tissue and/or cells of the medical subject.

Preferably, the set of target genes of the Wnt pathway includes at least nine, preferably all target genes selected from the group comprising or consisting of: KIAA1199, AXIN2, RNF43, TBX3, TDGF1, SOX9, ASCL2, IL8, SP5, ZNRF3, KLF6, CCND1, DEFA6 and FZD7,
and/or
the set of target genes of the ER pathway includes at least nine, preferably all target genes selected from the group comprising or consisting of: CDH26, SGK3, PGR, GREB1, CA12, XBP1, CELSR2, WISP2, DSCAM, ERBB2, CTSD, TFF1 and NRIP1,
and/or
the set of target genes of the HH pathway includes at least nine, preferably all target genes selected from the group comprising or consisting of: GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN and CTSL1,
and/or
the set of target genes of the AR pathway includes at least nine, preferably all target genes selected from the group comprising or consisting of: KLK2, PMEPA1, TMPRSS2, NKX3_1, ABCC4, KLK3, FKBP5, ELL2, UGT2B15, DHCR24, PPAP2A, NDRG1, LRIG1, CREB3L4, LCP1, GUCY1A3, AR and EAF2.

A method, wherein
the set of target genes of the Wnt pathway further includes at least one target gene selected from the group comprising or consisting of: NKD1, OAT, FAT1, LEF1, GLUL, REG1B, TCF7L2, COL18A1, BMP7, SLC1A2, ADRA2C, PPARG, DKK1, HNF1A and LECT2,
and/or
the set of target genes of the ER pathway further includes at least one target gene selected from the group comprising or consisting of: AP1B1, ATP5J, COL18A1, COX7A2L, EBAG9, ESR1, HSPB1, IGFBP4, KRT19, MYC, NDUFV3, PISD, PRDM15, PTMA, RARA, SOD1 and TRIM25,
and/or
the set of target genes of the HH pathway further includes at least one target gene selected from the group comprising or consisting of: BCL2, FOXA2, FOXF1, H19, HHIP, IL1R2, JAG2, JUP, MIF, MYLK, NKX2.2, NKX2.8, PITRM1 and TOM1,
and/or
the set of target genes of the AR pathway further includes at least one target gene selected from the group comprising or consisting of: APP, NTS, PLAU, CDKN1A, DRG1, FGF8, IGF1, PRKACB, PTPN1, SGK1 and TACC2, is particularly preferred.

The sample(s) to be used in accordance with the present invention can be, e.g., a sample obtained from a breast lesion, or from a colon of a medical subject known or suspected of having colon cancer, or from a liver of a medical subject known or suspected of having liver cancer, or so forth, preferably via a biopsy procedure or other sample extraction procedure. The tissue of which a sample is extracted may also be metastatic tissue, e.g. (suspected) malignant tissue originating from the colon, breast, liver, or other organ that has spread outside of the colon, breast, liver, or other organ. The cells of which a sample is extracted may also be tumorous cells from hematologic malignancies (such as leukemia). In some cases, the cell sample may also be circulating tumor cells, that is, tumor cells that have entered the bloodstream and may be extracted as the extracted tissue sample using suitable isolation techniques. The term "extracted sample" as used herein also encompasses the case where tissue and/or cells of the medical subject have been taken from the medical subject and e.g. put on a microscope slide and where for performing the claimed method a portion of this sample is extracted, e.g. by means of Laser Capture Microdissection (LCM) or by scraping off the cells of interest from the slide.

The phrase "the cellular signaling pathway is operating abnormally" refers to the case where the "activity" of the pathway is not as expected, wherein the term "activity" may refer to the activity of the transcription factor complex in driving the target genes to expression, i.e. the speed by which the target genes are transcribed. Normal may be when it is inactive in tissue where it is expected to be inactive and active where it is expected to be active. Furthermore, there may be a certain level of activity that is considered normal, and anything higher or lower may be considered abnormal.

In accordance with another disclosed aspect, an apparatus comprises a digital processor configured to perform a method according to the invention as described herein.

In accordance with another disclosed aspect, a non-transitory storage medium stores instructions that are executable by a digital processing device to perform a method according to the invention as described herein. The non-transitory storage medium may be a computer-readable storage medium, such as a hard drive or other magnetic storage medium, an optical disk or other optical storage medium, a random access memory (RAM), read-only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, a computer program comprises program code means for causing a digital processing device to perform a method according to the invention as described herein. The digital processing device may be a handheld device (e.g., a personal data assistant or smartphone), a notebook computer, a desktop computer, a tablet computer or device, a remote network server, or so forth.

One advantage resides in a clinical decision support (CDS) system providing clinical recommendations based on a mathematical analysis of one or more cellular signaling pathway(s), for example using a mathematical model of a Wnt pathway, an ER pathway, an AR pathway and/or an HH pathway.

Another advantage resides in an improved transparency of a mathematical model that is based at least in part on one or more linear combination(s).

Another advantage resides in providing a CDS system recommending targeted treatment for loss of regulation of a cellular signaling pathway.

Another advantage resides in providing a CDS system that is designed to detect loss of regulation for a particular cellular signaling pathway, such as a Wnt pathway, an ER pathway, an AR pathway or an HH pathway, and is readily adapted to provide recommendations for different types of cancer sourced by that particular cellular signaling pathway.

The present invention as described herein can, e.g., also advantageously be used in connection with
diagnosis based on predicted (inferred) activity;
prognosis based on predicted (inferred) activity;
drug prescription based on predicted (inferred) activity;
prediction of drug efficacy based on predicted (inferred) activity;
prediction of adverse effects based on predicted (inferred) activity;
monitoring of drug efficacy;
drug development;
assay development;
pathway research;
cancer staging;
enrollment of subject in a clinical trial based on predicted (inferred) activity;
selection of subsequent test to be performed, and/or;
selection of companion diagnostics tests.

Further advantages will be apparent to those of ordinary skill in the art upon reading and understanding the attached figures, the following description and, in particular, upon reading the detailed examples provided herein below.

FIG. 1 shows an illustrative model representing part of a cellular signaling pathway. The cellular signaling pathway is symbolized by a transcription factor (TF) complex and the target genes produced as a result of the transcription complex being present in the cellular nucleus. The weights connecting the nodes of the target genes' expression and TF node, depicted here by w1, w2 and w3, indicates the strength of correlation between the transcription factor being present and the target gene's expression based on e.g. training data or expert knowledge.

FIG. 2 shows a simple model representing part of a cellular signaling pathway as in FIG. 1. Here the transcription factor complex' target gene expression nodes are replaced by direct measurements of the target genes' expression intensity levels, in this case by one probeset that is particularly highly correlated with the particular target gene, e.g. in microarray or (q)PCR experiments. The weights are based either on calculation from a training data set or based on expert knowledge.

FIG. 3 shows an illustrative two-layer model representing the experimental determination of active signaling of a pathway in more detail. For every target gene a summary level is calculated using a linear combination based on the measured intensities of its associated probesets. The calculated summary value is subsequently combined with the summary values of the other target genes of the pathway using a linear combination. The weights can be either learned from a training data set or based on expert knowledge or a combination thereof.

FIG. 4 diagrammatically shows a clinical decision support (CDS) system configured to assess one or more cellular signaling pathway(s) as disclosed herein (exemplary shown for Wnt pathway).

FIG. 5 Wnt training results using continuous expression data of GSE8671, "all probesets" mentioned in Table 1 and "black and white" weights. The left group displays the calculated linear combinations of normal samples, in which Wnt is passive, and the right group shows the calculated activity scores of adenoma samples, which are known to have an active Wnt pathway.

FIG. 6 Wnt validation results of colon cancer samples of GSE20916 (continuous data). The model was trained using continuous expression data of GSE8671, "all probesets" mentioned in Table 1 and "black and white" weights (see training results in FIG. 5). The model correctly predicts all samples to have an active or inactive Wnt pathway, except one carcinoma sample which was predicted to have a slightly passive Wnt pathway.

FIG. 7 Wnt test results in medulloblastoma samples (GSE10327, continuous data). The model was trained using continuous expression data of GSE8671, "all probesets" mentioned in Table 1 and "black and white" weights (see training results in FIG. 5). The model is able to predict all Wnt positive medulloblastoma samples (last group) to have a slightly active Wnt pathway. All Wnt positive samples have a relatively low positive Wnt activity score compared to all Wnt negative samples. This can be an indication that in medulloblastoma samples the threshold should be lower than in colon samples, possibly due to tissue-specific differences in gene expression.

FIG. 8 HH training results using continuous expression data of GSE7553, the "two-layer" model with gene summaries using all the probesets mentioned in Table 3 and "log odds" weights. The 1st and 5th group of samples (from the left) have been used as positive and negative training samples, respectively.

FIG. 9 HH test results using continuous expression data of medulloblastoma samples (GSE10327). The model was trained using continuous expression data of GSE7553, the "two-layer" model, all the probesets mentioned in Table 3 and "log odds" weights (see training results in FIG. 8). Approximately half of the samples in the HH positive group (indicated by shh) are predicted by the model to have an active pathway.

FIG. 10 ER training results using continuous expression data of GSE8597, the "most discriminant probesets" (underlined probesets in Table 2) and "log odds" weights. The 3rd and 4th group of samples (from the left) have been used as positive and negative training samples, respectively.

FIG. 11 ER test results using continuous data of breast cancer samples (GSE12276). The model is trained using continuous expression data of GSE8597, the "most discriminative probesets" (underlined probesets in Table 2) and "log odds" weights (see training results in FIG. 10). Approximately 25% of the ER+ samples are predicted to have an active ER pathway which can partly be explained by the relative high ineffective hormonal treatment in these types of breast cancers of 50-60%. The ER pathway is predicted correctly to have a passive ER pathway in the ER− samples.

FIG. 12 ER pathway prediction in stimulation response data of MCF7 cells treated with ER stimulating agent (E2) or control for several treatment intervals (GSE11352, continuous data). The model is trained using continuous expression data of GSE8597, the "most discriminative probesets" (underlined probesets in Table 2) and "log odds" weights (see training results in FIG. 10). The ER pathway activity is properly predicted to increase for longer exposure times to ER stimulating agent and decrease in case of prolonged starvation in the control.

FIG. 13 AR training results using fuzzy transformed expression data of GSE7868, "all probesets" as mentioned in Table 4 and "black and white" weights. The 1st and 2nd group of samples (from the left) has been used as negative and positive training samples, respectively.

FIG. 14 AR test results of cell lines treated with different regimes of AR stimulation or not (GSE7708, fuzzy transformed). The model was trained using fuzzy transformed expression data of GSE7868, "all probesets" as mentioned in Table 4 and "black and white" weights (see training results shown in FIG. 13). The model correctly predicts the cell lines that are treated with an AR stimulating agent to have an active AR pathway and the others not treated with an AR stimulating agent (fourth group of samples) or treated with stimulating agent and anti-androgen drug (first group of samples) to have a passive AR pathway.

FIG. 15 AR test results of prostate samples (GSE17951, fuzzy transformed). The model was trained using fuzzy transformed expression data of GSE7868, "all probesets" as mentioned in Table 4 and "black and white" weights (see training results shown in FIG. 13). The model predicts a relative high frequency of active AR pathways in both the biopsy as well as the surgically removed tumor and a relative low number AR activity in the control samples.

FIG. 16 Kaplan-Meier survival curves of patients from the GSE12276 data set grouped according to pathway activity. The survival curves indicate that patients with an active ER pathway have a better prognosis compared to patients having a passive ER pathway, which is in agreement with clinical practice. In addition patients predicted to have an active HH or Wnt pathway are depicted to have a worse prognosis, which is also supported by scientific literature.

FIG. 17 ER validation results of a stimulation experiment with MCF7 cells (GSE9253, continuous data). The (pseudo-)linear model was trained using continuous expression data of GSE8597, the "most discriminative probesets" (underlined probesets in Table 2) and "log odds" weights (see training results in FIG. 10). It is clear from the MCF7 cells stimulated with E2, ER stimulating agent, that the defined threshold was set too high. The reason for this discrepancy could be a different stimulation regime (i.e. higher E2 concentration, but shorter stimulation time, etc.). Nevertheless, the difference of the calculated ER activity scores of the stimulated and non-stimulated cells is evident. The negative control properly predicts the ER pathway to be inactive.

Figure 20:
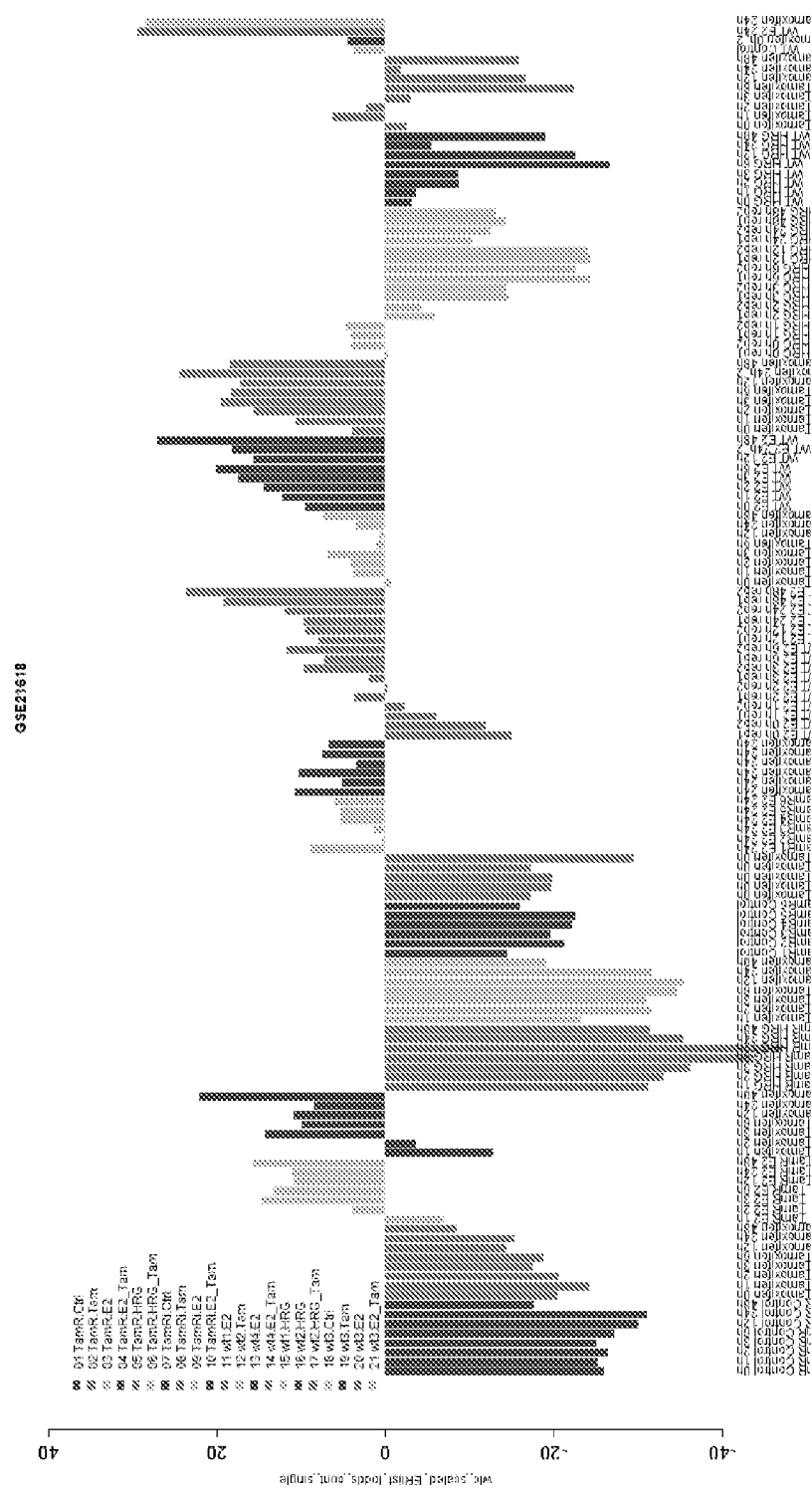

FIG. 20 shows a predicted ER pathway activity in MCF7 and Tamoxifen resistant MCF7 cell lines from GSE21618. The ER (pseudo-)linear model was trained using continuous expression data of GSE8597, the "most discriminative probesets" (underlined probesets in Table 2) and "log odds" weights (see training results in FIG. 10). Different stimulation regimes were applied, denoted in the different groups of samples, and the expression of mRNA was measured by microarray at 0, 1, 2, 3, 6, 12, 24, 48 hours, denoted by the consecutive samples in the groups.

Figure 21:
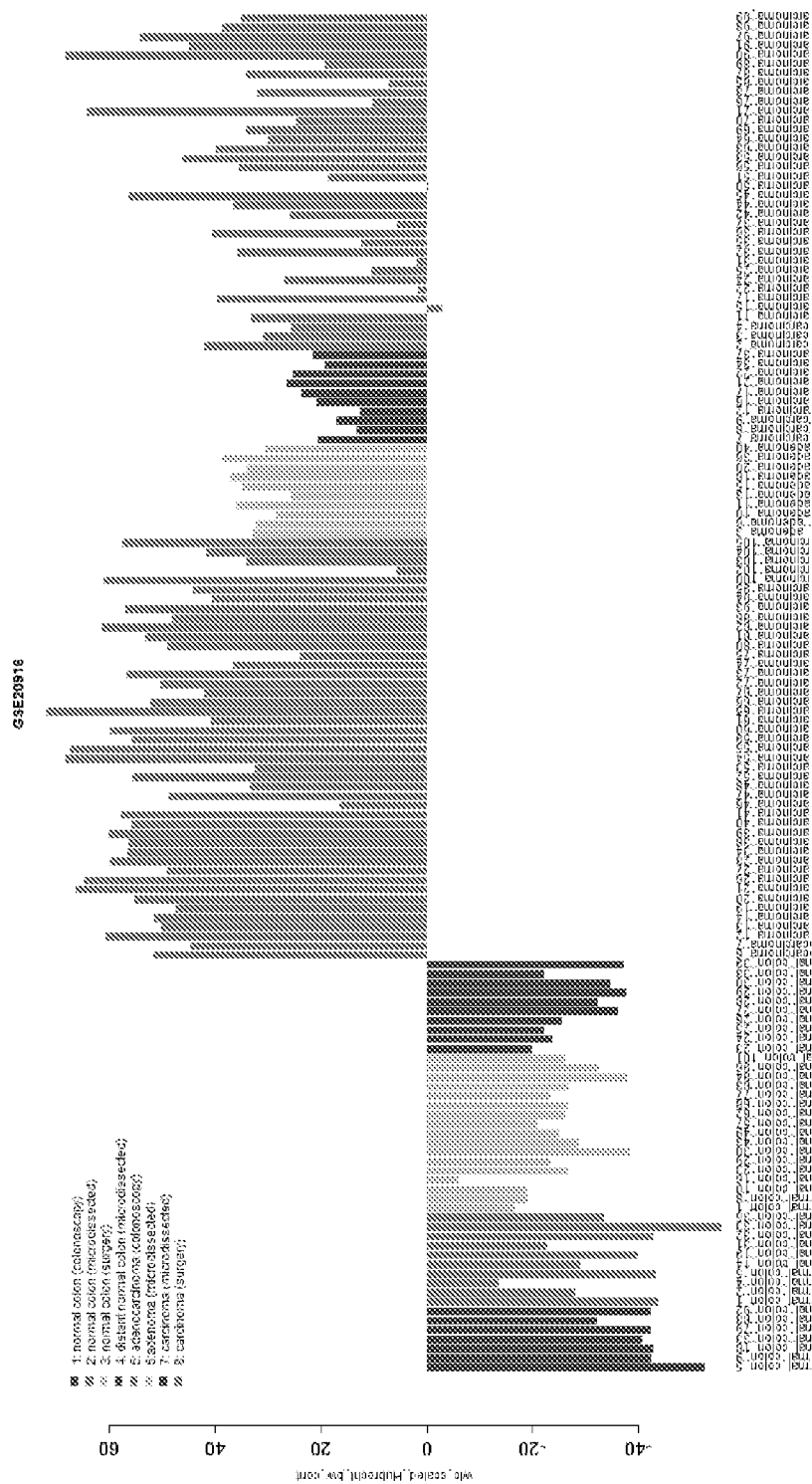
Figure 21:
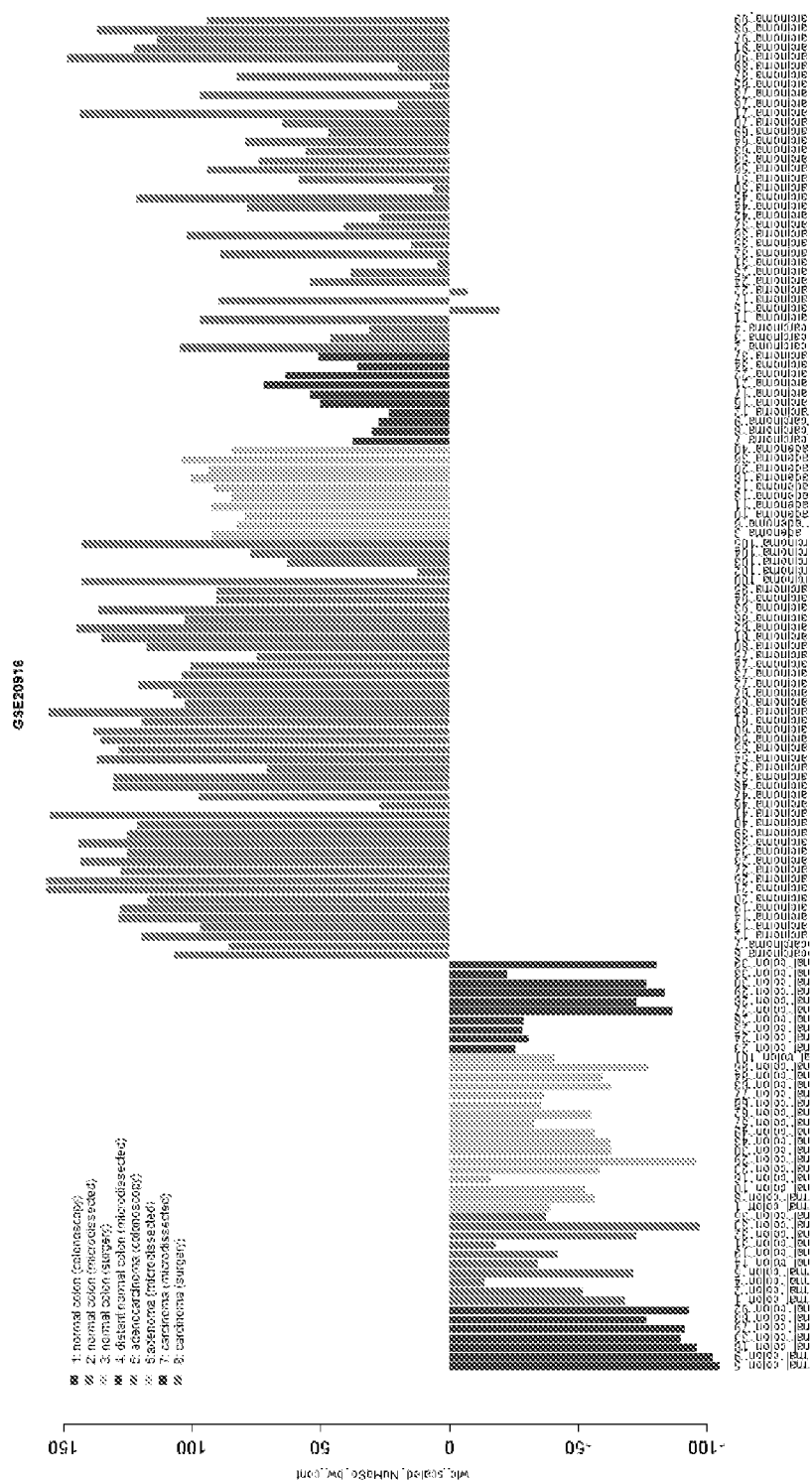

FIG. 21 shows a predicted Wnt pathway activity score calculated using a (pseudo-) linear model using the target genes of the evidence curated list compared (Table 1) to the target genes of the broad literature list (Table 11) and weights calculated using the "black and weight"-method as described herein in a data set of colon samples (GSE20916).

Figure 22:
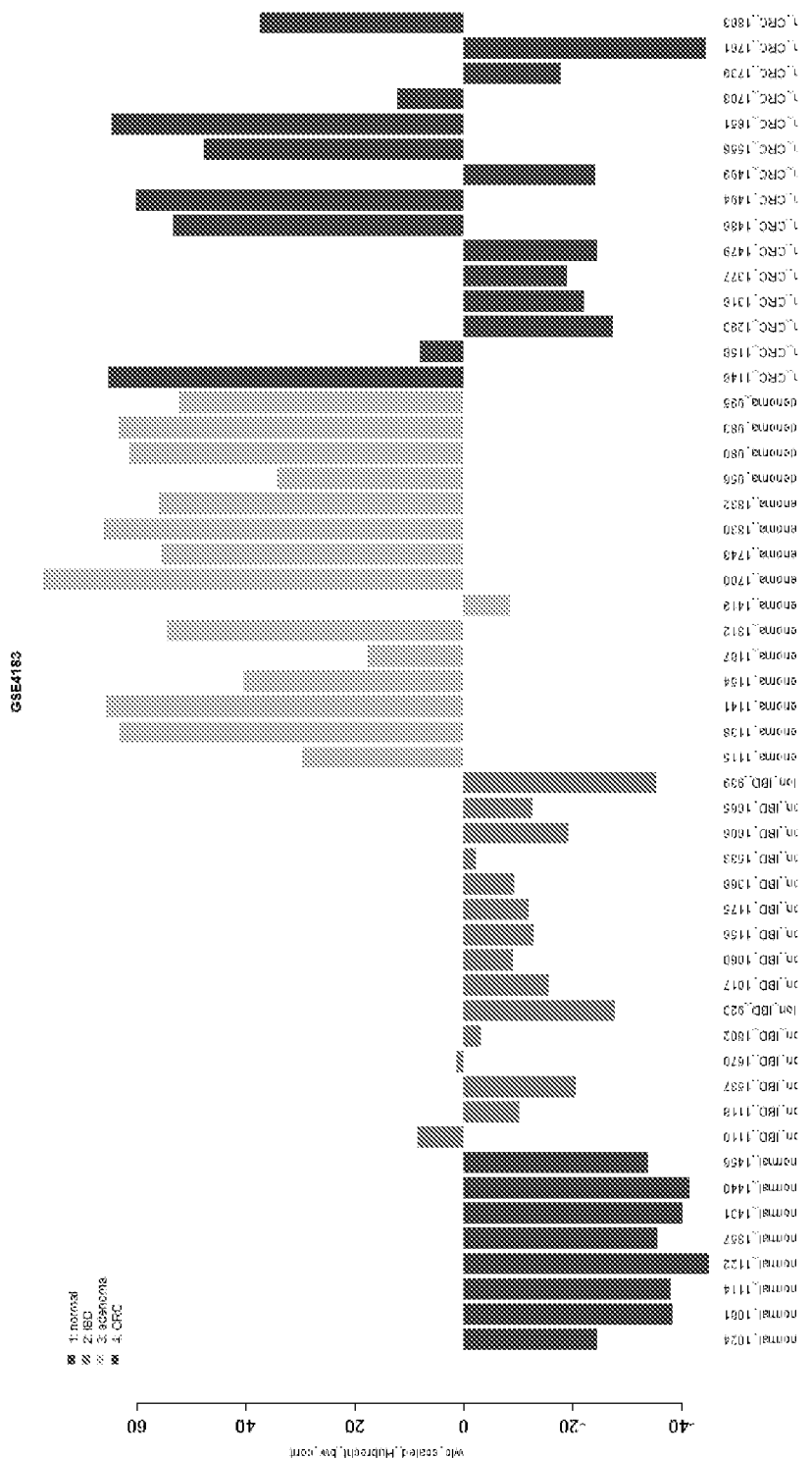
Figure 22:
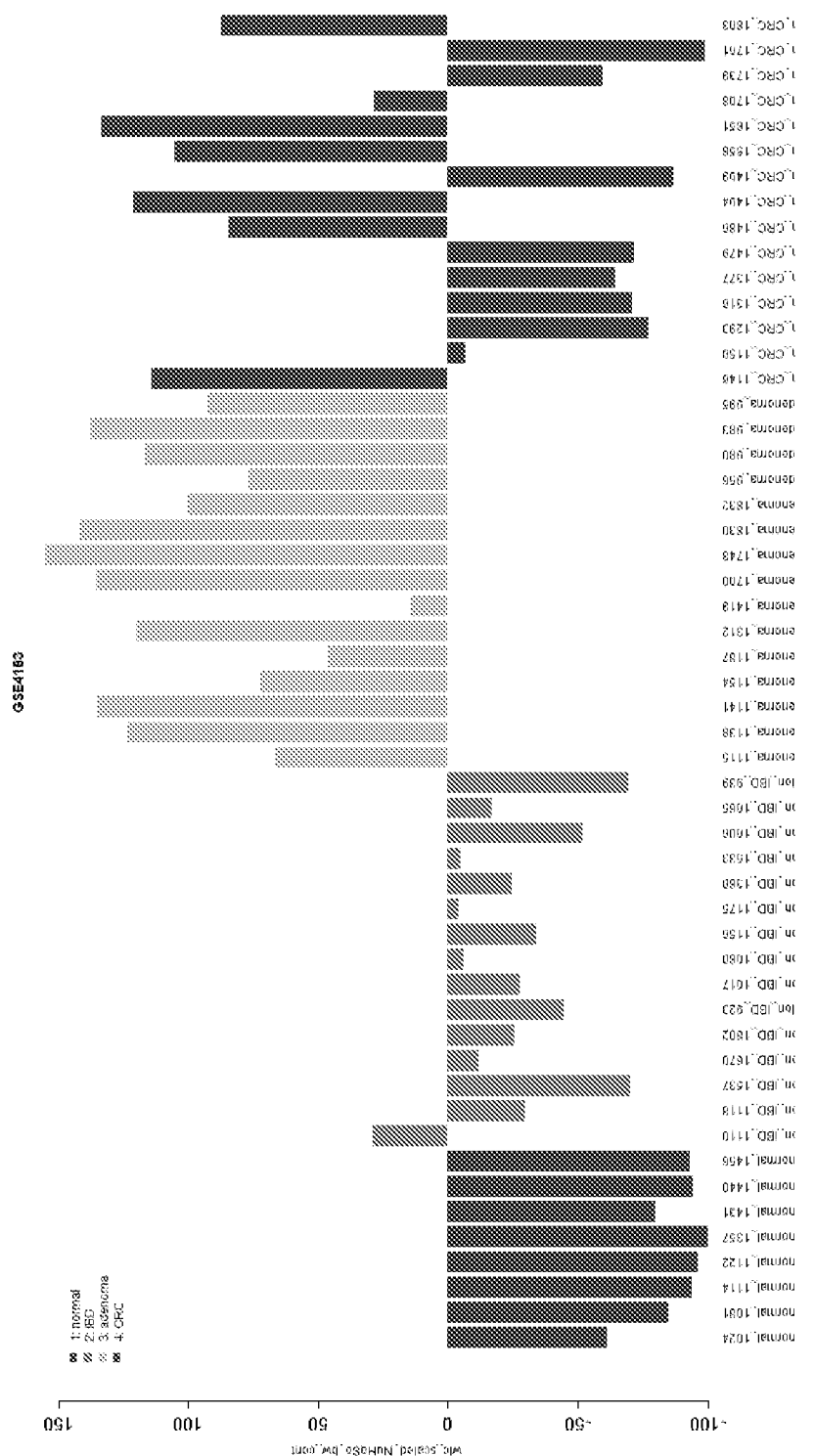

FIG. 22 shows a predicted Wnt pathway activity score calculated using a (pseudo-) linear model using the target genes of the evidence curated list compared (Table 1) to the target genes of the broad literature list (Table 11) and weights calculated using the "black and weight"-method as described herein in a data set of colon samples (GSE4183).

Figure 23:
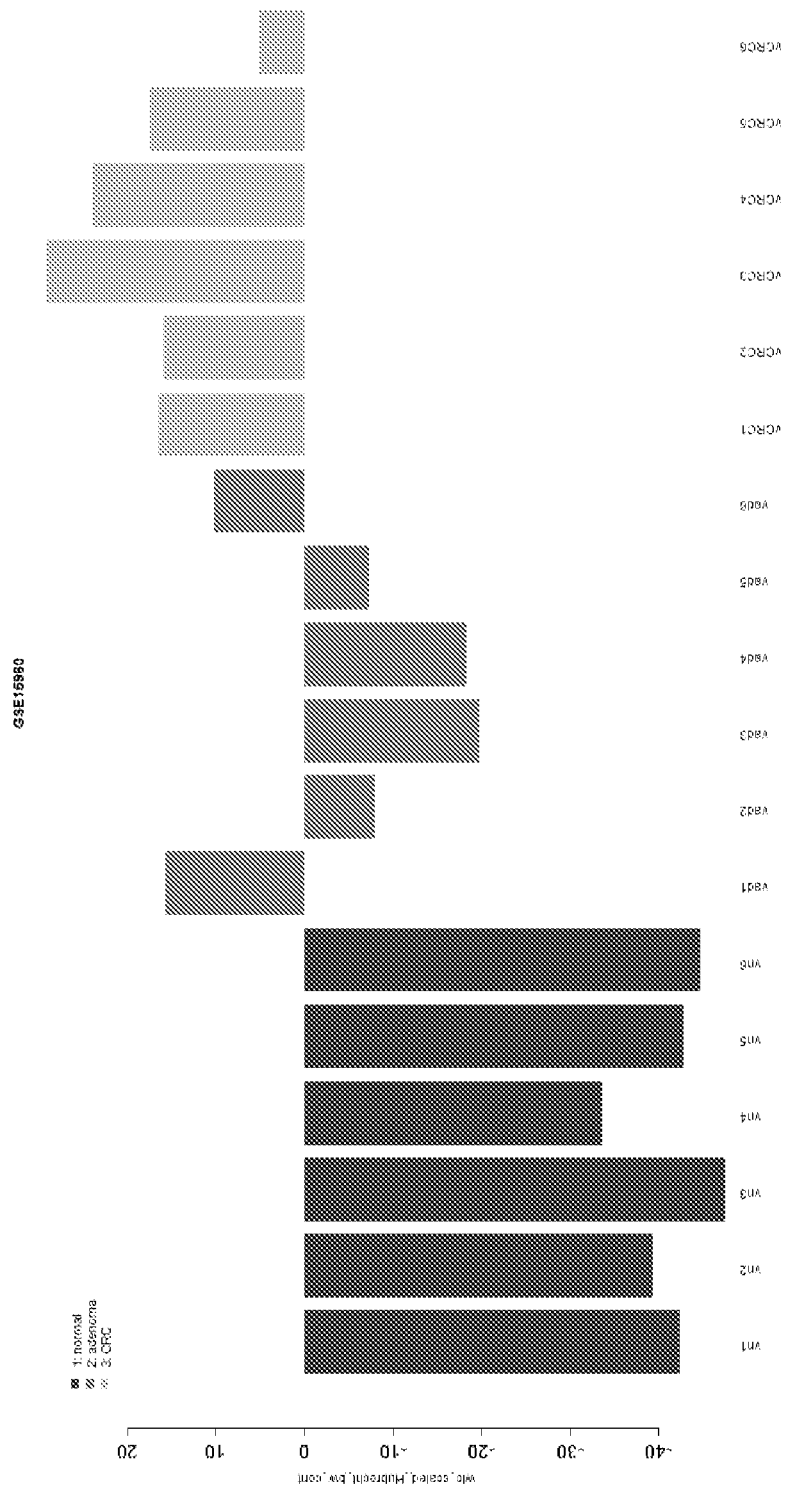
Figure 23:
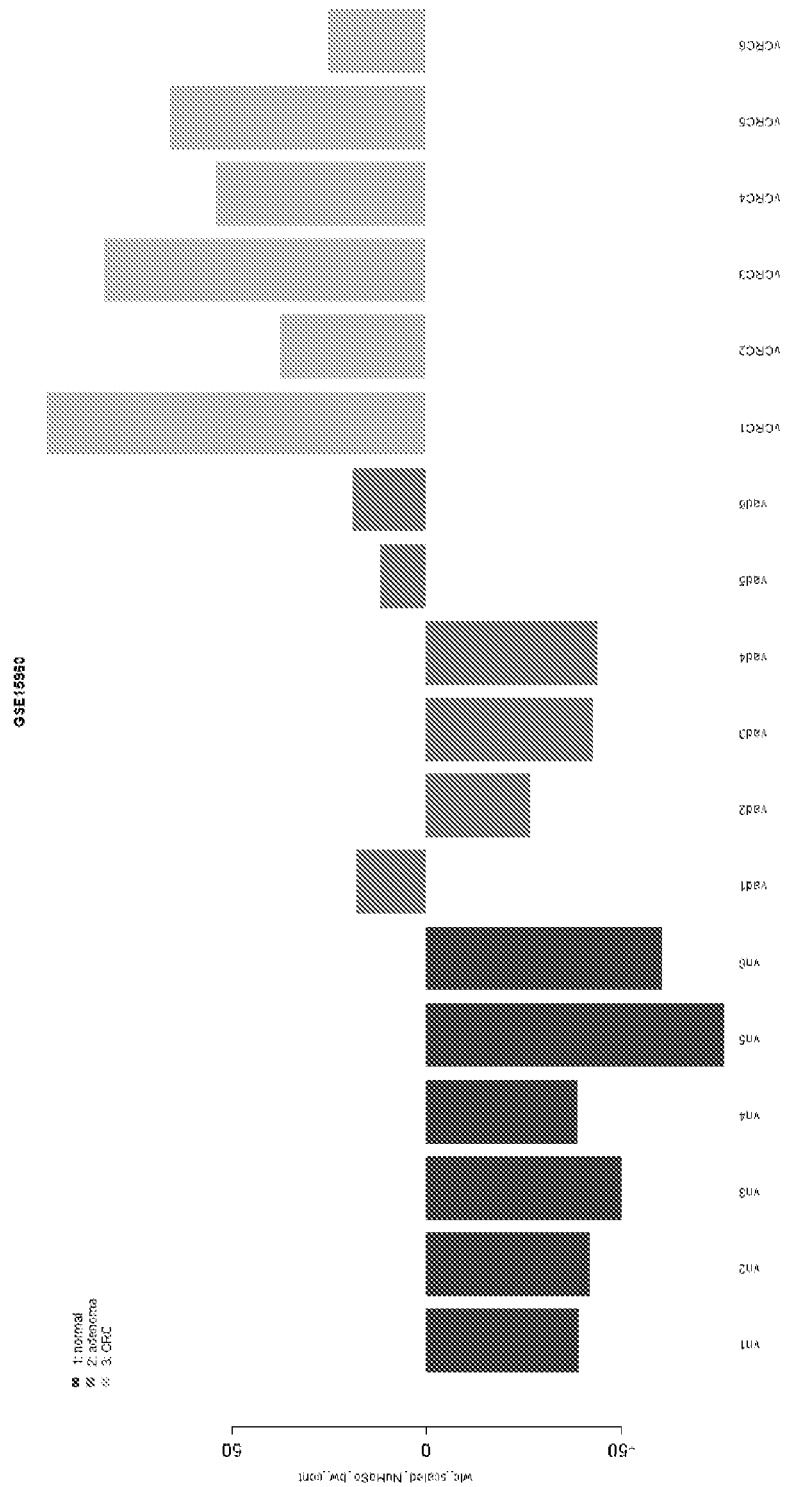

FIG. 23 shows a predicted Wnt pathway activity score calculated using a (pseudo-) linear model using the target genes of the evidence curated list compared (Table 1) to the target genes of the broad literature list (Table 11) and weights calculated using the "black and weight"-method as described herein in a data set of colon samples (GSE15960).

Figure 24:
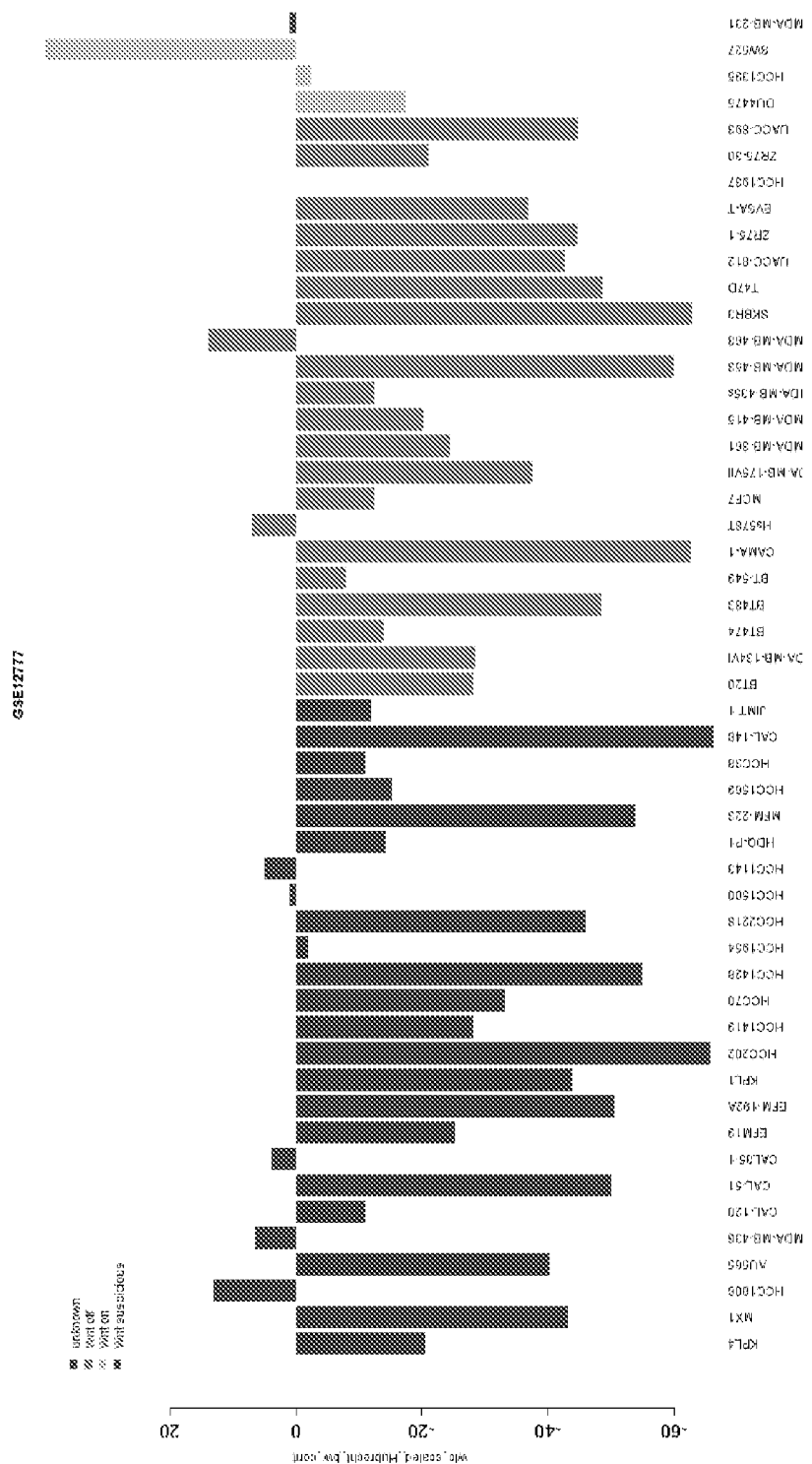
Figure 24:
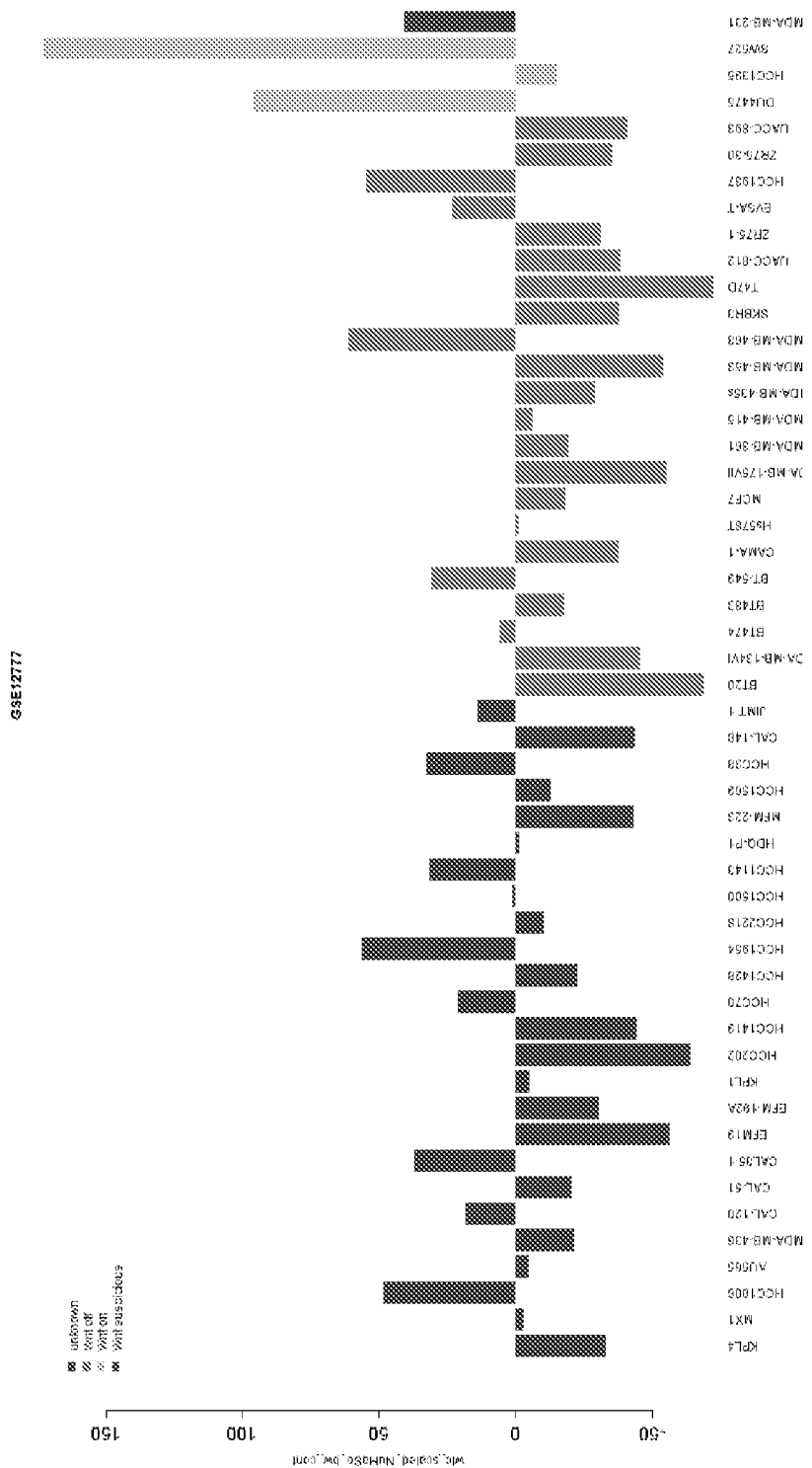

FIG. 24 shows a predicted Wnt pathway activity score calculated using a (pseudo-) linear model using the target genes of the evidence curated list compared (Table 1) to the target genes of the broad literature list (Table 11) and weights calculated using the "black and weight"-method as described herein in a data set of breast cancer samples (GSE12777).

Figure 25:
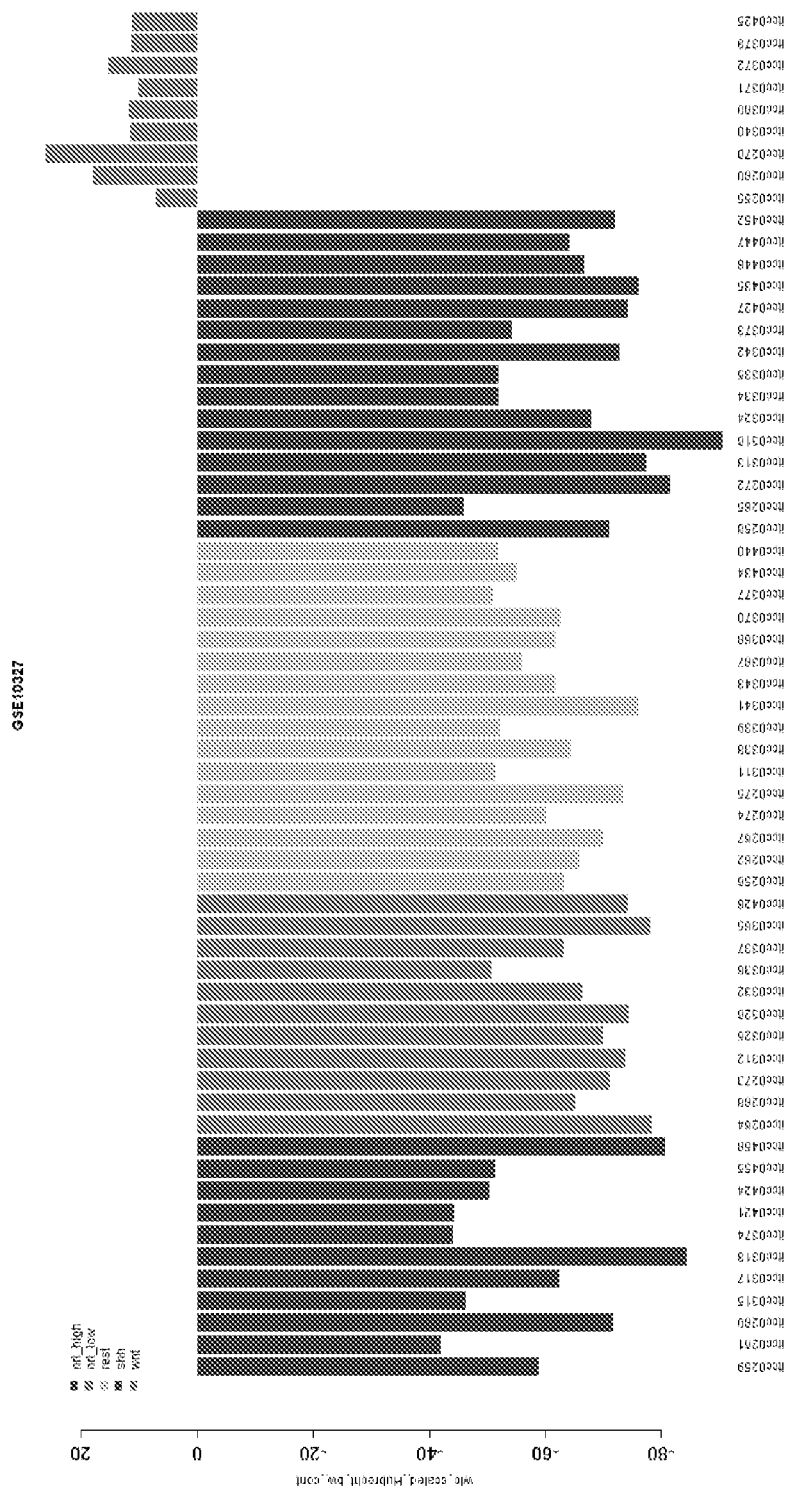
Figure 25:
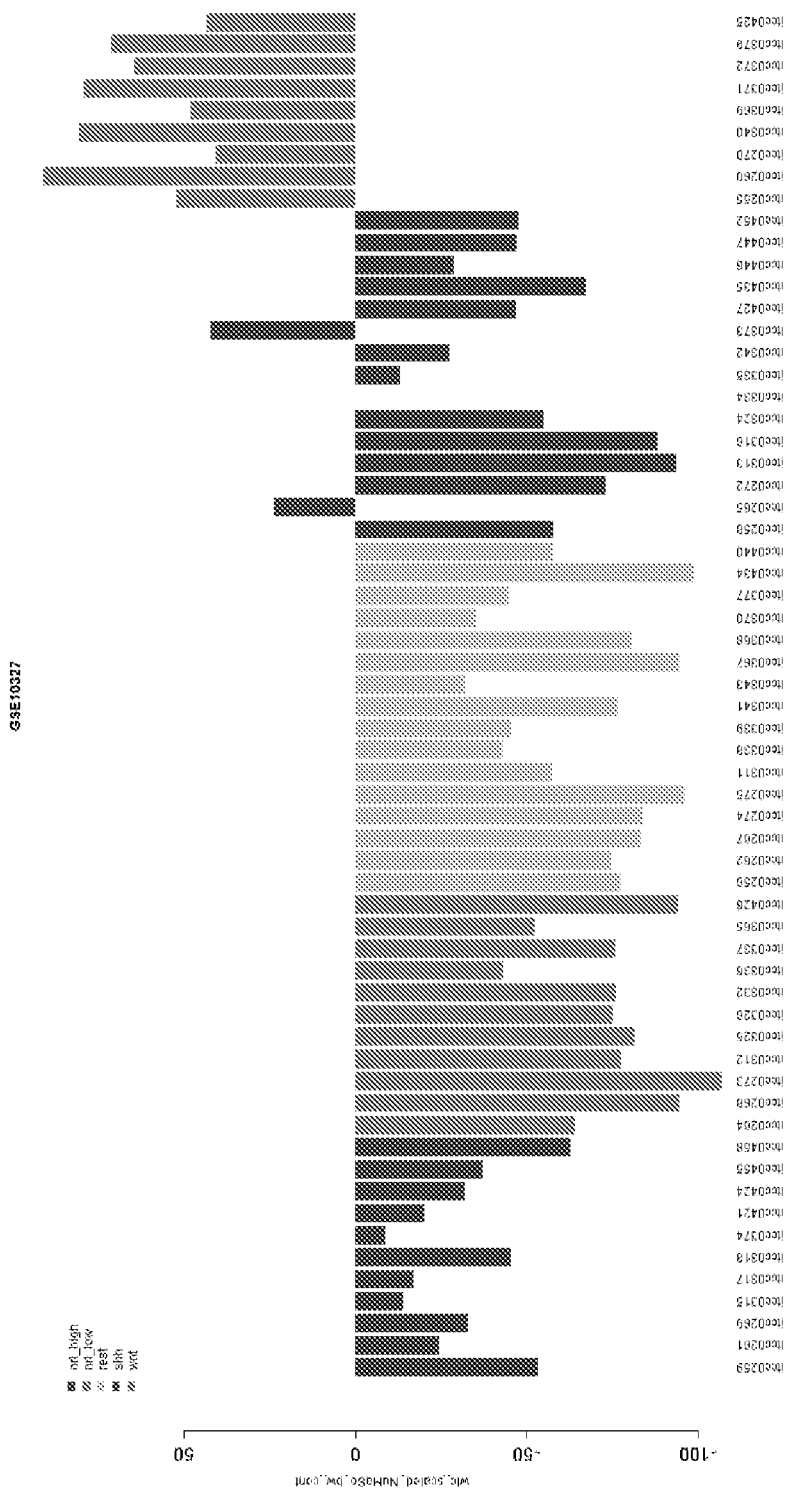

FIG. 25 shows a predicted Wnt pathway activity score calculated using a (pseudo-) linear model using the target genes of the evidence curated list compared (Table 1) to the target genes of the broad literature list (Table 11) and weights calculated using the "black and weight"-method as described herein in a data set of medulloblastoma samples (GSE10327).

The following examples merely illustrate particularly preferred methods and selected aspects in connection therewith. The teaching provided therein may be used for constructing several tests and/or kits, e.g. to detect, predict and/or diagnose the abnormal activity of one or more cellular signaling pathways. Furthermore, upon using methods as described herein drug prescription can advantageously be guided, drug prediction and monitoring of drug efficacy (and/or adverse effects) can be made, drug resistance can be predicted and monitored, e.g. to select subsequent test(s) to be performed (like a companion diagnostic test). The following examples are not to be construed as limiting the scope of the present invention.

EXAMPLE 1

Mathematical Model Construction

As disclosed herein, by constructing a mathematical model (e.g., the illustrative "two-layer" model shown in FIG. 3) incorporating relationships between expression levels of one or more target gene(s) of a cellular signaling pathway and the level of a transcription factor (TF) element, the TF element controlling transcription of the one ore more target gene(s) of the cellular signaling pathway, the model being based at least in part on one or more linear combination(s) of expression levels of the one or more target gene(s), such a model can be used to determine the activity of the cellular signaling pathway in a way that is easy to comprehend and interpret.

The expression levels of the target genes are preferably measurements of the level of mRNA, which can be the result of e.g. (RT)-PCR and microarray techniques using probes associated with the target genes' mRNA sequences, and of RNA-sequencing. In another embodiment the expression levels of the target genes can be measured by protein levels, e.g. the concentrations of the proteins encoded by the target genes.

The aforementioned expression levels can optionally be converted in many ways that might or might not suit the application better. Here, we have used four different transformations of the expression levels, in this case microarray-based mRNA levels:

"continuous data", i.e. expression levels as obtained after preprocessing of microarrays using well known algorithms such as MAS5.0 and fRMA, "z-score", i.e. continuous expression levels scaled such that the average across all samples is 0 and the standard deviation is 1, "discrete", i.e. every expression above a certain threshold is set to 1 and below it to 0 (e.g. the threshold for a probeset may be chosen as the median of its value in a set of a number of positive and the same number of negative clinical samples), "fuzzy", i.e. the continuous expression levels are converted to values between 0 and 1 using a sigmoid function of the following format: $1/(1+\exp((thr-expr)/se))$, with expr being the continuous expression levels, thr being the threshold as mentioned before and se being a softening parameter influencing the difference between 0 and 1.

Figure 1:
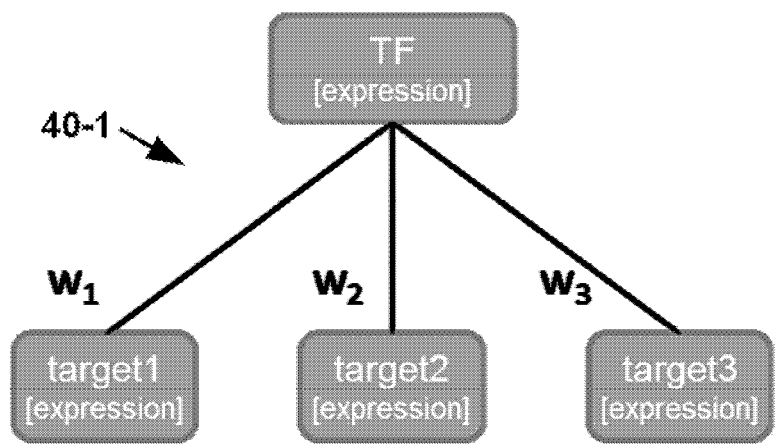

FIG. 1 shows an illustrative mathematical model representing (part of) a cellular signaling pathway. The cellular signaling pathway is symbolized by a transcription factor (TF) element and the target genes produced as a result of the transcription element being present in the cellular nucleus. The weights connecting the nodes of the target genes' expression and the TF node, depicted here by w1, w2 and w3, indicate the strength of correlation between the transcription factor being present and the target gene's expression based on e.g. training data or expert knowledge.

Figure 2:
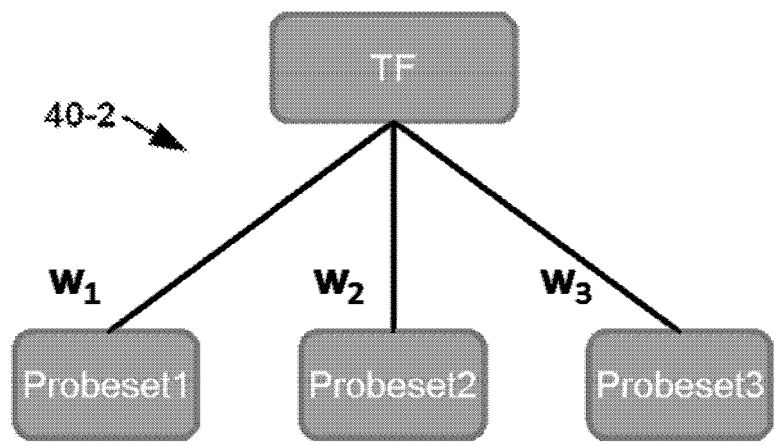

One of the simplest models that can be constructed is shown in FIG. 2. Here the transcription factor element's target gene expression nodes are replaced by direct measurements of the target genes' expression intensity levels, in this case by one probeset that is particularly highly correlated with the particular target gene, e.g. in microarray or (q)PCR experiments. The weights are based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is preferred because it is particularly simple. One preferred way of selecting the one expression level that is used for a particular target gene is to use the expression level from the probeset that is able to separate active and passive samples of a training data set the best. One method to determine this probeset is to perform a statistical test, e.g. the t-test, and select the probeset with the lowest p-value. The training data set's expression levels of the probe with the lowest p-value is by definition the probe with the least likely probability that the expression levels of the (known) active and passive samples overlap. Another selection method is based on odds-ratios (see also section 4 below). In such a model, one or more expression level(s) are provided for each of the one or more target gene(s) and the one or more linear combination(s) comprise a linear combination including for each of the one or more target gene(s) a weighted term, each weighted term being based on only one expression level of the one or more expression level(s) provided for the respective target gene. If the only one expression level is chosen per target gene as described above, the model is called a "most discriminant probesets" model in the following.

An alternative to the "most discriminant probesets" model, it is possible, in the case where possibly multiple expression levels are measured per target gene, to make use of all the expression levels that are provided per target gene. In such a model, one or more expression level(s) are provided for each of the one or more target gene(s) and the one or more linear combination(s) comprise a linear combination of all expression levels of the one or more expression level(s) provided for the one or more target gene(s). In other words, for each of the one or more target gene(s), each of the one or more expression level(s) provided for the respective target gene may be weighted in the linear combination by its own (individual) weight. This variant is called an "all probesets" model in the following. It has an advantage of being relatively simple while making use of all the provided expression levels.

Both models as described above have in common that they are what may be regarded as "single-layer" models, in which the level of the TF element is calculated based on a linear combination of expression levels.

After the level of the TF element has been determined by evaluating the respective model, the determined TF element level can be thresholded in order to infer the activity of the cellular signaling pathway. A method to calculate such an appropriate threshold is by comparing the determined TF element level w/c of training samples known to have a passive pathway and training samples with an active pathway. A method that does so and also takes into account the variance in these groups is given by using a threshold $$thr = \frac{\sigma_{wlc_{pas}}\mu_{wlc_{act}} + \sigma_{wlc_{act}}\mu_{wlc_{pas}}}{\sigma_{wlc_{pas}} + \sigma_{wlc_{act}}} \quad (1)$$

where $\sigma$ and $\mu$ are the standard deviation and the mean of the training samples. In case only a small number of samples are available in the active and/or passive training samples, a pseudocount may be added to the calculated variances based on the average of the variances of the two groups:

$$\tilde{v} = \frac{v_{wlc_{act}} + v_{wlc_{pas}}}{2} \quad (2)$$

$$\tilde{v}_{wlc_{act}} = \frac{x\tilde{v} + (n_{act}-1)v_{wlc_{act}}}{x + n_{act} - 1}$$

$$\tilde{v}_{wlc_{pas}} = \frac{x\tilde{v} + (n_{pas}-1)v_{wlc_{pas}}}{x + n_{pas} - 1}$$

where $v$ is the variance of the groups and $x$ a positive pseudocount. The standard deviation $\sigma$ can next be obtained by taking the square root of the variance $v$.

The threshold can be subtracted from the determined level of the TF element w/c for ease of interpretation, resulting in the pathway's activity score, such that negative values corresponds to passive pathways and positive values to active pathways.

Figure 3:
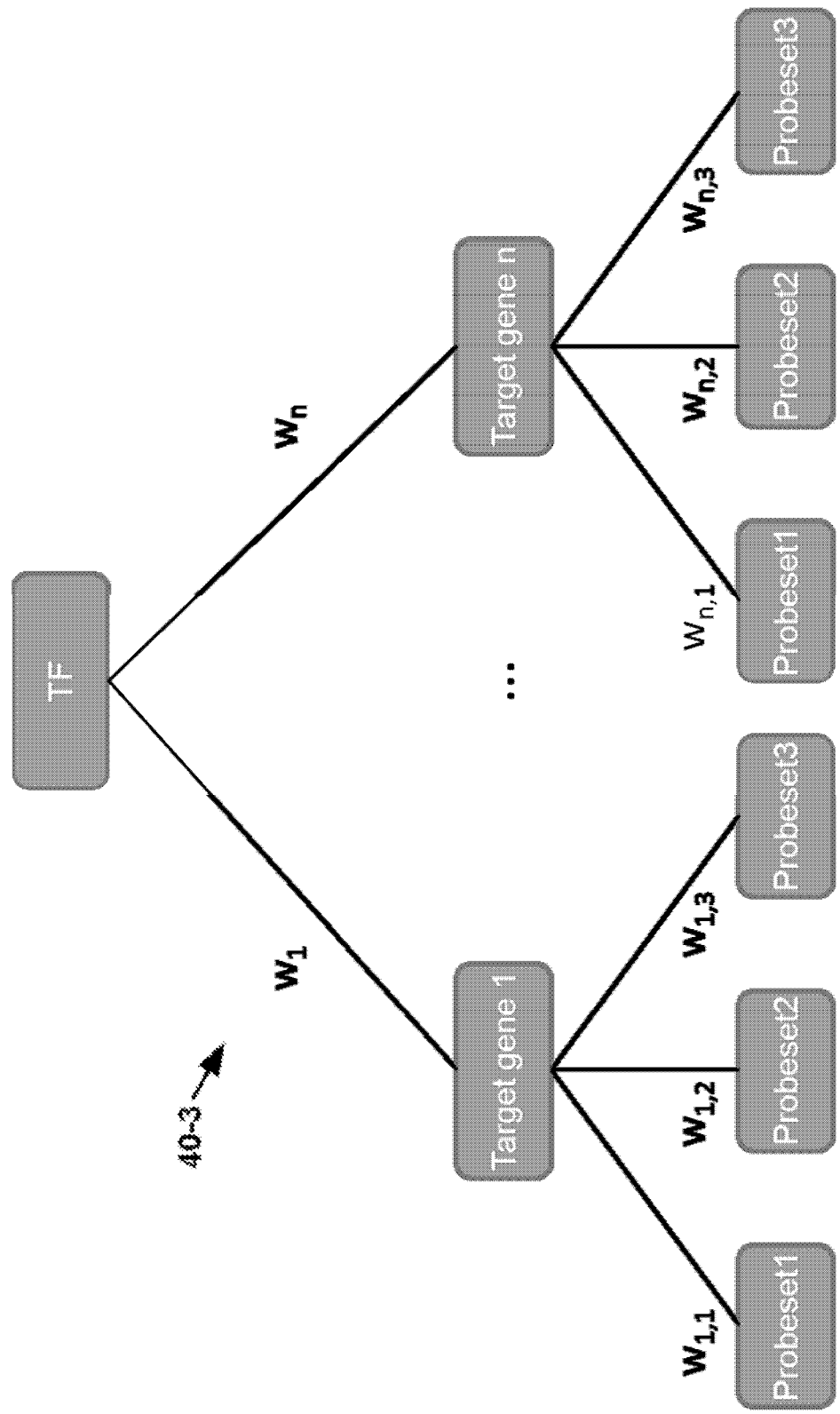

FIG. 3 shows, as an alternative to the described "single-layer" models, an illustrative "two-layer" model representing the experimental determination of active signaling of a pathway in more detail. For every target gene a summary level is calculated using a linear combination based on the measured intensities of its associated probesets ("first (bottom) layer"). The calculated summary value is subsequently combined with the summary values of the other target genes of the pathway using a further linear combination ("second (upper) layer"). The weights can be either learned from a training data set or based on expert knowledge or a combination thereof. Phrased differently, in the "two-layer" model, one or more expression level(s) are provided for each of the one or more target gene(s) and the one or more linear combination(s) comprise for each of the one or more target gene(s) a first linear combination of all expression levels of the one or more expression level(s) provided for the respective target gene ("first (bottom) layer"). The model is further based at least in part on a further linear combination including for each of the one or more target gene(s) a weighted term, each weighted term being based on the first linear combination for the respective target gene ("second (upper) layer").

The calculation of the summary values can, in a preferred version of the "two-layer" model, include defining a threshold for each target gene using the training data and subtracting the threshold from the calculated linear combination, yielding the gene summary. Here the threshold may be chosen such that a negative gene summary level corresponds with a downregulated target gene and that a positive gene summary level corresponds with an upregulated target gene. Also, it is possible that the gene summary values are transformed using e.g. one of the above-mentioned transformations (fuzzy, discrete, etc.) before they are combined in the "second (upper) layer".

After the level of the TF element has been determined by evaluating the "two-layer" model, the determined TF element level can be thresholded in order to infer the activity of the cellular signaling pathway, as described above.

In the following, the models described above are collectively denoted as "(pseudo-) linear models."

EXAMPLE 2

Selection of Target Genes

A transcription factor (TF) is a protein complex (that is, a combination of proteins bound together in a specific structure) or a protein that is able to regulate transcription from target genes by binding to specific DNA sequences, thereby controlling the transcription of genetic information from DNA to mRNA. The mRNA directly produced due to this action of the transcription complex is herein referred to as a "direct target gene". Pathway activation may also result in more secondary gene transcription, referred to as "indirect target genes". In the following, (pseudo-)linear models comprising or consisting of direct target genes, as direct links between pathway activity and mRNA level, are preferred, however the distinction between direct and indirect target genes is not always evident. Here a method to select direct target genes using a scoring function based on available literature data is presented. Nonetheless, accidental selection of indirect target genes cannot be ruled out due to limited information and biological variations and uncertainties.

Specific pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a target gene, like for example a mRNA increasing on an microarray of an embryo in which it is known that the HH pathway is active, other evidence can be very strong, like the combination of an identified pathway transcription factor binding site and retrieval of this site in a chromatin immunoprecipitation (ChIP) assay after stimulation of the specific pathway in the cell and increase in mRNA after specific stimulation of the pathway in a cell line.

Several types of experiments to find specific pathway target genes can be identified in the scientific literature, such as (but not limited to):

1. ChIP experiments in which direct binding of a pathway-transcription factor to its binding site on the genome is shown. Example: By using chromatin-immunoprecipitation (ChIP) technology subsequently putative functional TCF4 transcription factor binding sites in the DNA of colon cell lines with and without active Wnt pathway were identified, as a subset of the binding sites recognized purely based on nucleotide sequence. Putative functionality was identified as ChIP-derived evidence that the transcription factor was found to bind to the DNA binding site.
2. Electrophoretic Mobility Shift (EMSA) assays which show in vitro binding of a transcription factor to a fragment of DNA containing the binding sequence. Compared to ChIP-based evidence EMSA-based evidence is less strong, since it cannot be translated to the in vivo situation.
3. Stimulation of the pathway and measuring mRNA profiles on a microarray or using RNA sequencing, using pathway-inducible cell lines and measuring mRNA profiles measured several time points after induction—in the presence of cycloheximide, which inhibits translation to protein, thus the induced mRNAs are assumed to be direct target genes.
4. Similar to 3, but using quantitative PCR to measure the amounts of mRNAs.
5. Identification of transcription factor binding sites in the genome using a bioinformatics approach. Example for the Wnt pathway: Using the known TCF4-beta catenin transcription factor DNA binding sequence, a software program was run on the human genome sequence, and potential binding sites were identified, both in gene promoter regions and in other genomic regions.
6. Similar as 3, only in the absence of cycloheximide.
7. Similar to 4, only in the absence of cycloheximide.
8. mRNA expression profiling of specific tissue or cell samples of which it is known that the pathway is active, however in absence of the proper negative control condition.

In the simplest form one can give every potential target mRNA 1 point for each of these experimental approaches in which the target mRNA was identified.

Alternatively, points can be given incrementally; meaning one technology 1 point, second technology adds a second point, and so on. Using this relatively ranking strategy, one can make a list of most reliable target genes.

Alternatively, ranking in another way can be used to identify the target genes that are most likely to be direct target genes, by giving a higher number of points to the technology that provides most evidence for an in vivo direct target gene, in the list above this would mean 8 points for experimental approach 1), 7 to 2), and going down to one point for experimental approach 8. Such a list may be called "general target gene list".

Despite the biological variations and uncertainties, the inventors assumed that the direct target genes are the most likely to be induced in a tissue-independent manner. A list of these target genes may be called "evidence curated target gene list". These curated target lists have been used to construct computational models that can be applied to samples coming from different tissue and/or cell sources.

The "general target gene list" probably contains genes that are more tissue specific, and can be potentially used to optimize and increase sensitivity and specificity of the model for application at samples from a specific tissue, like breast cancer samples.

The following will illustrate exemplary how the selection of an evidence curated target gene list specifically was constructed for the ER pathway.

For the purpose of selecting ER target genes used as input for the (pseudo-)linear models described herein, the following three criteria were used:

1. Gene promoter/enhancer region contains an estrogen response element (ERE) motif:
   a. The ERE motif should be proven to respond to estrogen, e.g., by means of a transient transfection assay in which the specific ERE motif is linked to a reporter gene, and
   b. The presence of the ERE motif should be confirmed by, e.g., an enriched motif analysis of the gene promoter/enhancer region.
2. ER (differentially) binds in vivo to the promoter/enhancer region of the gene in question, demonstrated by, e.g., a ChIP/CHIP experiment or a chromatin immunoprecipitation assay:
   a. ER is proven to bind to the promoter/enhancer region of the gene when the ER pathway is active, and
   b. (preferably) does not bind (or weakly binds) to the gene promoter/enhancer region of the gene if the ER pathway is not active.
3. The gene is differentially transcribed when the ER pathway is active, demonstrated by, e.g.,
   a. fold enrichment of the mRNA of the gene in question through real time PCR, or microarray experiment, or
   b. the demonstration that RNA Pol II binds to the promoter region of the gene through an immunoprecipitation assay.

The selection was done by defining as ER target genes the genes for which enough and well documented experimental evidence was gathered proving that all three criteria mentioned above were met. A suitable experiment for collecting evidence of ER differential binding is to compare the results of, e.g., a ChIP/CHIP experiment in a cancer cell line that responds to estrogen (e.g., the MCF-7 cell line), when exposed or not exposed to estrogen. The same holds for collecting evidence of mRNA transcription.

The foregoing discusses the generic approach and a more specific example of the target gene selection procedure that has been employed to select a number of target genes based upon the evidence found using above mentioned approach. The lists of target genes used in the (pseudo-)linear models for exemplary pathways, namely the Wnt, ER, HH and AR pathways are shown in Table 1, Table 2, Table 3 and Table 4, respectively.

The target genes of the ER pathway used for the (pseudo-)linear models of the ER pathway described herein (shown in Table 2) contain a selection of target genes based on their literature evidence score; only the target genes with the highest evidence scores (preferred target genes according to the invention) were added to this short list. The full list of ER target genes, including also those genes with a lower evidence score, is shown in Table 5.

A further subselection or ranking of the target genes of the Wnt, ER, HH and AR pathways shown in Table 1, Table 2, Table 3 and Table 4 was performed based on a combination of the literature evidence score and the odds ratios calculated using the training data sets linking the probeset nodes to the corresponding target gene nodes. The odds ratios are calculated using a cutoff value, e.g. the median of all training samples if the same number of active and passive training samples are used; every value above the cutoff is declared to be high and below the cutoff low. This is done for the training samples where the pathway is known to be active or passive. Subsequently the odds ratio for a specific target gene or probeset can be calculates as follows:

$$f(\text{active},\text{low}) = n(\text{active},\text{low})/(n(\text{active},\text{low}) + n(\text{active},\text{high}))$$

$$f(\text{passive},\text{low}) = n(\text{passive},\text{low})/(n(\text{passive},\text{low}) + n(\text{passive},\text{high}))$$

$$\text{Odds ratio} = f(\text{passive},\text{low})/(1-f(\text{passive},\text{low}))*(1-f(\text{active},\text{low}))/f(\text{active},\text{low}) \quad (3)$$

With n(active, low) the number of training samples known to have an active pathway that were found to have an expression level below the cutoff, n(passive, low) the number of training samples known to have a passive pathway that were found to have an expression level below the cutoff, and so on. f(active, low) and f(passive, low) the fraction of samples known to have an active or passive pathway, respectively, and found to have an expression level below the cutoff.

Alternatively, to avoid undefined odds ratios (division by zero) one can add a for example a pseudocount to the fraction calculation, e.g.:

$$f(\text{active},\text{low})_{pseudo} = (n(\text{active},\text{low})+1)/(n(\text{active},\text{low})+n(\text{active},\text{high})+2)$$

$$f(\text{passive},\text{low})_{pseudo} = (n(\text{passive},\text{low})+1)/(n(\text{passive},\text{low})+n(\text{passive},\text{high})+2) \quad (4)$$

Alternatively, one can also replace the absolute number of samples exhibiting a probative activity by assuming some uncertainty (noise) in the measurement setting and calculate for each training sample a probability of being either "low" or "high" assuming e.g. a normal distribution (called "soft evidence"). Subsequently, the fraction calculations can be calculated following the aforementioned calculations.

$$f(\text{active},\text{low})_{soft} = (\Sigma p(\text{active},\text{low})+1)/(\Sigma p(\text{active},\text{low})+\Sigma p(\text{active},\text{high})+2)$$

$$f((\text{passive},\text{low})_{soft} = (\Sigma p(\text{passive},\text{low})+1)/(\Sigma p(\text{passive},\text{low})+\Sigma p(\text{passive},\text{high})+2) \quad (5)$$

With p(active, low) and p(passive, low) the probability for each sample that the observation is below the cutoff, assuming a standard distribution with the mean equal to the measured expression level of the respective training sample and a standard deviation equal to an estimation of the uncertainty associated with the expression level measurement, e.g. 0.25 on a log 2 scale. These probabilities are summed up over all the training samples, and next the pseudocount is added.

The odds ratio is an assessment of the importance of the target gene in inferring activity of the pathways. In general, it is expected that the expression level of a target gene with a higher odds ratio is likely to be more informative as to the overall activity of the pathway as compared with target genes with lower odds ratios. However, because of the complexity of cellular signaling pathways it is to be understood that more complex interrelationships may exist between the target genes and the pathway activity—for example, considering expression levels of various combinations of target genes with low odds ratios may be more probative than considering target genes with higher odds ratios in isolation. In Wnt, ER, HH and AR modeling reported herein, it has been found that the target genes shown in Table 6, Table 7, Table 8 and Table 9 are of a higher probative nature for predicting the Wnt, ER, HH and AR pathway activities as compared with the lower-ranked target genes (thus, the target genes shown in Tables 6 to 9 are particularly preferred according to the present invention). Nonetheless, given the relative ease with which acquisition technology such as microarrays can acquire expression levels for large sets of genes, it is contemplated to utilize some or all of the target genes of Table 6, Table 7, Table 8 and Table 9, and to optionally additionally use one, two, some, or all of the additional target genes of ranks shown in Table 1, Table 2, Table 3 and Table 4, in the (pseudo-)linear models as depicted in FIGS. 1 to 3.

TABLE 1

Evidence curated list of target genes of the Wnt pathway used in the (pseudo-) linear models and associated probesets used to measure the mRNA expression level of the target genes (# = sequence number in accompanying sequence listing).

| Target gene | Probeset | # |
|---|---|---|
| ADRA2C | 1206128_at | 4 |
| ASCL2 | 207607_at | 10 |
|  | 229215_at |  |
| AXIN2 | 222695_s_at | 13 |
|  | 222696_at |  |
|  | 224176_s_at |  |
|  | 224498_x_at |  |
| BMP7 | 209590_at | 17 |
|  | 209591_s_at |  |
|  | 211259_s_at |  |
|  | 211260_at |  |
| CCND1 | 208711_s_at | 27 |
|  | 208712_at |  |
|  | 214019_at |  |
| CD44 | 1557905_s_at | 30 |
|  | 1565868_at |  |
|  | 204489_s_at |  |
|  | 204490_s_at |  |
|  | 209835_x_at |  |
|  | 210916_s_at |  |
|  | 212014_x_at |  |
|  | 212063_at |  |
|  | 216056_at |  |
|  | 217523_at |  |
|  | 229221_at |  |
|  | 234411_x_at |  |
|  | 234418_x_at |  |
| COL18A1 | 209081_s_at | 40 |
|  | 209082_s_at |  |

TABLE 1-continued

Evidence curated list of target genes of the Wnt pathway used in the (pseudo-) linear models and associated probesets used to measure the mRNA expression level of the target genes (# = sequence number in accompanying sequence listing).

| Target gene | Probeset | # |
|---|---|---|
| DEFA6 | 207814_at | 52 |
| DKK1 | 204602_at | 54 |
| EPHB2 | 209588_at | 67 |
|  | 209589_s_at |  |
|  | 210651_s_at |  |
|  | 211165_x_at |  |
| EPHB3 | 1438_at | 68 |
|  | 204600_at |  |
| FAT1 | 201579_at | 72 |
| FZD7 | 203705_s_at | 90 |
|  | 203706_s_at |  |
| GLUL | 200648_s_at | 95 |
|  | 215001_s_at |  |
|  | 217202_s_at |  |
|  | 217203_at |  |
|  | 242281_at |  |
| HNF1A | 210515_at | 102 |
|  | 216930_at |  |
| IL8 | 202859_x_at | 110 |
|  | 211506_s_at |  |
| KIAA1199 | 1554685_a_at | 119 |
|  | 212942_s_at |  |
| KLF6 | 1555832_s_at | 121 |
|  | 208960_s_at |  |
|  | 208961_s_at |  |
|  | 211610_at |  |
|  | 224606_at |  |
| LECT2 | 207409_at | 129 |
| LEF1 | 210948_s_at | 130 |
|  | 221557_s_at |  |
|  | 221558_s_at |  |
| LGR5 | 210393_at | 131 |
|  | 213880_at |  |
| MYC | 202431_s_at | 142 |
|  | 244089_at |  |
| NKD1 | 1553115_at | 150 |
|  | 229481_at |  |
|  | 232203_at |  |
| OAT | 201599_at | 157 |
| PPARG | 208510_s_at | 173 |
| REG1B | 205886_at | 184 |
| RNF43 | 218704_at | 189 |
| SLC1A2 | 1558009_at | 200 |
|  | 1558010_s_at |  |
|  | 208389_s_at |  |
|  | 225491_at |  |
| SOX9 | 202935_s_at | 209 |
|  | 202936_s_at |  |
| SP5 | 235845_at | 210 |
| TBX3 | 219682_s_at | 215 |
|  | 222917_s_at |  |
|  | 225544_at |  |
|  | 229576_s_at |  |
| TCF7L2 | 212759_s_at | 219 |
|  | 212761_at |  |
|  | 212762_s_at |  |
|  | 216035_x_at |  |
|  | 216037_x_at |  |
|  | 216511_s_at |  |
|  | 236094_at |  |
| TDGF1 | 206286_s_at | 220 |
| ZNRF3 | 226360_at | 248 |

TABLE 2

Evidence curated list of target genes of the ER pathway used in the (pseudo-) linear models and associated probesets used to measure the mRNA expression level of the target genes (# = sequence number in accompanying sequence listing). The "most discriminative probesets" are marked by underlining.

| Target gene | Probeset | # | Target gene | Probeset | # |
|---|---|---|---|---|---|
| AP1B1 | 205423_at | 5 | RARA | 1565358_a | 183 |
| ATP5J | 202325_s_at | 12 | | 203749_s_at | |
| COL18A1 | 209081_s_at | 40 | | 203750_s_at | |
| | 209082_s_at | | | 211605_s_at | |
| COX7A2L | 201256_at | 41 | | 216300_x_at | |
| CTSD | 200766_at | 46 | SOD1 | 200642_at | 205 |
| DSCAM | 211484_s_at | 59 | TFF1 | 205009_at | 221 |
| | 237268_at | | TRIM25 | 206911_at | 230 |
| | 240218_at | | | 224806_at | |
| EBAG9 | 204274_at | 61 | XBP1 | 200670_at | 244 |
| | 204278_s_at | | | 242021_at | |
| ESR1 | 205225_at | 70 | GREB1 | 205862_at | 97 |
| | 211233_x_at | | | 210562_at | |
| | 211234_x_at | | | 210855_at | |
| | 211235_s_at | | IGFBP4 | 201508_at | 106 |
| | 211627_x_at | | MYC | 202431_s_at | 142 |
| | 215551_at | | | 244089_at | |
| | 215552_s_at | | SGK3 | 227627_at | 196 |
| | 217163_at | | | 220038_at | |
| | 217190_x_at | | WISP2 | 205792_at | 241 |
| | 207672_at | | ERBB2 | 210930_s_at | 69 |
| HSPB1 | 201841_s_at | 103 | | 216836_s_at | |
| KRT19 | 201650_at | 124 | | 234354_x_at | |
| | 228491_at | | CA12 | 203963_at | 22 |
| NDUFV3 | 226209_at | 148 | | 204508_s_at | |
| | 226616_s_at | | | 204509_at | |
| NRIP1 | 202599_s_at | 154 | | 210735_s_at | |
| | 202600_s_at | | | 214164_s_at | |
| PGR | 208305_at | 162 | | 215867_x_at | |
| | 228554_at | | | 241230_at | |
| PISD | 202392_s_at | 164 | CDH26 | 232306_at | 32 |
| PRDM15 | 230553_at | 174 | | 233391_at | |
| | 230777_s_at | | | 233622_at | |
| | 231931_at | | | 233663_s_at | |
| | 234524_at | | CELSR2 | 204029_at | 36 |
| | 236061_at | | | 36499_at | |
| PTMA | 200772_x_at | 179 | | | |
| | 200773_x_at | | | | |
| | 208549_x_at | | | | |
| | 211921_x_at | | | | |

TABLE 3

Evidence curated list of target genes of the HH pathway used in the (pseudo-) linear models and associated probesets used to measure the mRNA expression level of the target genes (# = sequence number in accompanying sequence listing).

| Target gene | Probeset | # | Target gene | Probeset | # |
|---|---|---|---|---|---|
| GLI1 | 206646_at | 93 | CTSL1 | 202087_s_at | 47 |
| PTCH1 | 1555520_at | 177 | TCEA2 | 203919_at | 216 |
| | 208522_s_at | | | 238173_at | |
| | 209815_at | | | 241428_x_at | |
| | 209816_at | | MYLK | 1563466_at | 145 |
| | 238754_at | | | 1568770_at | |
| PTCH2 | 221292_at | 178 | | 1569956_at | |
| HHIP | 1556037_s_at | 101 | | 202555_s_at | |
| | 223775_at | | | 224823_at | |
| | 230135_at | | FYN | 1559101_at | 88 |
| | 237466_s_at | | | 210105_s_at | |
| SPP1 | 1568574_x_at | 212 | | 212486_s_at | |
| | 209875_s_at | | | 216033_at | |
| TSC22D1 | 215111_s_at | 232 | PITRM1 | 205273_s_at | 165 |
| | 235315_at | | | 239378_at | |
| | 243133_at | | CFLAR | 208485_x_at | 37 |
| | 239123_at | | | 209508_x_at | |

TABLE 3-continued

Evidence curated list of target genes of the HH pathway used in the (pseudo-) linear models and associated probesets used to measure the mRNA expression level of the target genes (# = sequence number in accompanying sequence listing).

| Target gene | Probeset | # | Target gene | Probeset | # |
|---|---|---|---|---|---|
| CCND2 | 200951_s_at | 28 | | 209939_x_at | |
| | 200952_s_at | | | 210563_x_at | |
| | 200953_s_at | | | 210564_x_at | |
| | 231259_at | | | 211316_x_at | |
| H19 | 224646_x_at | 253 | | 211317_s_at | |
| | 224997_x_at | | | 211862_x_at | |
| IGFBP6 | 203851_at | 107 | | 214486_x_at | |
| TOM1 | 202807_s_at | 229 | | 214618_at | |
| JUP | 201015_s_at | 229 | | 214618_at | |
| FOXA2 | 210103_s_at | 82 | | 235427_at | |
| | 214312_at | | | 237367_x_at | |
| | 40284_at | | | 239629_at | |
| MYCN | 209756_s_at | 144 | | 224261_at | |
| | 209757_s_at | | IL1R2 | 205403_at | 108 |
| | 211377_x_at | | | 211372_s_at | |
| | 234276_at | | S100A7 | 205916_at | 254 |
| | 242026_at | | S100A9 | 203535_at | 255 |
| NKX2_2 | 206915_at | 249 | CCND1 | 208711_s_at | 27 |
| NKX2_8 | 207451_at | 250 | | 208712_at | |
| RAB34 | 1555630_a_at | 182 | | 214019_at | |
| | 224710_at | | JAG2 | 209784_s_at | 115 |
| MIF | 217871_s_at | 134 | | 32137_at | |
| GLI3 | 1569342_at | 94 | FOXM1 | 202580_s_at | 85 |
| | 205201_at | | FOXF1 | 205935_at | 83 |
| | 227376_at | | FOXL1 | 216572_at | 84 |
| FST | 204948_s_at | 87 | | 243409_at | |
| | 207345_at | | | | |
| | 226847_at | | | | |
| BCL2 | 203684_s_at | 14 | | | |
| | 203685_at | | | | |
| | 207004_at | | | | |
| | 207005_s_at | | | | |

TABLE 4

Evidence curated list of target genes of the AR pathway used in the (pseudo-) linear models and associated probesets used to measure the mRNA expression level of the target genes (# = sequence number in accompanying sequence listing)

| Target gene | Probeset | # |
|---|---|---|
| ABCC4 | 1554918_a_at | 2 |
| | 155039_a_at | |
| | 203196_at | |
| APP | 200602_at | 7 |
| | 211277_x_at | |
| | 214953_s_at | |
| AR | 211110_s_at | 8 |
| | 211621_at | |
| | 226193_at | |
| | 226197_at | |
| CDKN1A | 1555186_at | 34 |
| | 202284_s_at | |
| CREB3L4 | 226455_at | 42 |
| DHCR24 | 200862_at | 53 |
| DRG1 | 202810_at | 58 |
| EAF2 | 202810_at | 60 |
| | 1568673_s_at | |
| | 219551_at | |
| ELL2 | 214446_at | 65 |
| | 226099_at | |
| | 226982_at | |
| FGF8 | 208449_s_at | 75 |
| FKBP5 | 204560_at | 77 |
| | 224840_at | |
| | 224856_at | |

TABLE 4-continued

Evidence curated list of target genes of the AR pathway used in the (pseudo-) linear models and associated probesets used to measure the mRNA expression level of the target genes (# = sequence number in accompanying sequence listing)

| Target gene | Probeset | # |
|---|---|---|
| GUCY1A3 | 221942_s_at | 99 |
|  | 227235_at |  |
|  | 229530_at |  |
|  | 239580_at |  |
| IGF1 | 209540_at | 105 |
|  | 209541_at |  |
|  | 209542_x_at |  |
|  | 211577_s_at |  |
| KLK2 | 1555545_at | 122 |
|  | 209854_s_at |  |
|  | 209855_s_at |  |
|  | 210339_s_at |  |
| LCP1 | 208885_at | 128 |
| LRIG1 | 211596_s_at | 132 |
|  | 238339_x_at |  |
| NDRG1 | 200632_s_at | 147 |
| NKX3_1 | 209706_at | 251 |
|  | 211497_x_at |  |
|  | 211498_s_at |  |
| NTS | 206291_at | 155 |
| PLAU | 205479_s_at | 167 |
|  | 211668_s_at |  |
| PMEPA1 | 217875_s_at | 169 |
|  | 222449_at |  |
|  | 222450_at |  |
| PPAP2A | 209147_s_at | 171 |
|  | 210946_at |  |
| PRKACB | 202741_at | 175 |
|  | 202742_s_at |  |
|  | 235780_at |  |
| KLK3 | 204582_s_at | 123 |
|  | 204583_x_at |  |
| PTPN1 | 202716_at | 180 |
|  | 217686_at |  |
| SGK1 | 201739_at | 195 |
| TACC2 | 1570546_a_at | 214 |
|  | 1570546_a_at |  |
|  | 202289_s_at |  |
|  | 211382_s_at |  |
| TMPRSS2 | 1570433_at | 225 |
|  | 205102_at |  |
|  | 211689_s_at |  |
|  | 226553_at |  |
| UGT2B15 | 207392_x_at | 236 |
|  | 216687_x_at |  |

TABLE 6

Shortlist of Wnt target genes based on literature evidence score and odds ratio (# = sequence number in accompanying sequence listing).

| Target gene | # |
|---|---|
| KIAA1199 | 119 |
| AXIN2 | 13 |
| CD44 | 30 |
| RNF43 | 189 |
| MYC | 142 |
| TBX3 | 215 |
| TDGF1 | 220 |
| SOX9 | 209 |
| ASCL2 | 10 |
| IL8 | 110 |
| SP5 | 210 |
| ZNRF3 | 248 |
| EPHB2 | 67 |
| LGR5 | 131 |
| EPHB3 | 68 |
| KLF6 | 121 |
| CCND1 | 27 |
| DEFA6 | 52 |
| FZD7 | 90 |

TABLE 7

Shortlist of ER target genes based on literature evidence score and odds ratio (# = sequence number in accompanying sequence listing).

| Target gene | # |
|---|---|
| CDH26 | 32 |
| SGK3 | 196 |
| PGR | 162 |
| GREB1 | 97 |
| CA12 | 22 |
| XBP1 | 244 |
| CELSR2 | 36 |
| WISP2 | 241 |
| DSCAM | 59 |
| ERBB2 | 69 |
| CTSD | 46 |
| TFF1 | 221 |
| NRIP1 | 154 |

TABLE 5

Gene symbols of the ER target genes found to have significant literature evidence (=ER target genes longlist) (# = sequence number in accompanying sequence listing).

| Gene symbol | # | Gene symbol | # | Gene symbol | # | Gene symbol | # |
|---|---|---|---|---|---|---|---|
| AP1B1 | 5 | SOD1 | 205 | MYC | 142 | ENSA | 66 |
| COX7A2L | 41 | TFF1 | 221 | ABCA3 | 1 | KIAA0182 | 118 |
| CTSD | 46 | TRIM25 | 230 | ZNF600 | 247 | BRF1 | 19 |
| DSCAM | 59 | XBP1 | 245 | PDZK1 | 160 | CASP8AP2 | 25 |
| EBAG9 | 61 | GREB1 | 97 | LCN2 | 127 | CCNH | 29 |
| ESR1 | 70 | IGFBP4 | 106 | TGFA | 222 | CSDE1 | 43 |
| HSPB1 | 103 | SGK3 | 196 | CHEK1 | 38 | SRSF1 | 213 |
| KRT19 | 124 | WISP2 | 241 | BRCA1 | 18 | CYP1B1 | 48 |
| NDUFV3 | 148 | ERBB2 | 69 | PKIB | 166 | FOXA1 | 81 |
| NRIP1 | 154 | CA12 | 22 | RET | 188 | TUBA1A | 235 |
| PGR | 162 | CELSR2 | 36 | CALCR | 23 | GAPDH | 91 |
| PISD | 164 | CDH26 | 32 | CARD10 | 24 | SFI1 | 194 |
| PRDM15 | 174 | ATP5J | 12 | LRIG1 | 132 | ESR2 | 258 |
| PTMA | 179 | COL18A1 | 40 | MYB | 140 | MYBL2 | 141 |
| RARA | 183 | CCND1 | 27 | RERG | 187 |  |  |

TABLE 8

Shortlist of HH target genes based on literature evidence score and odds ratio (# = sequence number in accompanying sequence listing).

| Target gene | # |
|---|---|
| GLI1 | 93 |
| PTCH1 | 177 |
| PTCH2 | 178 |
| IGFBP6 | 107 |
| SPP1 | 212 |
| CCND2 | 28 |
| FST | 87 |
| FOXL1 | 84 |
| CFLAR | 37 |
| TSC22D1 | 232 |
| RAB34 | 182 |
| S100A9 | 255 |
| S100A7 | 254 |
| MYCN | 144 |
| FOXM1 | 85 |
| GLI3 | 94 |
| TCEA2 | 216 |
| FYN | 88 |
| CTSL1 | 47 |

TABLE 9

Shortlist of AR target genes based on literature evidence score and odds ratio (# = sequence number in accompanying sequence listing).

| Target gene | # |
|---|---|
| KLK2 | 122 |
| PMEPA1 | 169 |
| TMPRSS2 | 225 |
| NKX3_1 | 251 |
| ABCC4 | 2 |
| KLK3 | 123 |
| FKBP5 | 77 |
| ELL2 | 65 |
| UGT2B15 | 236 |
| DHCR24 | 53 |
| PPAP2A | 171 |
| NDRG1 | 147 |
| LRIG1 | 132 |
| CREB3L4 | 42 |
| LCP1 | 128 |
| GUCY1A3 | 99 |
| AR | 8 |
| EAF2 | 60 |

EXAMPLE 3

Comparison of Evidence Curated List and Broad Literature List

The list of Wnt target genes constructed based on literature evidence following the procedure described herein (Table 1) is compared to another list of target genes not following above mentioned procedure. The alternative list is a compilation of genes indicated by a variety of data from various experimental approaches to be a Wnt target gene published in three public sources by renowned labs, known for their expertise in the area of molecular biology and the Wnt pathway. The alternative list is a combination of the genes mentioned in Table S3 from Hatzis et al. (Hatzis P, 2008), the text and Table S1A from de Sousa e Melo (de Sousa E Melo F, 2011) and the list of target genes collected and maintained by Roel Nusse, a pioneer in the field of Wnt signaling (Nusse, 2012). The combination of these three sources resulted in a list of 124 genes (=broad literature list, see Table 10). Here the question whether the performance in predicting Wnt activity in clinical samples by the algorithm derived from this alternative list is performing similarly or better compared to the model constructed on the basis of the existing list of genes (=evidence curated list, Table 1) is discussed.

TABLE 10

Alternative list of Wnt target genes (=broad literature list) (# = sequence number in accompanying sequence listing).

| Target gene | Reference | # |
|---|---|---|
| ADH6 | de Sousa e Melo et al. | 3 |
| ADRA2C | Hatzis et al. | 4 |
| APCDD1 | de Sousa e Melo et al. | 6 |
| ASB4 | de Sousa e Melo et al. | 9 |
| ASCL2 | Hatzis et al., de Sousa e Melo et al. | 10 |
| ATOH1 | Nusse | 11 |
| AXIN2 | Hatzis et al., de Sousa e Melo et al., Nusse | 13 |
| BIRC5 | Nusse | 15 |
| BMP4 | Nusse | 16 |
| BMP7 | Hatzis et al. | 17 |
| BTRC | Nusse | 20 |
| BZRAAP1 | de Sousa e Melo et al. | 21 |
| SBSPON | de Sousa e Melo et al. | 259 |
| CCL24 | de Sousa e Melo et al. | 26 |
| CCND1 | Nusse | 27 |
| CD44 | Nusse | 30 |
| CDH1 | Nusse | 31 |
| CDK6 | Hatzis et al. | 33 |
| CDKN2A | Nusse | 35 |
| CLDN1 | Nusse | 39 |
| COL18A1 | Hatzis et al. | 40 |
| CTLA4 | Nusse | 44 |
| CYP4X1 | de Sousa e Melo et al. | 49 |
| CYR61 | Nusse | 50 |
| DEFA5 | de Sousa e Melo et al. | 51 |
| DEFA6 | de Sousa e Melo et al. | 52 |
| DKK1 | de Sousa e Melo et al., Nusse | 54 |
| DKK4 | de Sousa e Melo et al. | 55 |
| DLL1 | Nusse | 56 |
| DPEP1 | de Sousa e Melo et al. | 57 |
| EDN1 | Nusse | 62 |
| EGFR | Nusse | 64 |
| EPHB2 | Hatzis et al., de Sousa e Melo et al., Nusse | 67 |
| EPHB3 | Hatzis et al., Nusse | 68 |
| ETS2 | Hatzis et al. | 71 |
| FAT1 | Hatzis et al. | 72 |
| FGF18 | Nusse | 73 |
| FGF20 | Nusse | 74 |
| FGF9 | Nusse | 76 |
| FLAD1 | Hatzis et al. | 78 |
| AK122582 | Hatzis et al. | 262 |
| FN1 | Nusse | 79 |
| FOSL1 | Nusse | 80 |
| FOXN1 | Nusse | 86 |
| FST | Nusse | 87 |
| FZD2 | Nusse | 89 |
| FZD7 | de Sousa e Melo et al. | 90 |
| GAST | Nusse | 92 |
| GMDS | Hatzis et al. | 96 |
| GREM2 | Nusse | 98 |
| HES6 | Hatzis et al. | 100 |
| HNF1A | Nusse | 102 |
| ID2 | Nusse | 104 |
| IL22 | de Sousa e Melo et al. | 109 |
| IL8 | Nusse | 110 |
| IRX3 | de Sousa e Melo et al. | 111 |
| IRX5 | de Sousa e Melo et al. | 112 |
| ISL1 | Nusse | 113 |
| JAG1 | Nusse | 114 |
| JUN | Nusse | 116 |
| KIAA1199 | de Sousa e Melo et al. | 119 |
| KLF4 | Hatzis et al. | 120 |
| L1CAM | Nusse | 125 |
| LBH | Nusse | 126 |

TABLE 10-continued

Alternative list of Wnt target genes (=broad literature list) (# = sequence number in accompanying sequence listing).

| Target gene | Reference | # |
|---|---|---|
| LEF1 | Hatzis et al., de Sousa e Melo et al., Nusse | 130 |
| LGR5 | de Sousa e Melo et al., Nusse | 131 |
| LOC283859 | de Sousa e Melo et al. | 260 |
| MET | Nusse | 133 |
| MMP2 | Nusse | 135 |
| MMP26 | Nusse | 136 |
| MMP7 | Nusse | 137 |
| MMP9 | Nusse | 138 |
| MRPS6 | Hatzis et al. | 139 |
| MYC | Hatzis et al., Nusse | 142 |
| MYCBP | Nusse | 143 |
| MYCN | Nusse | 144 |
| NANOG | Nusse | 146 |
| NKD1 | de Sousa e Melo et al. | 150 |
| NOS2 | Nusse | 151 |
| NOTUM | de Sousa e Melo et al. | 152 |
| NRCAM | Nusse | 153 |
| NUAK2 | Hatzis et al. | 156 |
| PDGFB | Hatzis et al. | 159 |
| PFDN4 | Hatzis et al. | 161 |
| PLAUR | Nusse | 168 |
| POU5F1 | Nusse | 170 |
| PPARD | Nusse | 172 |
| PROX1 | de Sousa e Melo et al. | 176 |
| PTPN1 | Hatzis et al. | 180 |
| PTTG1 | Nusse | 181 |
| REG3A | de Sousa e Melo et al. | 185 |
| REG4 | de Sousa e Melo et al. | 186 |
| RPS27 | Hatzis et al. | 190 |
| RUNX2 | Nusse | 191 |
| SALL4 | Nusse | 192 |
| SLC1A1 | de Sousa e Melo et al. | 199 |
| SLC7A5 | Hatzis et al. | 201 |
| SNAI1 | Nusse | 202 |
| SNAI2 | Nusse | 203 |
| SNAI3 | Nusse | 204 |
| SIK1 | Hatzis et al. | 261 |
| SOX17 | Nusse | 206 |
| SOX2 | de Sousa e Melo et al. | 207 |
| SOX4 | Hatzis et al. | 208 |
| SOX9 | Nusse | 209 |
| SP5 | Hatzis et al., de Sousa e Melo et al. | 210 |
| SP8 | Hatzis et al. | 211 |
| TCF3 | Nusse | 217 |
| TDGF1 | Hatzis et al. | 220 |
| TIAM1 | Nusse | 224 |
| TNFSF19 | Nusse | 227 |
| TNFSF11 | Nusse | 228 |
| TRIM29 | de Sousa e Melo et al. | 231 |
| TSPAN5 | de Sousa e Melo et al. | 233 |
| TTC9 | de Sousa e Melo et al. | 234 |
| VCAN | Nusse | 237 |
| VEGFA | Nusse | 238 |
| VEGFB | Nusse | 239 |
| VEGFC | Nusse | 240 |
| WNT10A | Hatzis et al. | 242 |
| WNT3A | Nusse | 243 |
| ZBTB7C | de Sousa e Melo et al. | 246 |
| PATZ1 | Hatzis et al. | 263 |
| ZNRF3 | Hatzis et al. | 248 |

The next step consisted of finding the probesets of the Affymetrix® GeneChip Human Genome U133 Plus 2.0 array that corresponds with the genes. This process was performed using the Bioconductor plugin in R and manual curation for the probesets relevance based on the UCSC genome browser, similar to the (pseudo-)linear models described herein, thereby removing e.g. probesets on opposite strands or outside gene exon regions. For two of the 124 genes there are no probesets available on this microarray-chip and therefore could not be inserted in the (pseudo-)linear model, these are LOC283859 and WNT3A. In total 287 probesets were found to correspond to the remaining 122 genes (Table 11).

TABLE 11

Probesets associated with the Wnt target genes in the broad literature gene list (# = sequence number in accompanying sequence listing).

| Gene symbol | Probeset | # |
|---|---|---|
| ADH6 | 207544_s_at | 3 |
| | 214261_s_at | |
| ADRA2C | 206128_at | 4 |
| APCDD1 | 225016_at | 6 |
| ASB4 | 208481_at | 9 |
| | 217228_s_at | |
| | 217229_at | |
| | 235619_at | |
| | 237720_at | |
| | 237721_s_at | |
| ASCL2 | 207607_at | 10 |
| | 229215_at | |
| ATOH1 | 221336_at | 11 |
| AXIN2 | 222695_s_at | 13 |
| | 222696_at | |
| | 224176_s_at | |
| | 224498_x_at | |
| BIRC5 | 202094_at | 15 |
| | 202095_s_at | |
| | 210334_x_at | |
| BMP4 | 211518_s_at | 16 |
| BMP7 | 209590_at | 17 |
| | 209591_s_at | |
| | 211259_s_at | |
| | 211260_at | |
| BTRC | 1563620_at | 20 |
| | 204901_at | |
| | 216091_s_at | |
| | 222374_at | |
| | 224471_s_at | |
| BZRAP1 | 205839_s_at | 21 |
| SBSPON | 214725_at | 259 |
| | 235209_at | |
| | 235210_s_at | |
| CCL24 | 221463_at | 26 |
| CCND1 | 208711_s_at | 27 |
| | 208712_at | |
| | 214019_at | |
| CD44 | 1557905_s_at | 30 |
| | 204489_s_at | |
| | 204490_s_at | |
| | 209835_x_at | |
| | 210916_s_at | |
| | 212014_x_at | |
| | 212063_at | |
| | 217523_at | |
| | 229221_at | |
| CDH1 | 201130_s_at | 31 |
| | 201131_s_at | |
| | 208834_x_at | |
| CDK6 | 207143_at | 33 |
| | 214160_at | |
| | 224847_at | |
| | 224848_at | |
| | 224851_at | |
| | 231198_at | |
| | 235287_at | |
| | 243000_at | |
| CDKN2A | 207039_at | 35 |
| | 209644_x_at | |
| | 211156_at | |
| CLDN1 | 218182_s_at | 39 |
| | 222549_at | |
| COL18A1 | 209084_s_at | 40 |
| | 209082_s_at | |

TABLE 11-continued

Probesets associated with the Wnt target genes in the broad literature gene list (# = sequence number in accompanying sequence listing).

| Gene symbol | Probeset | # |
|---|---|---|
| CTLA4 | 221331_x_at | 44 |
| | 231794_at | |
| | 234362_s_at | |
| | 236341_at | |
| CYP4X1 | 227702_at | 49 |
| CYR61 | 201289_at | 50 |
| | 210764_s_at | |
| DEFA5 | 207529_at | 51 |
| DEFA6 | 207814_at | 52 |
| DKK1 | 204602_at | 54 |
| DKK4 | 206619_at | 55 |
| DLL1 | 224215_s_at | 56 |
| | 227938_s_at | |
| DPEP1 | 205983_at | 57 |
| EDN1 | 218995_s_at | 62 |
| | 222802_at | |
| EGFR | 1565483_at | 64 |
| | 1565484_x_at | |
| | 201983_s_at | |
| | 201984_s_at | |
| | 210984_x_at | |
| | 211550_at | |
| | 211551_at | |
| | 211607_x_at | |
| EPHB2 | 209588_at | 67 |
| | 209589_s_at | |
| | 210651_s_at | |
| | 211165_x_at | |
| EPHB3 | 1438_at | 68 |
| | 204600_at | |
| ETS2 | 201328_at | 71 |
| | 201329_s_at | |
| FAT1 | 201579_at | 72 |
| FGF18 | 206987_x_at | 73 |
| | 211029_x_at | |
| | 211485_s_at | |
| | 231382_at | |
| FGF20 | 220394_at | 74 |
| FGF9 | 206404_at | 76 |
| | 239178_at | |
| FLAD1 | 205661_s_at | 78 |
| | 212541_at | |
| AK122582 | 235085_at | 262 |
| FN1 | 1558199_at | 79 |
| | 210495_x_at | |
| | 211719_x_at | |
| | 212464_s_at | |
| | 214701_s_at | |
| | 214702_at | |
| | 216442_x_at | |
| FOSL1 | 204420_at | 80 |
| FOXN1 | 207683_at | 86 |
| FST | 204948_s_at | 87 |
| | 207345_at | |
| | 226847_at | |
| FZD2 | 210220_at | 89 |
| | 238129_s_at | |
| FZD7 | 203705_s_at | 90 |
| | 203706_s_at | |
| GAST | 208138_at | 92 |
| GMDS | 204875_s_at | 96 |
| | 214106_s_at | |
| GREM2 | 220794_at | 98 |
| | 235504_at | |
| | 240509_s_at | |
| HES6 | 226446_at | 100 |
| | 228169_s_at | |
| HNF1A | 210515_at | 102 |
| | 216930_at | |
| ID2 | 201565_s_at | 104 |
| | 201566_x_at | |
| | 213931_at | |

TABLE 11-continued

Probesets associated with the Wnt target genes in the broad literature gene list (# = sequence number in accompanying sequence listing).

| Gene symbol | Probeset | # |
|---|---|---|
| IL22 | 221165_s_at | 109 |
| | 222974_at | |
| IL8 | 202859_x_at | 110 |
| | 211506_s_at | |
| IRX3 | 229638_at | 111 |
| IRX5 | 210239_at | 112 |
| ISL1 | 206104_at | 113 |
| JAG1 | 209097_s_at | 114 |
| | 209098_s_at | |
| | 209099_x_at | |
| | 216268_s_at | |
| JUN | 201464_x_at | 116 |
| | 201465_s_at | |
| | 201466_s_at | |
| KIAA1199 | 1554685_a_at | 119 |
| | 212942_s_at | |
| KLF4 | 220266_s_at | 120 |
| | 221841_s_at | |
| L1CAM | 204584_at | 125 |
| | 204585_s_at | |
| LBH | 221011_s_at | 126 |
| LEF1 | 210948_s_at | 130 |
| | 221557_s_at | |
| | 221558_s_at | |
| LGR5 | 210393_at | 131 |
| | 213880_at | |
| MET | 203510_at | 133 |
| | 211599_x_at | |
| | 213807_x_at | |
| | 213816_s_at | |
| MMP2 | 1566678_at | 135 |
| | 201069_at | |
| MMP26 | 220541_at | 136 |
| MMP7 | 204259_at | 137 |
| MMP9 | 203936_s_at | 138 |
| MRPS6 | 224919_at | 139 |
| MYC | 202431_s_at | 142 |
| MYCBP | 203359_s_at | 143 |
| | 203360_s_at | |
| | 203361_s_at | |
| MYCN | 209756_s_at | 144 |
| | 209757_s_at | |
| | 211377_x_at | |
| | 234376_at | |
| NANOG | 220184_at | 146 |
| NKD1 | 1553115_at | 150 |
| | 229481_at | |
| | 232203_at | |
| NOS2 | 210037_s_at | 151 |
| NOTUM | 228649_at | 152 |
| NRCAM | 204105_s_at | 153 |
| | 216959_x_at | |
| NUAK2 | 220987_s_at | 156 |
| PDGFB | 204200_s_at | 159 |
| | 216061_x_at | |
| | 217112_at | |
| PFDN4 | 205360_at | 161 |
| | 205361_s_at | |
| | 205362_s_at | |
| PLAUR | 210845_s_at | 168 |
| | 211924_s_at | |
| | 214866_at | |
| POU5F1 | 208286_x_at | 170 |
| PPARD | 208044_s_at | 172 |
| | 210636_at | |
| | 37152_at | |
| | 242218_at | |
| PROX1 | 207401_at | 176 |
| | 228656_at | |
| PTPN1 | 202716_at | 180 |
| | 217686_at | |
| | 217689_at | |

TABLE 11-continued

Probesets associated with the Wnt target genes in the broad literature gene list (# = sequence number in accompanying sequence listing).

| Gene symbol | Probeset | # |
|---|---|---|
| PTTG1 | 203554_x_at | 181 |
| REG3A | 205815_at | 185 |
|  | 234280_at |  |
| REG4 | 1554436_a_at | 186 |
|  | 223447_at |  |
| RPS27 | 200741_s_at | 190 |
| RUNX2 | 216994_s_at | 191 |
|  | 221282_x_at |  |
|  | 232231_at |  |
|  | 236858_s_at |  |
|  | 236859_at |  |
| SALL4 | 229661_at | 192 |
| SLC1A1 | 206396_at | 199 |
|  | 213664_at |  |
| SLC7A5 | 201195_s_at | 201 |
| SNAI1 | 219480_at | 202 |
| SNAI2 | 213139_at | 203 |
| SNAI3 | 1560228_at | 204 |
| SIK1 | 208078_s_at | 261 |
|  | 232470_at |  |
| SOX17 | 219993_at | 206 |
|  | 230943_at |  |
| SOX2 | 213721_at | 207 |
|  | 213722_at |  |
|  | 228038_at |  |
| SOX4 | 201416_at | 208 |
|  | 201417_at |  |
|  | 201418_s_at |  |
|  | 213668_s_at |  |
| SOX9 | 202935_s_at | 209 |
|  | 202936_s_at |  |
| SP5 | 235845_at | 210 |
| SP8 | 237449_at | 211 |
|  | 239743_at |  |
| TCF3 | 209151_x_at | 217 |
|  | 209152_s_at |  |
|  | 209153_s_at |  |
|  | 210776_x_at |  |
|  | 213730_x_at |  |
|  | 213811_x_at |  |
|  | 215260_s_at |  |
|  | 216645_at |  |
| TDGF1 | 206286_s_at | 220 |
| TIAM1 | 206409_at | 224 |
|  | 213135_at |  |
| TNFRSF19 | 223827_at | 227 |
|  | 224090_s_at |  |
| TNFSF11 | 210643_at | 228 |
|  | 211153_s_at |  |
| TRIM29 | 202504_at | 231 |
|  | 211001_at |  |
|  | 211002_s_at |  |
| TSPAN5 | 209890_at | 233 |
|  | 213968_at |  |
|  | 225387_at |  |
|  | 225388_at |  |
| TTC9 | 213172_at | 234 |
|  | 213174_at |  |
| VCAN | 204619_s_at | 237 |
|  | 204620_s_at |  |
|  | 211571_s_at |  |
|  | 215646_s_at |  |
|  | 221731_x_at |  |
| VEGFA | 210512_s_at | 238 |
|  | 210513_s_at |  |
|  | 211527_x_at |  |
|  | 212171_x_at |  |
| VEGFB | 203683_s_at | 239 |
| VEGFC | 209946_at | 240 |
| WNT10A | 223709_s_at | 242 |
|  | 229154_at |  |
| ZBTB7C | 217675_at | 246 |
| ZBTB7C | 227782_at | 246 |
| PATZ1 | 209431_s_at | 263 |
|  | 211391_s_at |  |
|  | 210581_x_at |  |
|  | 209494_s_at |  |
| ZNRF3 | 226360_at | 248 |

Subsequently the (pseudo-)linear model was constructed similar to FIG. 2 using the "black and white" method to calculate the weight parameters as explained herein. Similarly to the description of the Wnt (pseudo-)linear model based on the evidence curated list, the weights associated with the edges between probesets and their respective genes, both the evidence curated list and the broad literature list, were trained using continuous fRMA processed data of 32 normal colon samples and 32 adenoma samples from data set GSE8671 from the Gene Expression Omnibus (accessible at http://www.ncbi.nlm.nih.gov/geo/, last accessed Jul. 13, 2011).

The trained (pseudo-)linear models were then tested on various data sets to infer the activity score of the Wnt pathway. The Wnt pathway is designated to be "on", i.e., active, when the activity level is positive. Summarized results of the trained broad literature model and the evidence curated model are shown in FIGS. 21-25.

Evidently, it could be deduced that the broad literature model generally predicts more extreme activity scores for Wnt signaling being on or off. In addition, the alternative model predicts similar results for the colon cancer data sets (GSE20916, GSE4183, GSE15960), but more than expected samples with predicted active Wnt signaling in breast cancer (GSE12777) and medulloblastoma sample (GSE10327) data sets.

In conclusion, the broad literature target genes list results in approximately equally well predictions of Wnt activity in colon cancer on the one hand, but worse predictions (more false positives) in other cancer types on the other hand. This might be a result of the alternative list of targets genes being too much biased towards colon cells specifically, thus too tissue specific; both de Sousa E Melo et al. and Hatzis et al. main interest was colorectal cancer although non-colon-specific Wnt target genes may be included. In addition, non-Wnt-specific target genes possibly included in these lists may be a source of the worsened predictions of Wnt activity in other cancer types. The alternative list is likely to contain more indirectly regulated target genes, which probably makes it more tissue specific. The original list is tuned towards containing direct target genes, which are most likely to represent genes that are Wnt sensitive in all tissues, thus reducing tissue specificity.

EXAMPLE 4

Training and Using the Mathematical Model

Before the (pseudo-)linear models as exemplary described herein can be used to infer pathway activity in a test sample the weights indicating the sign and magnitude of the correlation between the nodes and a threshold to call whether a node is either "absent" or present" need to be determined. One can use expert knowledge to fill in the weights and threshold a priori, but typically models are trained using a representative set of training samples, of which preferably the ground truth is known. E.g. expression data of probesets in samples with a known present transcription factor complex (=active pathway) or absent transcription factor complex (=passive pathway). However, it is impractical to obtain training samples from many different kinds of cancers, of which it is known what the activation status is of the pathway to be modeled. As a result, available training sets consist of a limited number of samples, typically from one type of cancer only. Herein a method is described to determine the parameters necessary to classify test samples as having an active or passive pathway.

Known in the field are a multitude of training algorithms (e.g. regression) that take into account the model topology and changes the model parameters, here weight and threshold, such that the model output, here weighted linear score, is optimized. Herein we demonstrate two exemplary methods that can be used to calculate the weights directly from the expression levels without the need of an optimization algorithm.

Preferably, the training of the (pseudo-)linear models of the Wnt, ER, HH and AR pathways is done using public data available on the Gene Expression Omnibus (accessible at http://www.ncbi.nlm.nih.gov/geo/, cf. above).

The first method, defined here as "black and white"-method boils down to a ternary system with the weighting factors being an element of $\{-1, 0, 1\}$. If we would put this in the biological context the −1 and 1 corresponds to genes or probes that are down- and upregulated in case of pathway activity, respectively. In case a probe or gene cannot be statistically proven to be either up- or downregulated, it receives a weight of 0. Here we have used a left-sided and right-sided, two sample t-test of the expression levels of the active pathway samples versus the expression levels of the samples with a passive pathway to determine whether a probe or gene is up- or downregulated given the used training data. In cases where the average of the active samples is statistically larger than the passive samples, i.e. the p-value is below a certain threshold, e.g. 0.3, then the probeset or target gene is determined to be upregulated. Conversely, in cases where the average of the active samples is statistically lower than the passive samples this probeset or target gene is determined to be downregulated upon activation of the pathway. In case the lowest p-value (left- or right-sided) exceeds the aforementioned threshold we define the weight of this probe or gene to be 0.

In another preferred embodiment, an alternative method to come to weights and threshold(s) is used. This alternative method is based on the logarithm (e.g. base e) of the odds ratio, and therefore called "log odds"-weights. The odds ratio for each probe or gene is calculated based on the number of positive and negative training samples for which the probe/gene level is above and below a corresponding threshold, e.g. the median of all training samples (equation 3). A pseudo-count can be added to circumvent divisions by zero (equation 4). A further refinement is to count the samples above/below the threshold in a somewhat more probabilistic manner, by assuming that the probe/gene levels are e.g. normally distributed around its observed value with a certain specified standard deviation (e.g. 0.25 on a 2-log scale), and counting the probability mass above and below the threshold (equation 5).

Alternatively, one can employ optimization algorithms known in the field such as regression to determine the weights and the threshold(s) of the (pseudo-)linear models described herein.

One has to take special attention to the way the parameters are determined for the (pseudo-)linear models to generalize well. Alternatively, one can use other machine learning methods such as Bayesian networks that are known in the field to be able to generalize quite well by taking special measures during training procedures.

Preferably, the training of the (pseudo-)linear models of the Wnt, ER, HH and AR pathways is done using public data available on the Gene Expression Omnibus (accessible at http://www.ncbi.nlm.nih.gov/geo/). The models were exemplary trained using such public data.

Figure 5:
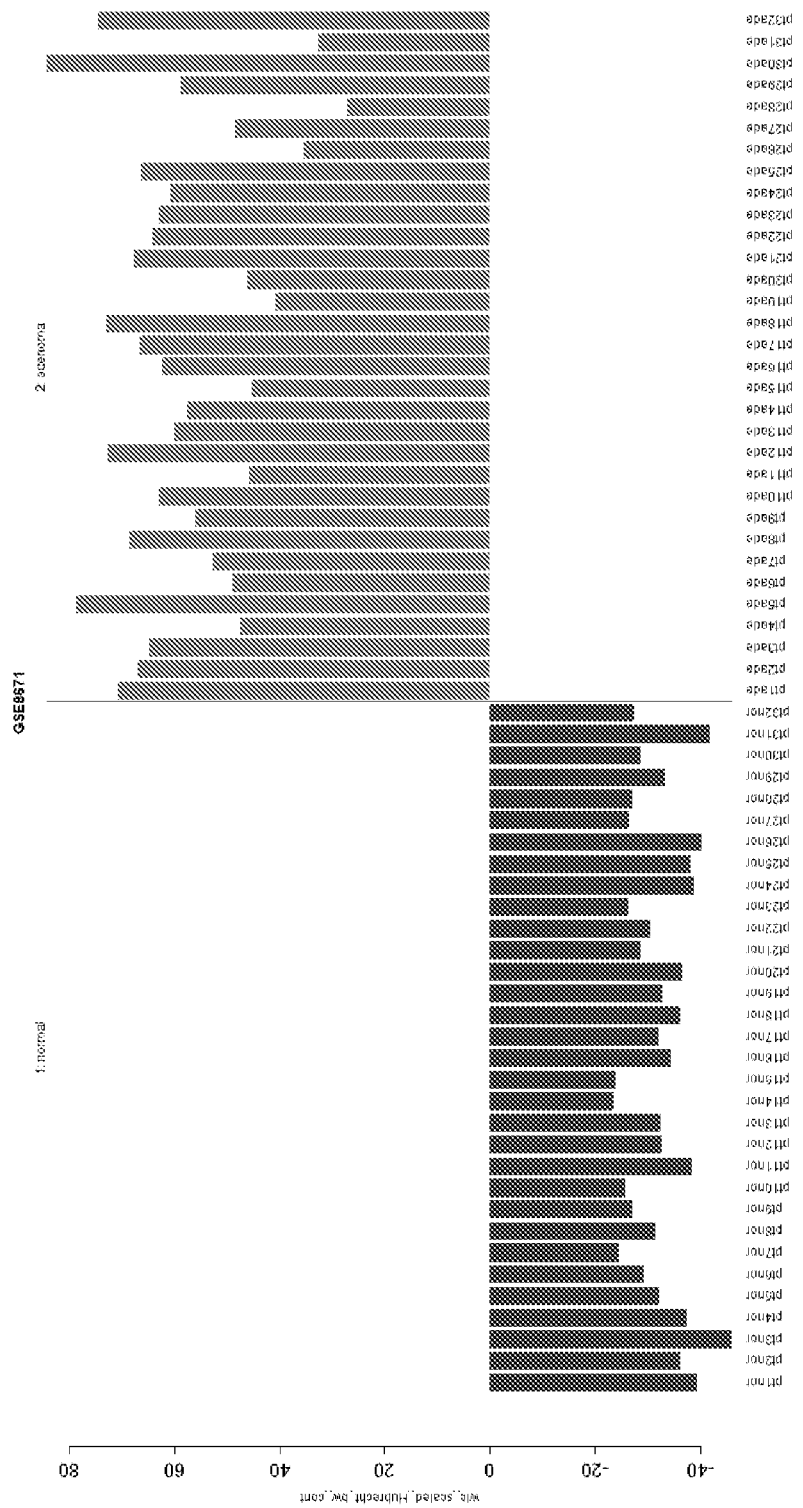

FIG. 5 shows the calculated (pseudo-)linear combination on the training data set GSE8671 using a (pseudo-)linear model as depicted in FIG. 2 for the Wnt pathway and including "all probesets" as mentioned in Table 1. The weights applied to the (pseudo-) linear model were calculated using the "black and white"-method as described herein. The left group represent the samples in which Wnt is known to be passive, whereas the right group shows the calculated activity scores of adenomas samples that are known to have an active Wnt pathway.

Figure 8:
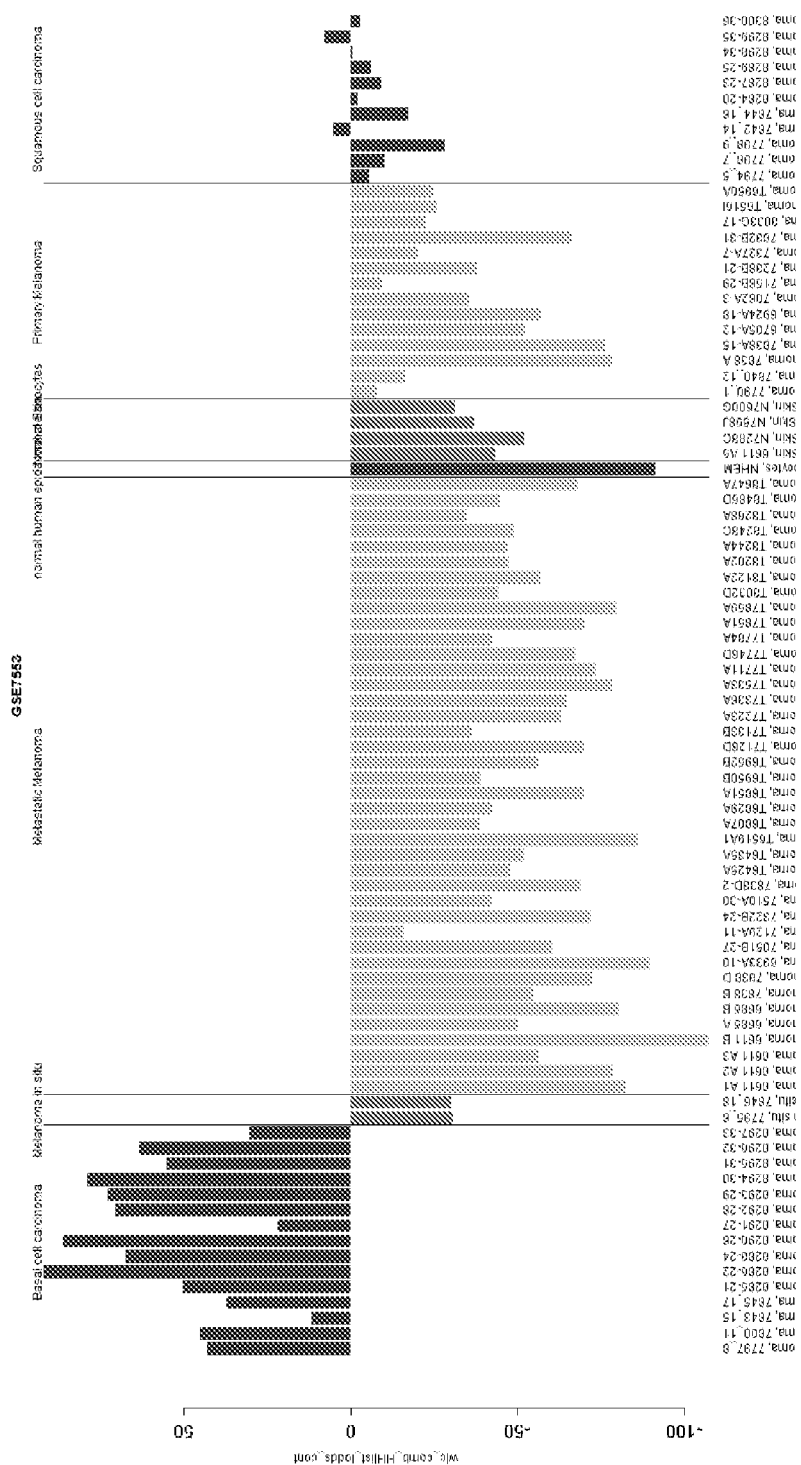

With reference to FIG. 8, the "two-layer" model of the HH pathway using all the probesets and target genes mentioned in Table 3 on the first and second layer, respectively, was trained using continuous expression levels data of basal cell carcinoma samples (first group) known to express HH activity and normal skin cells known to have a passive HH pathway. The training encompassed calculating the weights of the connections between the target genes expression levels, here represented by means of probeset intensities, and the target genes nodes using the "log odds"-method as described herein and subsequently the activity score of the transcription factor complex was calculated by summation of the calculated target genes expression score multiplied by either 1 or −1 for upregulated or downregulated target genes, respectively.

Figure 10:
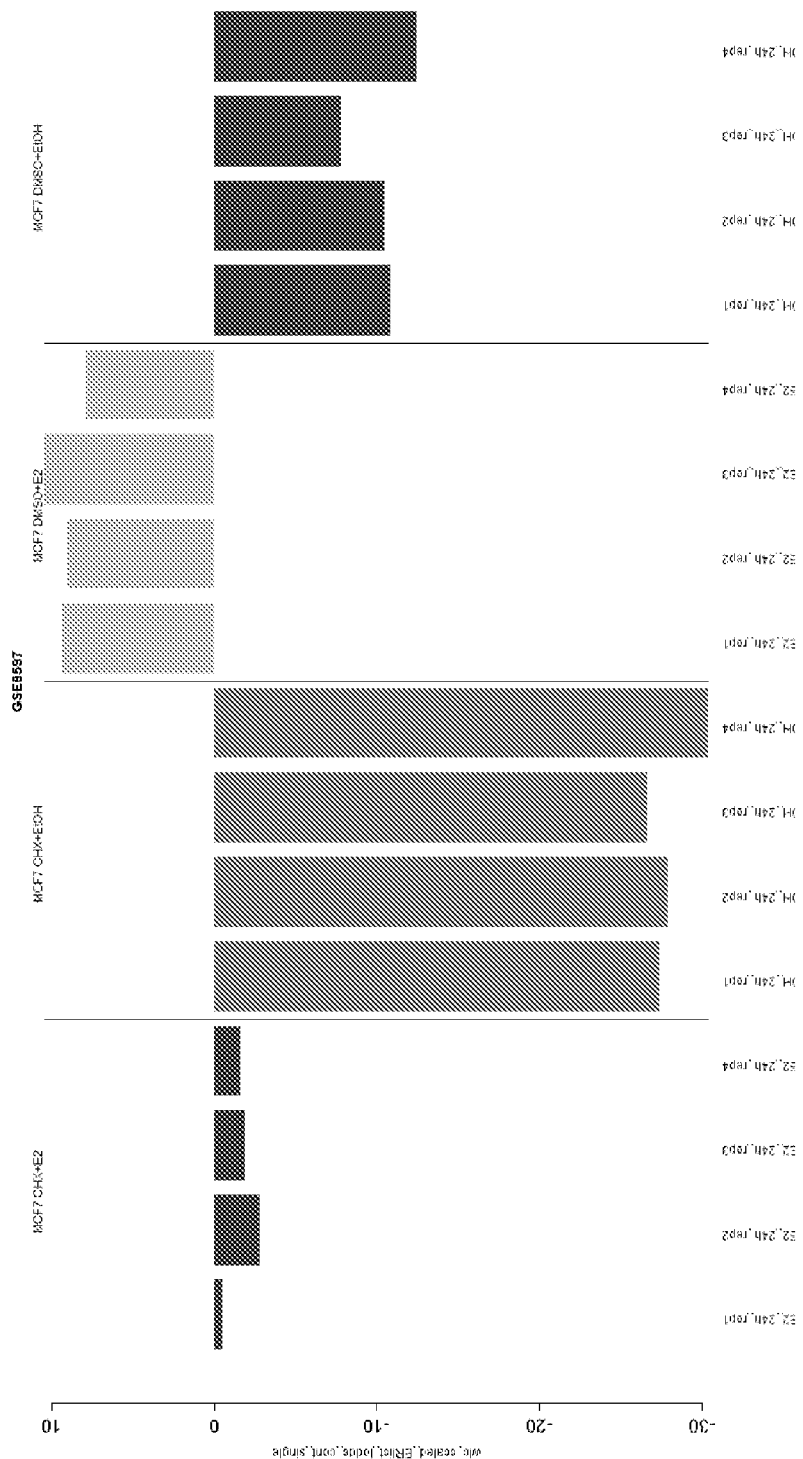

FIG. 10 shows the training results of the simple (pseudo-) linear model of the ER pathway using continuous expression levels measured in stimulating experiments in MCF7 cell lines. The model only included the "most discriminative probeset" per target gene as depicted in Table 2. The "log odds"-method was used in combination with the active ER pathway samples (third group from the left, MCF7 cells stimulated with E2, a potent ER activator) and passive ER pathway samples (fourth group, MCF7 cells treated with a control) to come to the weights necessary to calculate the ER activity score plotted on the vertical axis.

Figure 13:
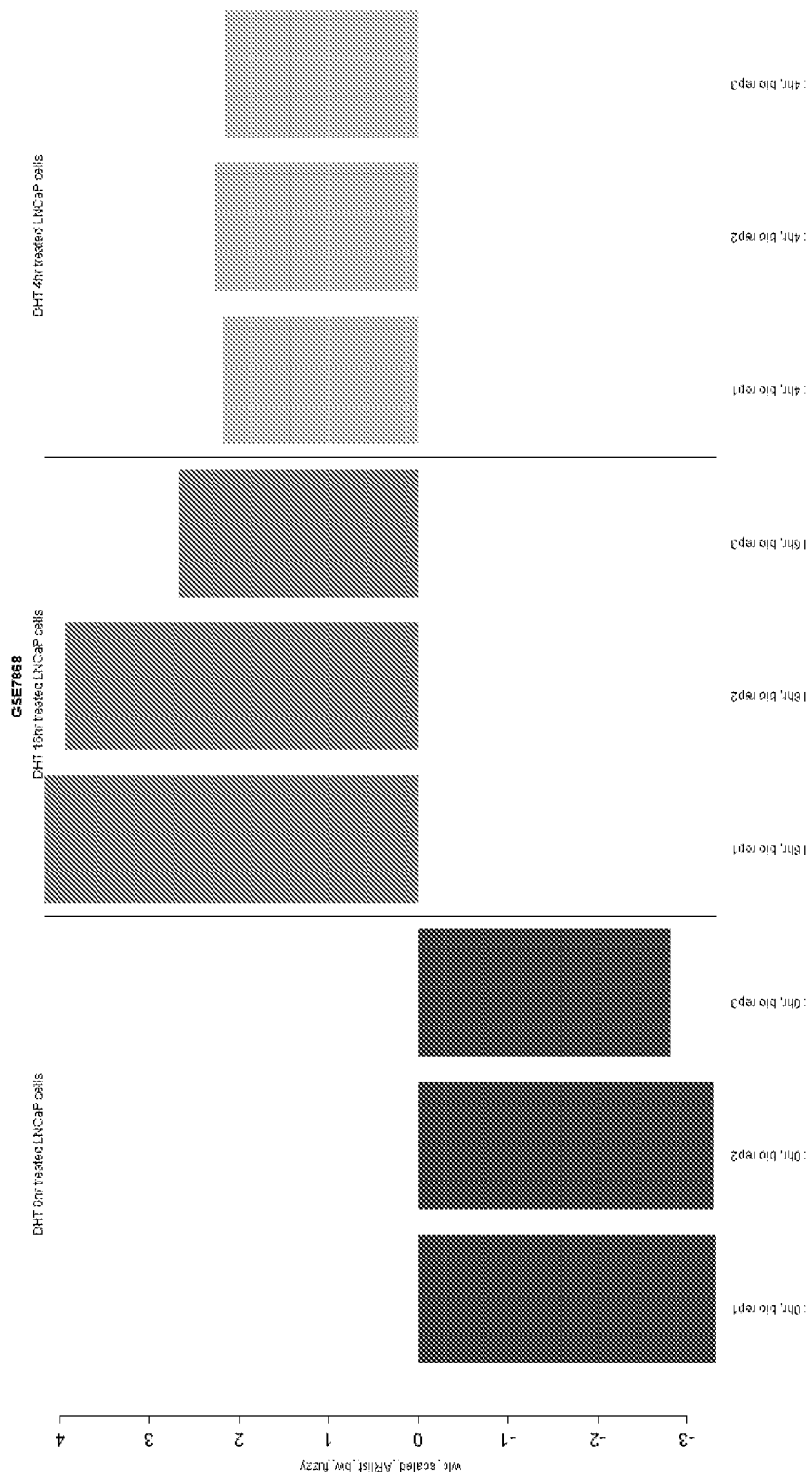

With reference to FIG. 13, a (pseudo-)linear model as depicted in FIG. 2 of the AR pathway was exemplary trained with the aforementioned "black and white" method using 3 samples with positive AR activity, LNCaP cell lines stimulated with Dihydrotestosterone (DHT), a potent AR pathway activator, and 3 non-stimulated LNCaP cell lines representing the inactive AR pathway case. The expression data of these stimulation experiments are publically available in the GSE7868 dataset that has been fuzzy transformed as described herein. "All probesets" of the selected AR target genes mentioned in Table 4 have been used in this particular example. The result of the training is shown in FIG. 13. The 1st and 2nd group of samples from the left has been used as negative and positive training samples, respectively. As expected, the control within the experiment, stimulation of LNCaP with DHT for 4 hours demonstrates AR activity, albeit lower activity levels than the cells stimulated for 16 hours.

Figure 6:
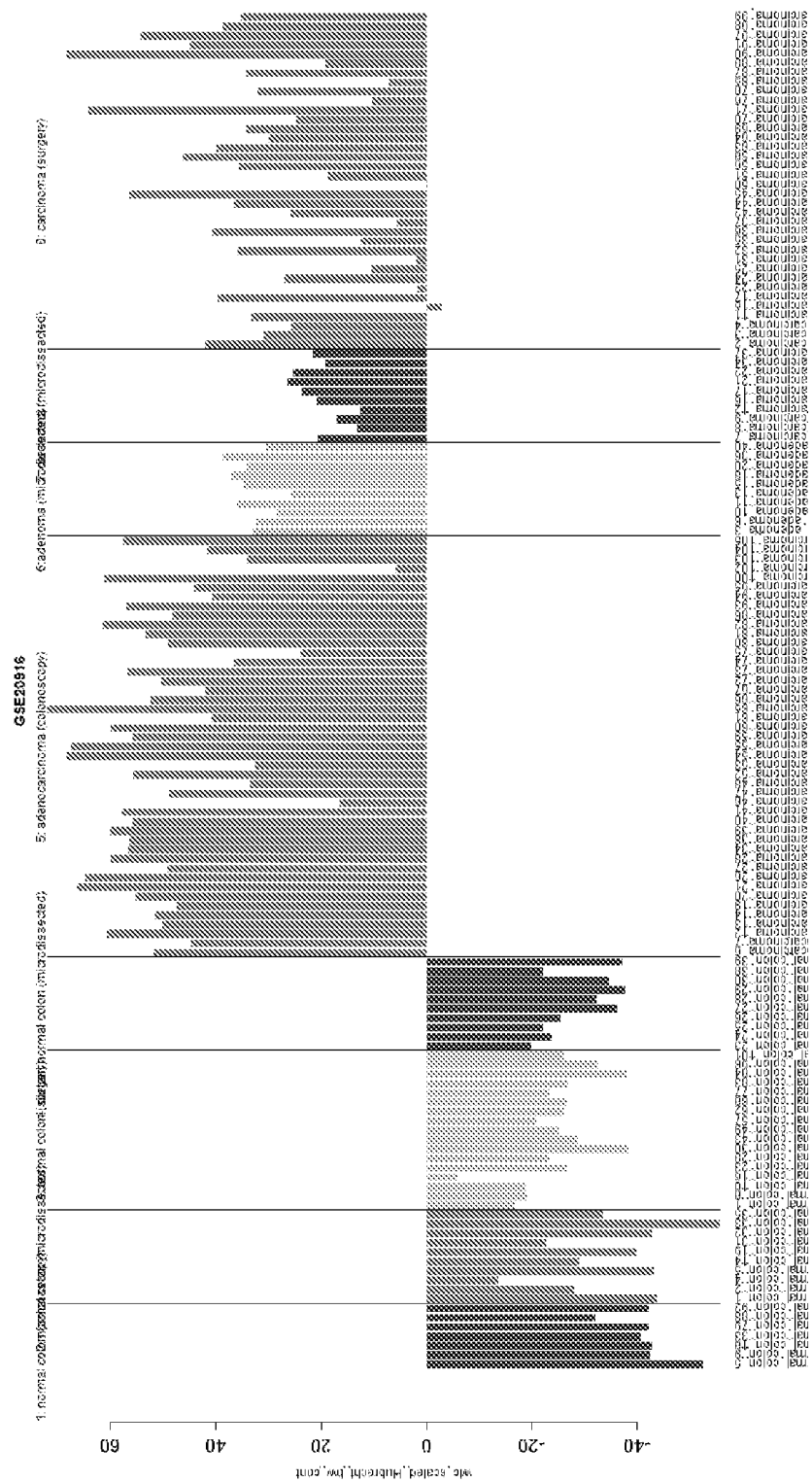
Figure 17:
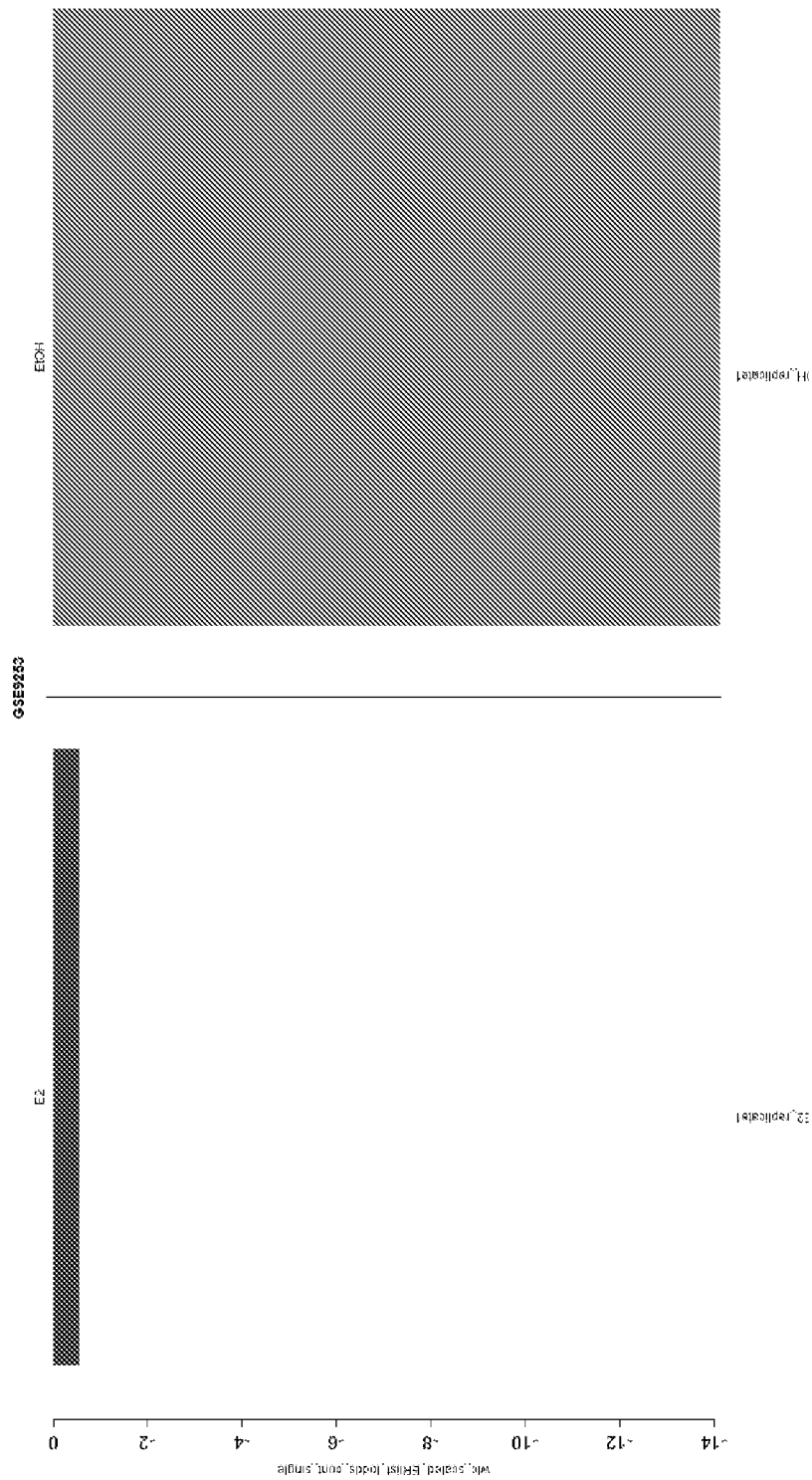

With reference to FIG. 6 and FIG. 17, the trained (pseudo-)linear models of the Wnt and ER pathway were used to predict the pathway activities in similar samples (colon samples and MCF7 breast cancer cell line for the Wnt and ER Bayesian network, respectively) not used in the training procedure as described herein (no appropriate data set for the HH and AR (pseudo-)linear models were available). The predicted pathway activities of the vast majority of the samples should be in line with the clinically expected pathway activities for the model to be validated.

FIG. 6 shows the calculated Wnt activities, depicted as the calculated activity score on the vertical axis, for the samples, illustrated by the bars on the horizontal axis, of the colon samples grouped by classification, indicated by the bar's color, in the GSE20916 data set. All normal colon samples are rightfully predicted to have an inactive pathway (score <0), based on it being a sample of healthy tissue. All but one sample, a carcinoma sample in the last group, alleged to have an active pathway are predicted to have an active Wnt pathway.

In FIG. 17 the validation results of the trained ER (pseudo-)linear model is shown for two microarrays measured using a MCF7 breast cancer cell line sample, one stimulated with estradiol (E2) the other one with a negative control (EtOH), originating from the GSE9253 data set. The difference in ER activity score is evident from FIG. 17. However the E2-stimulated sample was predicted to have a slightly negative ER activity score. This is the result of the threshold defining either an active or passive state was set too high for this particular experiment. The reason for this discrepancy could be that in this experiment a different stimulation regime was applied; in the training data set (GSE8597) the samples were treated 8 times longer (24 hours instead of 3 hours) with a four times lower concentration of E2 (100 nM vs 25 nM). It is known from the art that in general expression of target genes is more optimal after 24 hours of treatment with a stimulating agent than after only 3 hours, which can explain the lower ER activity score in the stimulated MCF7 sample in this data set. The negative control properly predicts the ER pathway to be inactive.

Further details and examples for using trained (pseudo-) linear models (e.g. of Wnt, ER, AR and HH pathway) to predict the respective pathway activities are explained in Example 6 below.

The above mentioned training process can be employed to other (pseudo-)linear models of clinical applications. Here it is shown and proven to work for the exemplary (pseudo-)linear models constructed using herein disclosed method representing cellular signaling pathways, more specifically the Wnt, ER, AR and HH pathways.

EXAMPLE 5

Diagnosis of (Abnormal) Pathway Activity

The following will exemplary illustrate how to use e.g. the (pseudo-)linear models to diagnose the activity of a cellular signaling pathway.

Figure 7:
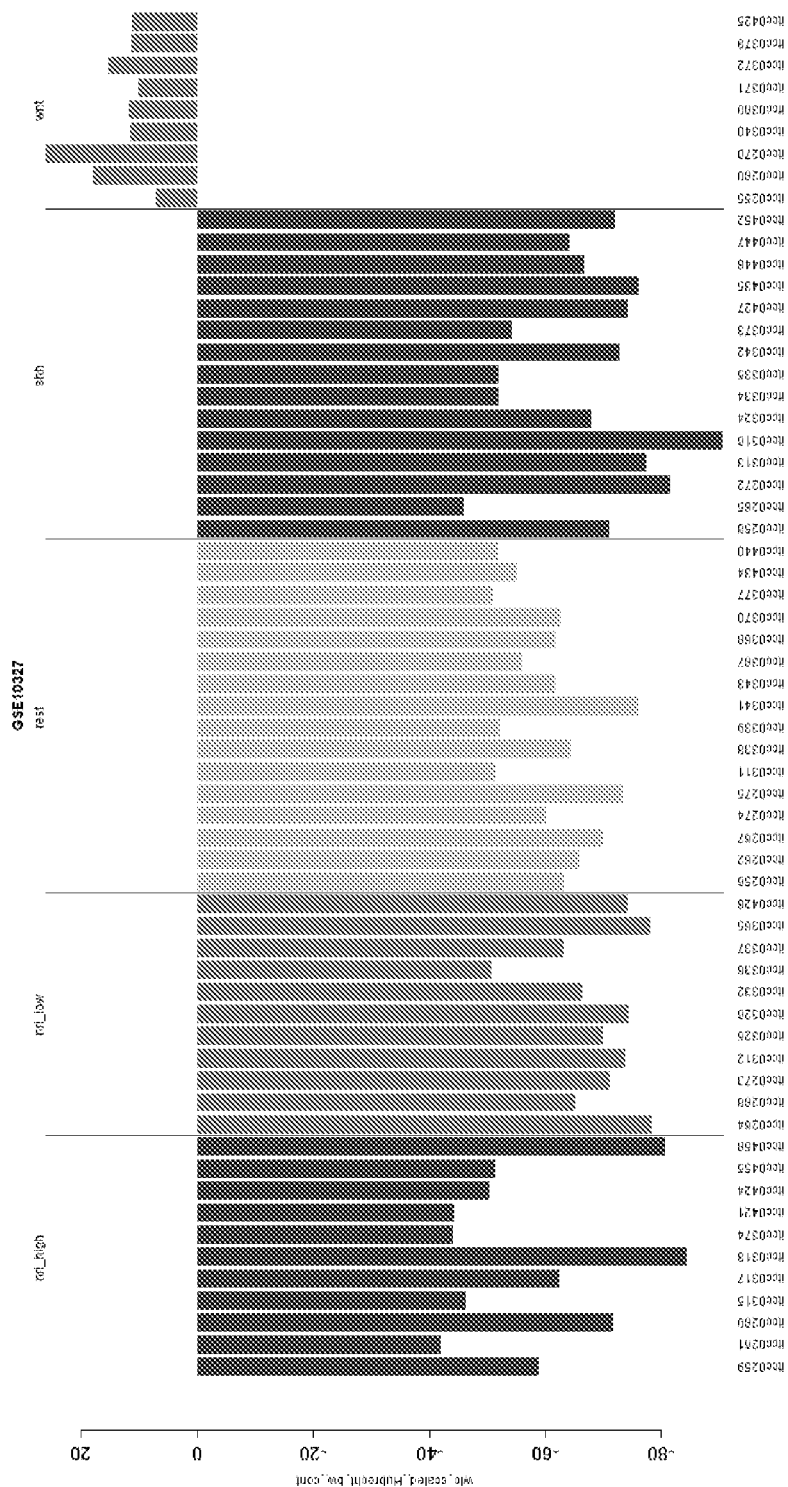

The exemplary (pseudo-)linear model of the Wnt consists of a node representing the transcription factor complex, the exemplary selected readout for pathway activity, and "all probesets" mentioned in Table 1 feeding into the transcription factor complex node is trained as described herein, was used to predict the Wnt pathway activity score and it state, active or passive, in various, previously not used for training, data sets to infer how well the trained (pseudo-)linear model operates. The predicted pathway activity scores and associated activity calls calculated for a set of medulloblastoma cancer samples (GSE10327, see FIG. 7) are correlated with clinical knowledge known about the clinical samples. The exemplary trained (pseudo-)linear model is able to predict all Wnt positive medulloblastoma samples to have a slightly active Wnt pathway. All Wnt positive samples have a relatively low Wnt score compared to all other Wnt negative samples, which can be an indication that in medulloblastoma samples the threshold, defined in colon tissue samples, should be lower than in colon samples, possibly due to tissue-specific differences in gene expression.

Figure 9:
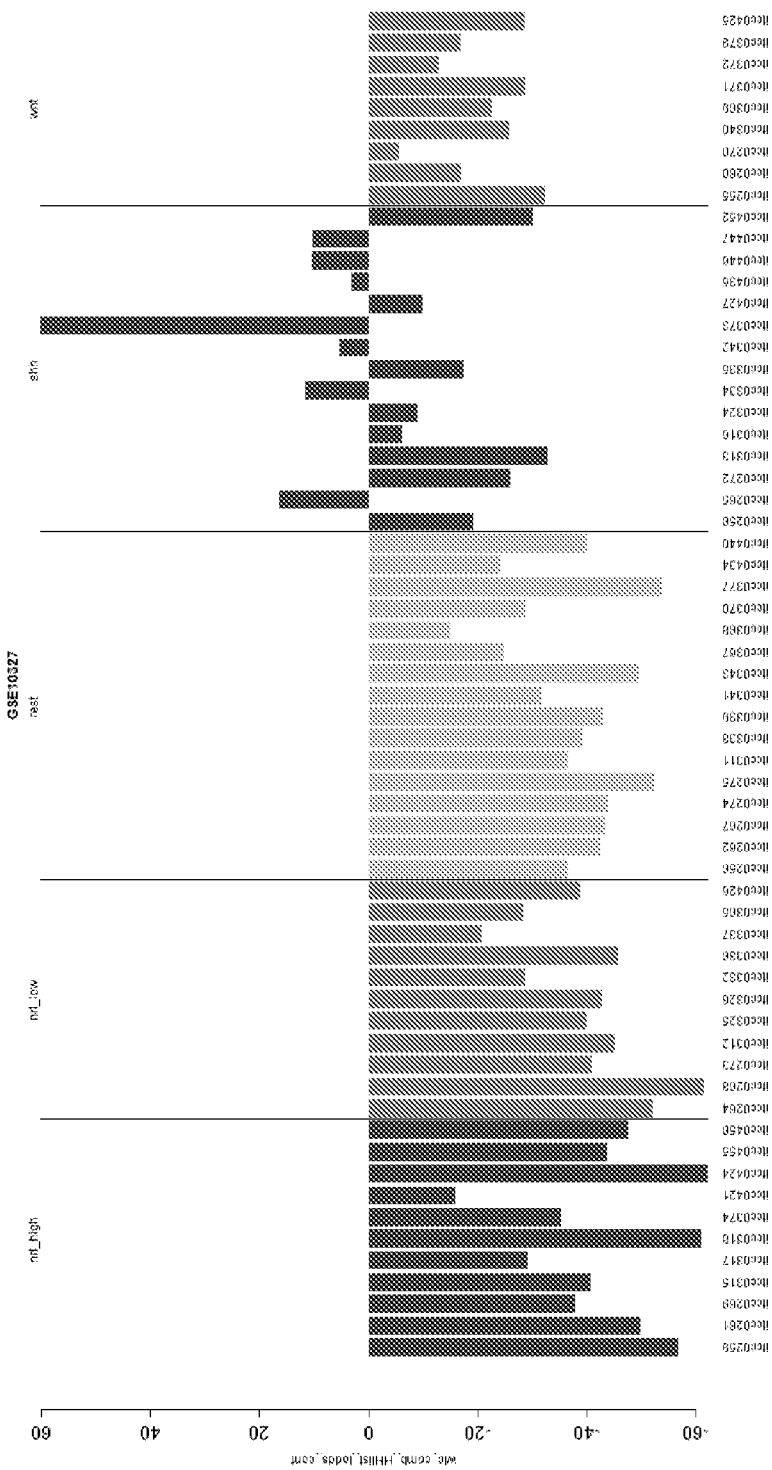

The exemplary trained (pseudo-)linear model of the HH pathway consisting of two-layers, with all the probesets and target genes mentioned in Table 3 on the first and second layer, respectively was used to predict the HH activity in a set of medulloblastoma cancer samples (GSE10327, see FIG. 9). The HH activity score is calculated based on the target genes expression score based on the method described herein. Half of the samples in the HH positive group as indicated by shh in FIG. 9 are correctly predicted by the model to have an active HH pathway. All other samples were correctly predicted to have an inactive HH pathway.

Figure 11:
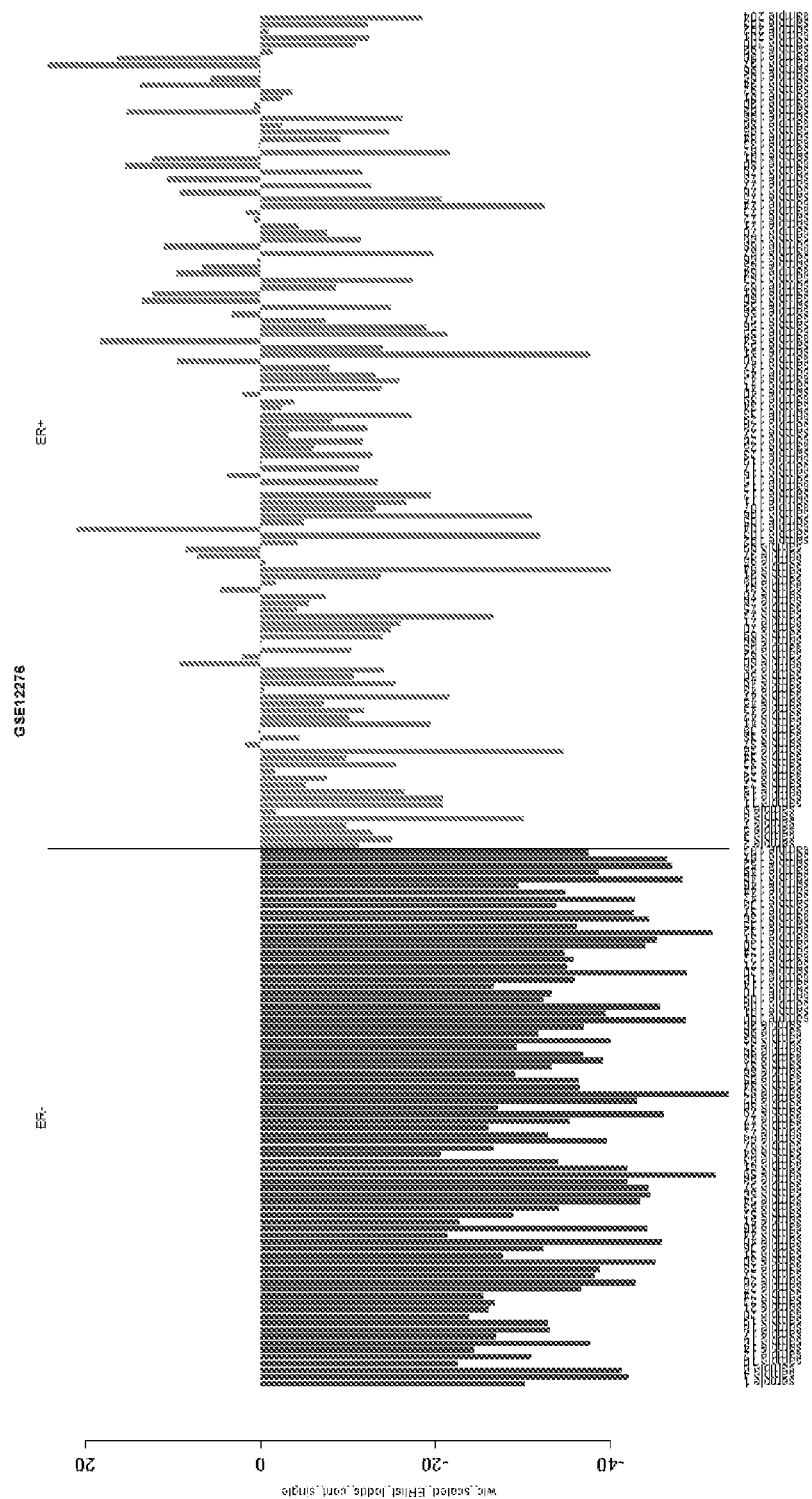

The exemplary trained (pseudo-)linear model of the ER pathway based on the "most discriminative probesets" and the "log odds" as depicted in Table 2 as described herein was used to predict the ER pathway activity score in a set of breast cancer samples of the GSE12276 data set. The resulting ER pathway activity scores are shown in FIG. 11. The breast cancer samples are grouped together in expressing ER (ER+) or not expressing ER (ER−). The ER status is determined based on the expression level of ER measured by the microarray experiment. Although a clinical sample might express high levels of ER this does not necessarily mean that the ER pathway is active. This is also supported by the relative high ineffective hormonal treatment in ER+ breast cancer of 50-60%. On the other hand, it is known from the field that the ER pathway cannot be active when a clinical sample does not express ER. Approximately 25% of the ER+ samples are predicted by the (pseudo-)linear model to have an active ER pathway which can partly be explained by the relative high ineffective hormonal treatment in these types of breast cancers of 50-60%. The ER pathway is predicted correctly to have a passive ER pathway in the ER− samples.

Figure 15:
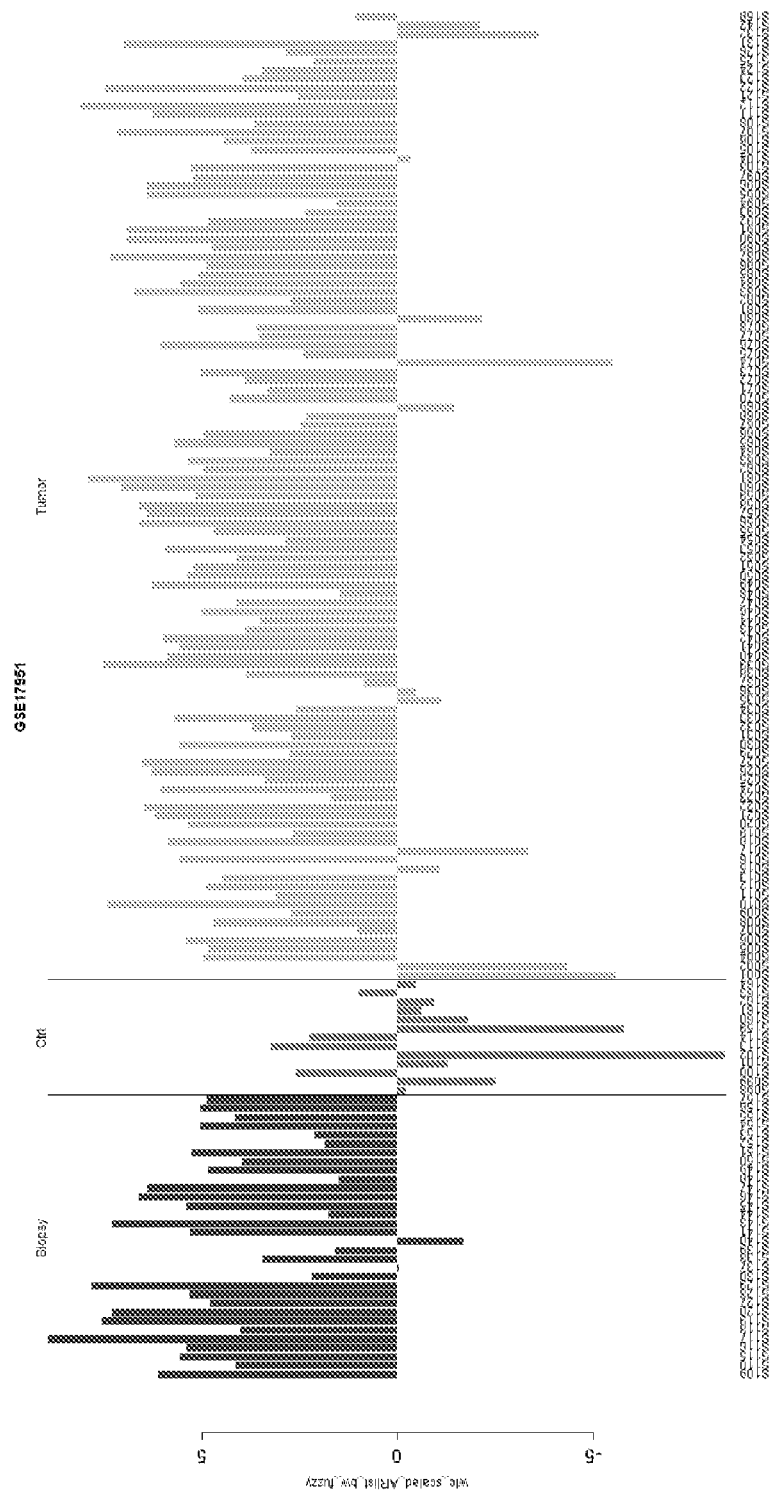

The exemplary trained AR (pseudo-)linear model based on "all probesets" mentioned in Table 4 and weights calculated using the "black and white"-method and fuzzy transformed expression data of LNCaP cells (GSE7868) as described herein was used to predict the activity of the AR pathway in prostate samples (GSE17951, fuzzy transformed). The calculated AR activity scores for the three groups of samples (from left to right: biopsy, control and tumor) are shown in FIG. 15. The vast majority of the biopsy and tumor samples were found to have a high AR activity, which seems to correlate with the known clinical state. On the other hand a relative low number of samples in the control group express AR activity according to the model predictions as expected.

EXAMPLE 6

Prognosis Based on Pathway Activity

Figure 16:
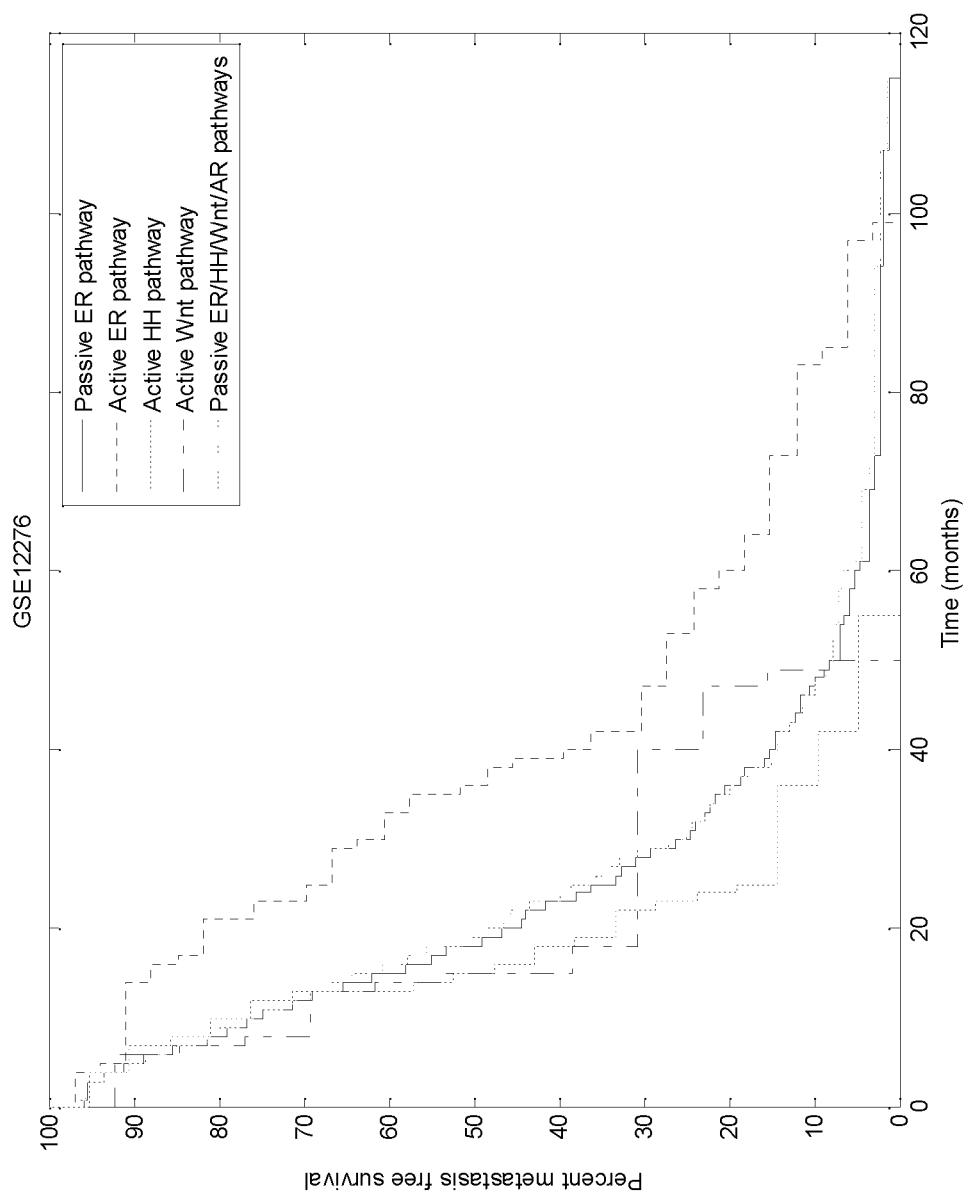

Early developmental pathways, like Wnt and HH, are thought to play a role in metastasis caused by cancer cells which have reverted to a more stem cell like phenotype, called cancer stem cells. Indeed, sufficient evidence is available for the early developmental pathways, such as Wnt pathway, to play a role in cancer metastasis, enabling metastatic cancer cells to start dividing in the seeding location in another organ or tissue. Metastasis is associated with bad prognosis, thus activity of early developmental pathways, such as the Wnt and HH pathway, in cancer cells is expected to be predictive for bad prognosis. This is supported by the fact that breast cancer patients, from the GSE12276 data set, that were identified having an active ER pathway but not having an active Wnt or HH pathway using the (pseudo-)linear models described herein had a better prognosis than patients identified having either an active HH or Wnt pathway or both, as illustrated by the Kaplan-Meier plot in FIG. 16.

EXAMPLE 7

Therapy Planning, Prediction of Drug Efficacy, Prediction of Adverse Effects and Monitoring of Drug Efficacy The following exemplary illustrates how to use (pseudo-)linear models of cellular signaling pathways for therapy planning, prediction of drug efficacy, monitoring of drug efficacy and related activities.

Figure 12:
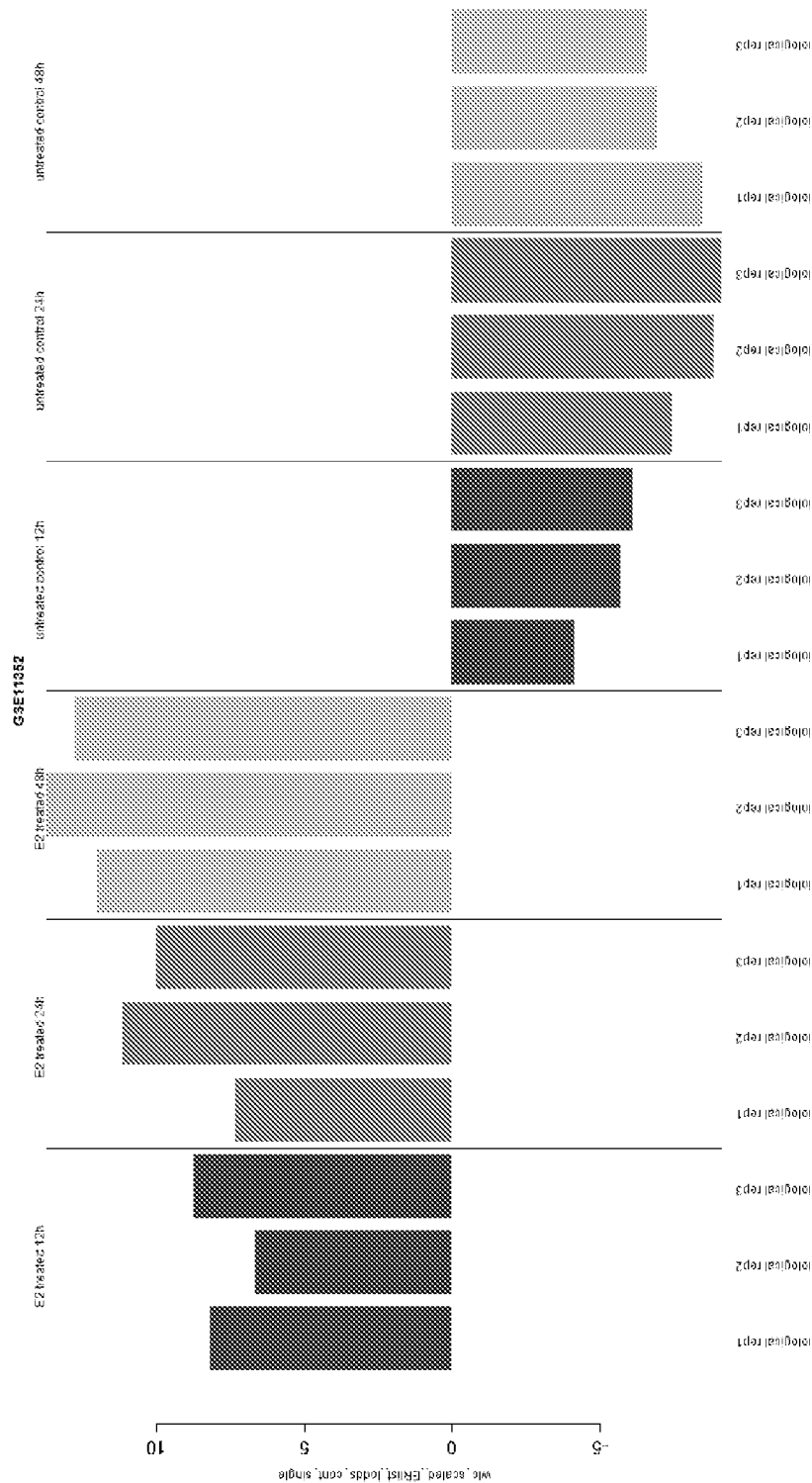

The (pseudo-)linear model of the ER pathway, constructed using a node for the transcription factor presence and a layer of probesets (Table 2) associated with the target genes of the ER pathway, analogous to FIG. 2 as described herein, and trained as described herein, was used to calculate the ER pathway activity score. The pathway activity score is subsequently demonstrated to be correlated with drug efficacy or monitoring drug efficacy. Result summaries are shown in FIGS. 20 and 12.

With respect to FIG. 20, Tamoxifen is a drug currently used for the treatment of ER+ (estrogen receptor positive) breast cancer. It acts as a partial antagonist of the estrogen receptor inhibiting the uncontrolled cell proliferation which is thought to be induced by ER signaling. Unfortunately, not every breast cancer responds to treatment with Tamoxifen, despite the demonstration of the presence of ER protein in cancer cells by routine histopathology analysis of cancer tissue slides. Many studies have been conducted to investigate this so-called Tamoxifen resistance. The publicly available GSE21618 data set is the result of one of such study and contains microarray data of Tamoxifen resistant and wild-type MCF7 cell lines under different treatment regimes. The ER (pseudo-)linear model constructed and trained as described herein is used to analyze the Tamoxifen resistant and wild type MCF7 cell lines under different treatment regimes, the results are depicted in FIG. 20.

The control Tamoxifen resistant cell line, indicated by TamR.Ctrl, is predicted to have an inactive ER pathway for every time point after Tamoxifen addition (1, 2, 3, 6, 12, 24, and 48 h). It is not surprising that treatment of the Tamoxifen resistant cell line stimulated with E2 and treated with Tamoxifen, indicated by TamR.E2_Tam (fourth group), is ineffective, which is also illustrated by the predicted inactivity of the ER pathway for this group over the same time points. According to analysis of the Tamoxifen resistant cell line (TamR.Ctrl) the driving force of the uncontrolled cell proliferation is not due to active ER signaling; therefore treating it with an ER antagonist will not inhibit cell proliferation. This illustrates that treatment with Tamoxifen is not recommended in case of a negative predicted ER pathway activity.

On the other hand, the wild type MCF7 cell line, known to be Tamoxifen sensitive, treated with 17beta-estradiol (wt1.E2, eleventh group) slowly reacts to the hormone treatment which is visible in the increasing ER positive activity predictions. Treating such a cell line with ER inhibitors such as Tamoxifen will inhibit the ER pathway which is illustrated by the decreasing ER pathway activity score in time of the MCF7 samples stimulated with E2 and treated with Tamoxifen (wt2.E2_Tam, twelfth group).

In another example, a publically available data set of MCF7 cell lines stimulated with or deprived of ER stimulating agent (E2) with expression levels measured at 12 hours, 24 hours and 48 hours after starting stimulation or deprivation (GSE11352) was used to calculate the ER activity scores using the trained ER (pseudo-)linear model as described herein. The ER pathway activity score increases for longer exposure times to the ER stimulating agent (first three groups) and decreases in case of prolonged starvation in the control (last three groups), although prolonged deprivation increases slightly after 48 hours again. With the exception of the starvation of 48 hours, the predicted ER activity scores nicely correlates with the knowledge that prolonged stimulation result in higher ER activity and vice versa. Inversely, this example implies that the ER activity score can be used to monitor efficacy or inefficacy of stimulation or inhibition of ER activity treatments.

EXAMPLE 8

Drug Development

Similar to therapy response monitoring, a pathway model can be used in drug development to assess the effectiveness of various putative compounds. For instance, when screening many compounds for a possible effect on a certain pathway in a cancer cell line, the respective pathway model can be used to determine whether the activity of the pathway goes up or down after application of the compound or not. Often, this check is done using only one or a few of putative markers of the pathway's activity, which increases the chance of ineffective monitoring of the treatment effect. Furthermore, in follow-up studies on animal or patient subjects, the pathway models can be used similarly to assess the effectiveness of candidate drugs, and to determine an optimal dose to maximally impact pathway activity.

Figure 14:
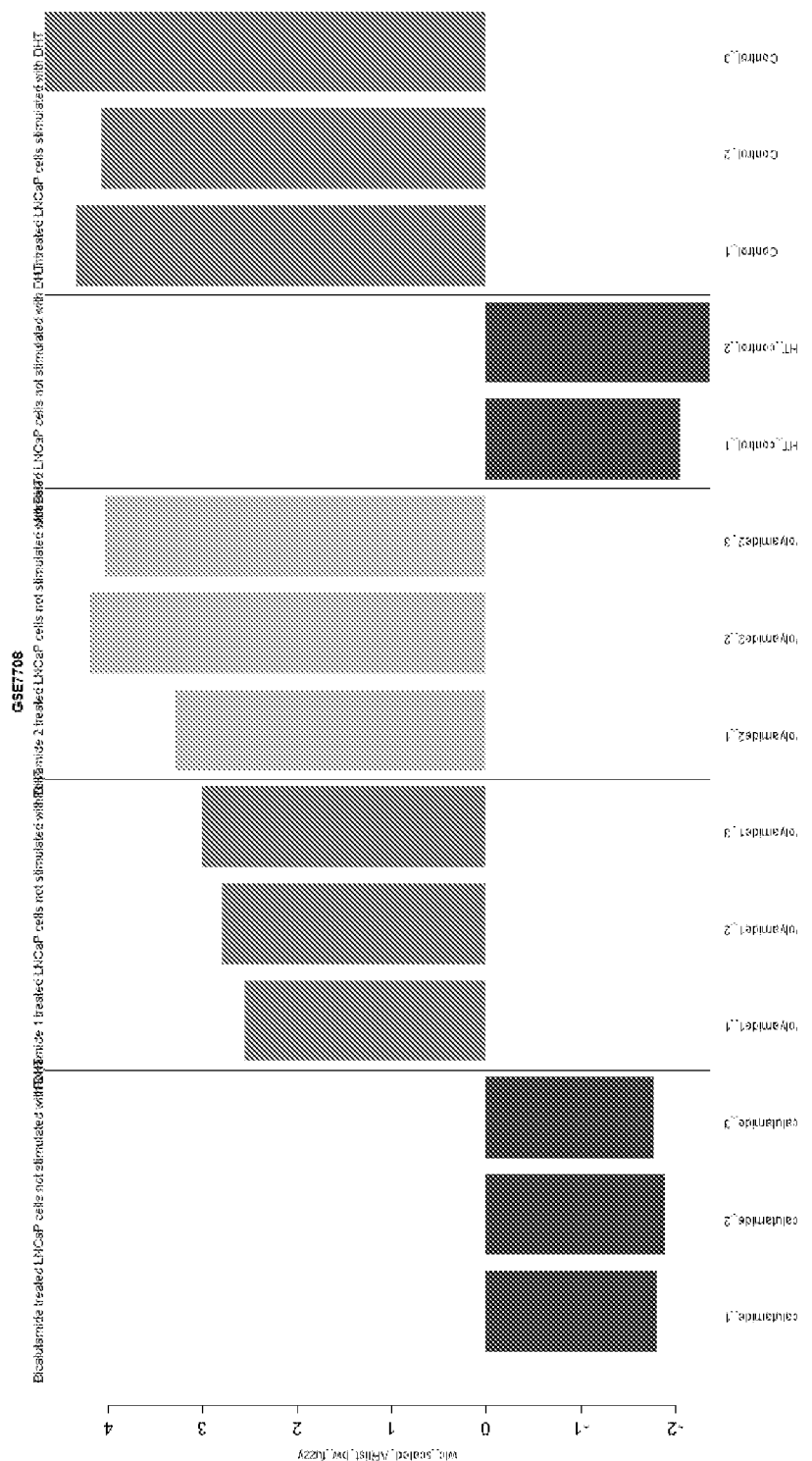

An example of ineffective monitoring of new drug compounds is illustrated by the predicted AR pathway activity in the GSE7708 samples as shown in FIG. 14. In this study two possible drug compounds to inhibit AR pathway activity, denoted by Polyamide 1 and Polyamide 2, have been developed. It has been demonstrated that these two polyamides are capable to inhibit expression of KLK3 (=PSA) a well-known target gene/marker of the AR pathway as well as 35% of the transcripts that were induced upon DHT stimulation (a known activator of the AR pathway). In contrast, the (pseudo-) linear model of the AR pathway predicted the samples treated first with stimulating agent DHT and subsequently with polyamide 1 (second group in FIG. 14) and polyamide 2 (third group in FIG. 14) to still have an active AR pathway. Investigating the inferred AR activity scores and the measured expression levels of the target genes indicated that KLK3 in contrast to the other target genes was downregulated in accordance to the findings whereas all other target genes (except for AR, GUCY1A3 and TMPRSS2 in case of Polyamide 1) were clearly differentially expressed in the Polyamide 1 and Polyamide 2 treated samples. In other words, only a limited number of target genes for AR activity, in particular their efficacy marker KLK3, was downregulated, whereas the majority of the identified target genes were still upregulated indicating the AR pathway is still largely intact and thus active. By taking into account a larger number of target genes based on literature evidence the inventors were able to show that the inhibition of AR activity of the polyamides is limited and that only KLK3 expression is clearly downregulated using these polyamides. Moreover, this illustrates the value of a systematic approach using a multi-target gene (pseudo-)linear model compared to a reductionist approach in drug development.

EXAMPLE 9

Assay Development

Instead of applying the mentioned (pseudo-)linear models on mRNA input data coming from microarrays or RNA sequencing, it may be beneficial in clinical applications to develop dedicated assays to perform the sample measurements, for instance on an integrated platform using qPCR to determine mRNA levels of target genes. The RNA/DNA sequences of the disclosed target genes can then be used to determine which primers and probes to select on such a platform.

Validation of such a dedicated assay can be done by using the microarray-based (pseudo-)linear models as a reference model, and verifying whether the developed assay gives similar results on a set of validation samples. Next to a dedicated assay, this can also be done to build and calibrate similar (pseudo-)linear models using mRNA-sequencing data as input measurements.

EXAMPLE 10

Pathway Research and Cancer Pathophysiology Research

The following will illustrate how (pseudo-)linear models can be employed in (clinical) pathway research, that is research interested to find out which pathways are involved in certain diseases, which can be followed up for more detailed research, e.g. to link mutations in signaling proteins to changes in pathway activation (measured with the model). This is relevant to investigate the initiation, growth and evolution and metastasis of specific cancers (the pathophysiology).

The (pseudo-)linear models of the Wnt, ER, HH and AR pathway, constructed using at least a node for the transcription factor presence and a layer of nodes representing the target genes' mRNA expression levels as measured by their associated probesets (Table 1, Table 2, Table 3 and Table 4), analogous to FIGS. 2 and 3 described herein, and trained as described herein, were used to predict the pathway activity of a data set consisting of breast cancer samples (GSE12276).

Suppose the researcher is interested in looking into the cellular signaling pathway or pathways and the specific deregulation(s) that drive(s) the uncontrolled cell proliferation. The researcher can analyze the microarray data using the above mentioned (pseudo-)linear models to find which pathways are presumably the cause of uncontrolled cell proliferation. Shown in FIG. 18 and FIG. 19 one can see an illustration of such an analysis for the case of Wnt, ER, AR and HH activity scores (basal and luminal A samples of the GSE12276 data set). Subsequently, the researcher can search in more detail to find the exact cause of pathway deregulation.

Figure 19:
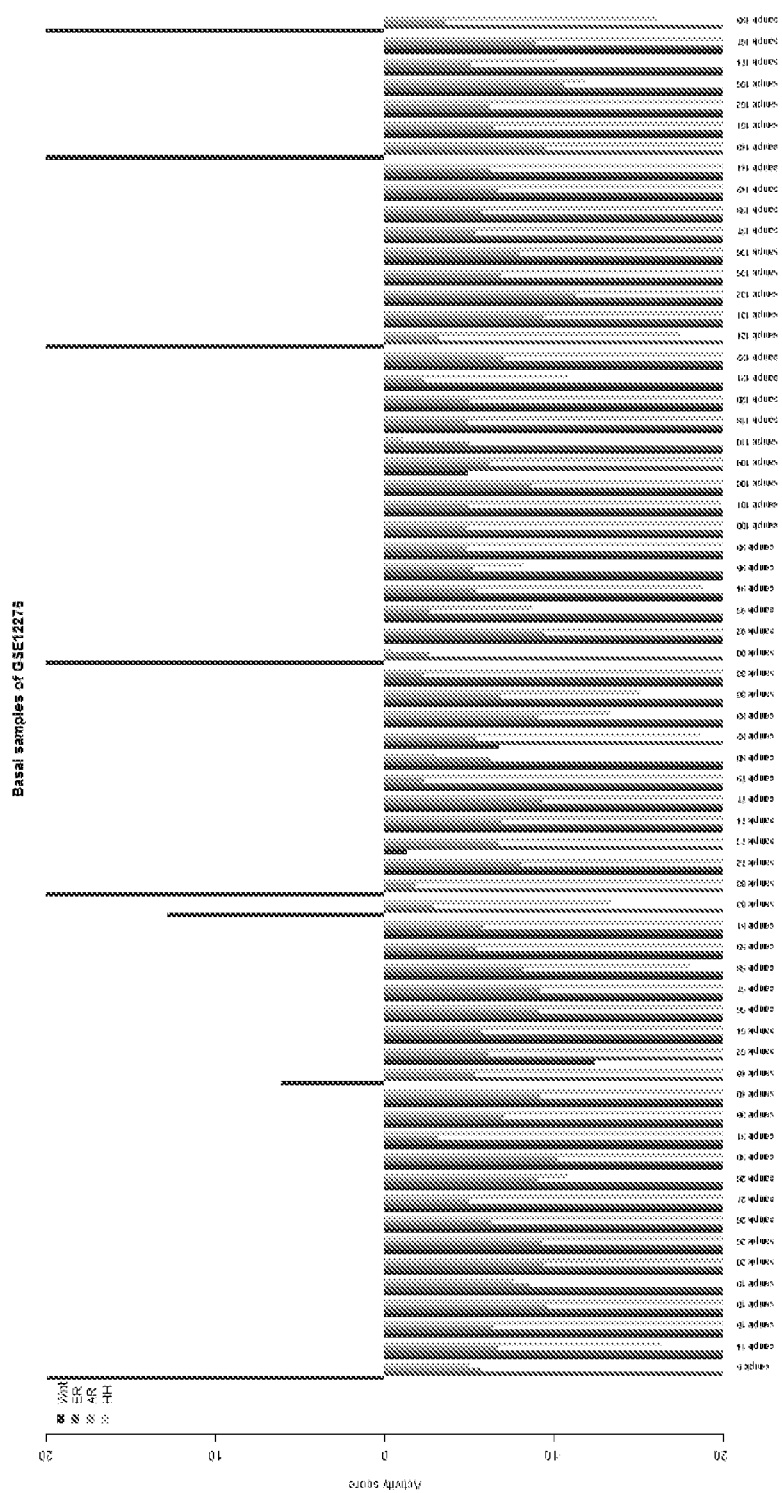
FIG. 19 shows Wnt, ER, AR and HH pathway activity in basal samples of GSE12276.

With reference to FIG. 19, the basal samples are known to have triple negative receptor status (ER, PR and HER2), therefore it is not surprising to see that all samples are predicted to have an inactive ER pathway (see also FIG. 11). On the other hand some of the samples are predicted to have the Wnt pathway active as shown in FIG. 19. These predicted Wnt pathway activities persuade the researcher to investigate these samples in more detail for e.g. known mutations or other known deregulations in the Wnt pathway. This methodology could also be applied to other cellular signaling pathways, such as the HH and AR pathways.

Figure 18:
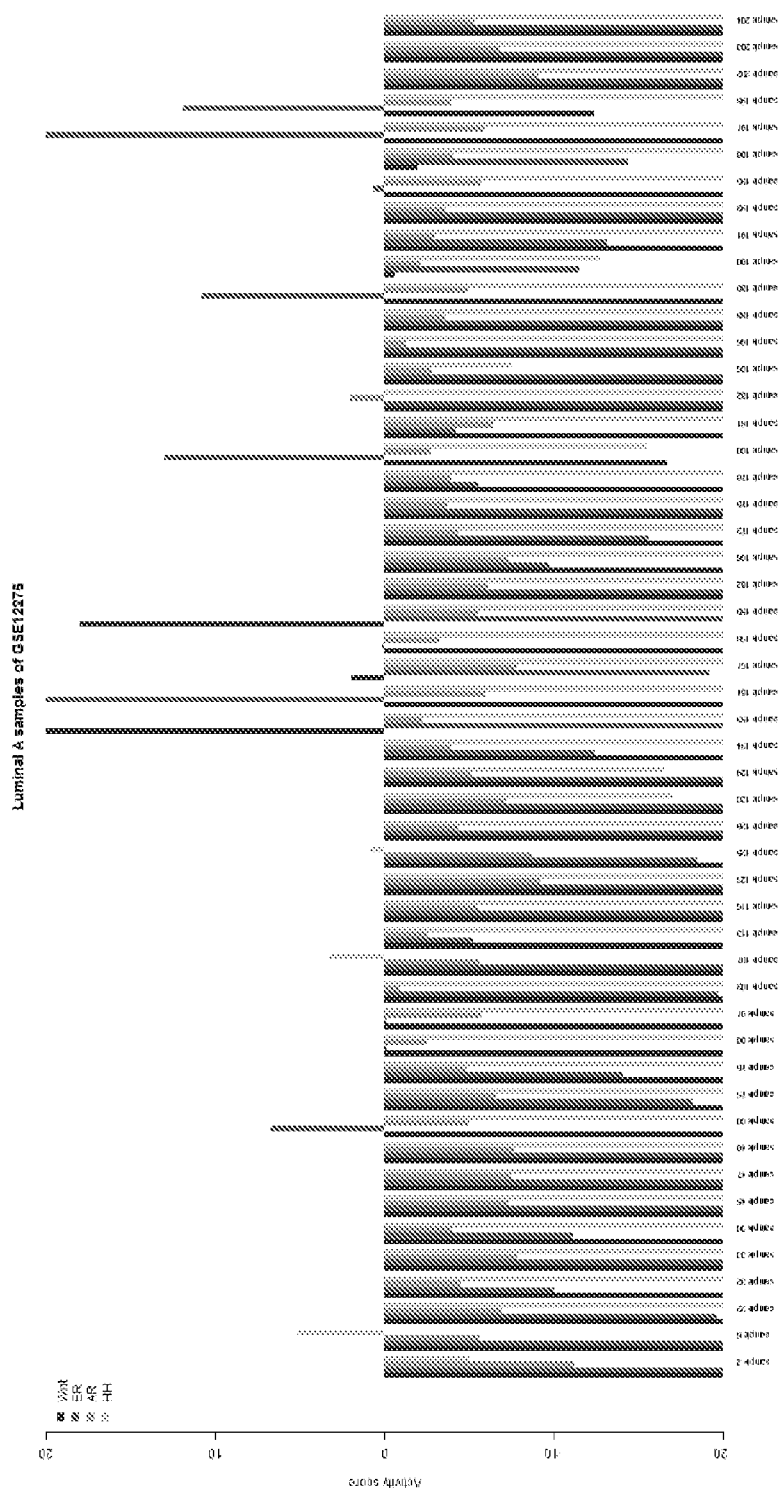
FIG. 18 shows Wnt, ER, AR and HH pathway activity in luminal A samples of GSE12276.

Another example is given in FIG. 18, where the Wnt, ER, AR and HH activity scores in the luminal A samples of the GSE12276 data set are illustrated. Luminal A samples are known to express ER, however this does not necessarily mean the cancerous properties are due to active ER signaling. From the predicted pathway activities one can infer that not every ER+ sample has an active ER signaling. However, some of the samples that do not have an active ER signaling are found to have an active Wnt, AR and/or HH pathway. This might give rise for the researcher to investigate these samples in closer details for defects in the Wnt, AR and/or HH signaling pathway, respectively. Some of the samples do not predict any of the included four pathways being active; maybe other pathways are causing the uncontrolled cell proliferations. Also this gives the researcher additional information to search for defects in other pathways.

In summary, the illustrations described herein indicate the ability of trained (pseudo-)linear models (as described above) to support the process of finding the cause of uncontrolled cell proliferation in a more directed method. By employing the (pseudo-) linear models to screen the samples for pathway activities, the predicted pathway activities can pinpoint the possible pathways for the uncontrollable cell proliferation, which can be followed up for more detailed research, e.g. to link mutations in signaling proteins or other known deregulations to changes in activation (as measured with the model).

As described herein, the process to develop and train a (pseudo-)linear model of cellular signaling pathways can be used to construct a (pseudo-)linear model for other pathways that could also be employed in connection with the present invention.

EXAMPLE 11

Enrollment of Subject in a Clinical Trial Based on Predicted Activity

If a candidate drug is developed to, for instance, block the activity of a certain pathway that drives tumor growth, and this drug is going into clinical trial, then a proper selection of the subjects to enroll in such a trial is essential to prove potential effectiveness of the drug. In such a case, patients that do not have the respective pathway activated in their tumors should be excluded from the trial, as it is obvious that the drug cannot be effective if the pathway is not activated in the first place. Hence, a pathway model that can predict pathway activity, such as the (pseudo-)linear models described herein, can be used as a selection tool, to only select those patients that are predicted to have the respective pathway activated.

EXAMPLE 12

Selection of Subsequent Test(s) to be Performed

If a tumor is analyzed using different pathway models, and the models predict deregulation of a certain pathway, then this may guide the selection of subsequent tests to be performed. For instance, one may run a proximity ligation assay (PLA) to confirm the presence of the respective transcription complex (Söderberg O, 2006). Such a PLA can be designed to give a positive result if two key proteins in a TF complex have indeed bound together, for instance beta-catenin and TCF4 in the TF complex of the Wnt pathway.

Another example is that the pathway predicted to be deregulated is analyzed in more detail with respect to the signaling cascade. For instance, one may analyze key proteins in this pathway to determine whether there are mutations in the DNA regions encoding for their respective genes, or one may test for the abundance of these proteins to see whether they are higher or lower than normal. Such tests may indicate what the root cause is behind the deregulation of the pathway, and give insights on which available drugs could be used to reduce activity of the pathway.

These tests are selected to confirm the activity of the pathway as identified using the (pseudo-)linear models. However selection of companion diagnostic tests is also possible. After identification of the pathway using the model, for targeted therapy choice only those companion diagnostics tests need to be performed (the selection), which are applicable to the identified pathway.

EXAMPLE 13

Selection of Companion Diagnostics Tests

Similar to the previous example, if a tumor is analyzed and the pathway models predict deregulation of a certain pathway, and optionally a number of additional tests have been performed to investigate the cause of deregulation, then an oncologist may select a number of candidate drugs to treat the patient. However, treatment with such a drug may require a companion diagnostic test to be executed first, for instance to comply with clinical guidelines or to ensure reimbursement of the treatment costs, or because regulatory (FDA) it is required to perform the companion diagnostic test prior to giving the drug. An example of such a companion diagnostic test is the Her2 test for treatment of breast cancer patients with the drug Herceptin (Trastuzumab). Hence, the outcome of the pathway models can be used to select the candidate drugs and the respective companion diagnostic tests to be performed.

EXAMPLE 15

CDS Application

Figure 4:
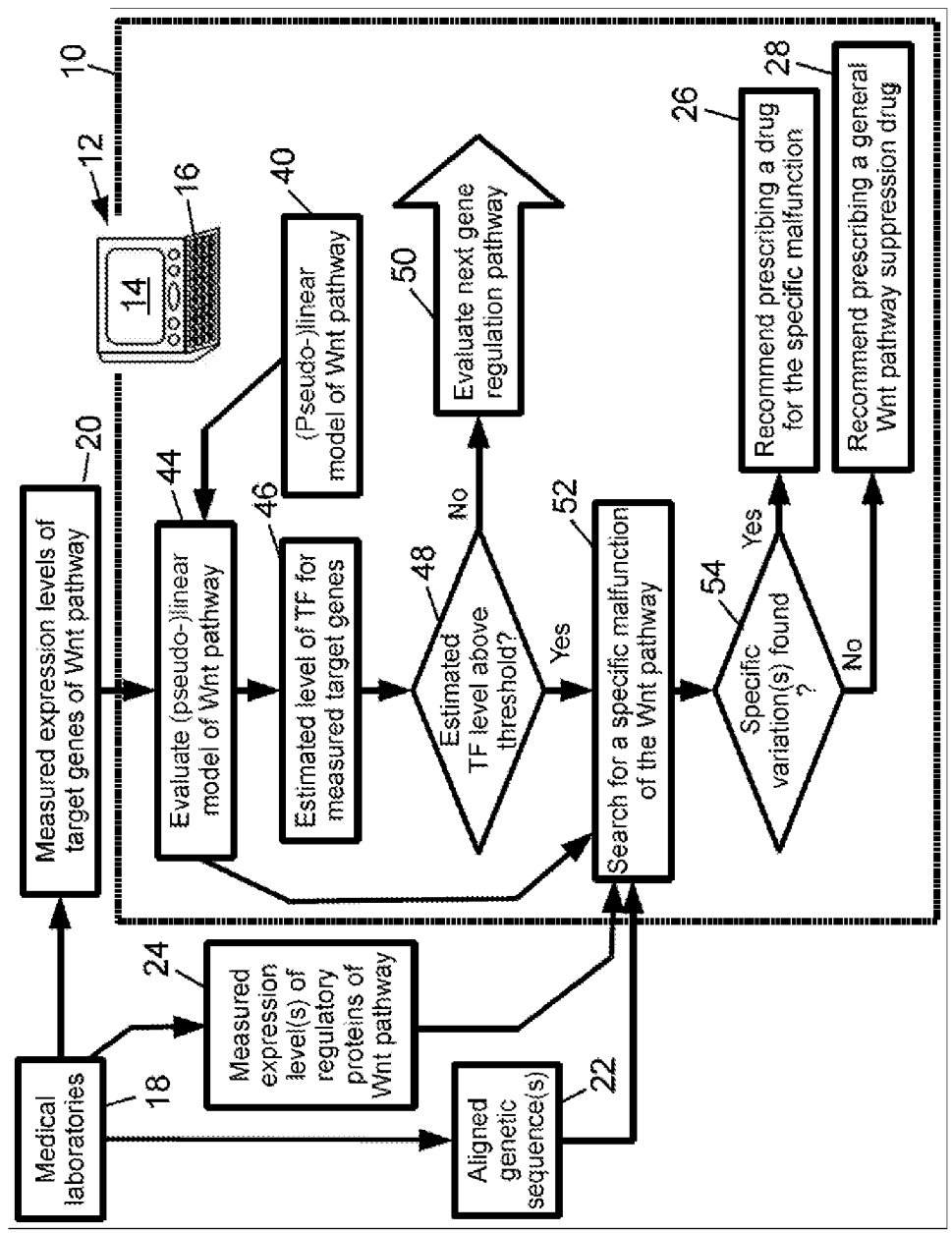

With reference to FIG. 4 (diagrammatically showing a clinical decision support (CDS) system configured to assess one or more cellular signaling pathways as disclosed herein (exemplary shown for Wnt pathway)), a clinical decision support (CDS) system 10 is implemented as a suitably configured computer 12. The computer 12 may be configured to operate as the CDS system 10 by executing suitable software, firmware, or other instructions stored on a non-transitory storage medium (not shown) such as a hard drive or other magnetic storage medium, an optical disk or other optical storage medium, a random access memory (RAM), read-only memory (ROM), flash memory, or other electronic storage medium, a network server, or so forth. While the illustrative CDS system 10 is embodied by the illustrative computer 12, more generally the CDS system may be embodied by a digital processing device or an apparatus comprising a digital processor configured to perform clinical decision support methods as set forth herein. For example, the digital processing device may be a handheld device (e.g., a personal data assistant or smartphone running a CDS application), a notebook computer, a desktop computer, a tablet computer or device, a remote network server, or so forth. The computer 12 or other digital processing device typically includes or is operatively connected with a display device 14 via which information including clinical decision support recommendations are displayed to medical personnel. The computer 12 or other digital processing device typically also includes or is operatively connected with one or more user input devices, such as an illustrative keyboard 16, or a mouse, trackball, trackpad, touch-sensitive screen (possibly integrated with the display device 14), or other pointer-based user input device, via which medical personnel can input information such as operational commands for controlling the CDS system 10, data for use by the CDS system 10, or so forth.

The CDS system 10 receives as input information pertaining to a medical subject (e.g., a hospital patient, or an outpatient being treated by an oncologist, physician, or other medical personnel, or a person undergoing cancer screening or some other medical diagnosis who is known or suspected to have a certain type of cancer such as colon cancer, breast cancer, or liver cancer, or so forth). The CDS system 10 applies various data analysis algorithms to this input information in order to generate clinical decision support recommendations that are presented to medical personnel via the display device 14 (or via a voice synthesizer or other device providing human-perceptible output). In some embodiments, these algorithms may include applying a clinical guideline to the patient. A clinical guideline is a stored set of standard or "canonical" treatment recommendations, typically constructed based on recommendations of a panel of medical experts and optionally formatted in the form of a clinical "flowchart" to facilitate navigating through the clinical guideline. In various embodiments the data processing algorithms of the CDS 10 may additionally or alternatively include various diagnostic or clinical test algorithms that are performed on input information to extract clinical decision recommendations, such as machine learning methods disclosed herein.

In the illustrative CDS systems disclosed herein (e.g., CDS system 10), the CDS data analysis algorithms include one or more diagnostic or clinical test algorithms that are performed on input genomic and/or proteomic information acquired by one or more medical laboratories 18. These laboratories may be variously located "on-site", that is, at the hospital or other location where the medical subject is undergoing medical examination and/or treatment, or "off-site", e.g. a specialized and centralized laboratory that receives (via mail or another delivery service) a sample of tissue and/or cells of the medical subject that has been extracted from the medical subject (e.g., a sample obtained from a breast lesion, or from a colon of a medical subject known or suspected of having colon cancer, or from a liver of a medical subject known or suspected of having liver cancer, or so forth, via a biopsy procedure or other sample extraction procedure). The tissue of which a sample is extracted may also be metastatic tissue, e.g. (suspected)

malignant tissue originating from the colon, breast, liver, or other organ that has spread outside of the colon, breast, liver, or other organ. The cells of which a sample is extracted may also be tumorous cells from hematologic malignancies (such as leukemia). In some cases, the cell sample may also be circulating tumor cells, that is, tumor cells that have entered the bloodstream and may be extracted as the extracted tissue sample using suitable isolation techniques. The extracted sample is processed by the laboratory to generate genomic or proteomic information. For example, the extracted sample may be processed using a microarray (also variously referred to in the art as a gene chip, DNA chip, biochip, or so forth) or by quantitative polymerase chain reaction (qPCR) processing to measure probative genomic or proteomic information such as expression levels of genes of interest, for example in the form of a level of messenger ribonucleic acid (mRNA) that is transcribed from the gene, or a level of a protein that is translated from the mRNA transcribed from the gene. As another example, the extracted sample may be processed by a gene sequencing laboratory to generate sequences for deoxyribonucleic acid (DNA), or to generate an RNA sequence, copy number variation, or so forth. Other contemplated measurement approaches include immunohistochemistry (IHC), cytology, fluorescence in situ hybridization (FISH), proximity ligation assay or so forth, performed on a pathology slide. Other information that can be generated by microarray processing, mass spectrometry, gene sequencing, or other laboratory techniques includes methylation information. Various combinations of such genomic and/or proteomic measurements may also be performed.

In some embodiments, the medical laboratories 18 perform a number of standardized data acquisitions on the extracted sample of the tissue and/or cells of the medical subject, so as to generate a large quantity of genomic and/or proteomic data. For example, the standardized data acquisition techniques may generate an (optionally aligned) DNA sequence for one or more chromosomes or chromosome portions, or for the entire genome of the tissue and/or cells. Applying a standard microarray can generate thousands or tens of thousands of data items such as expression levels for a large number of genes, various methylation data, and so forth. This plethora of genomic and/or proteomic data, or selected portions thereof, are input to the CDS system 10 to be processed so as to develop clinically useful information for formulating clinical decision support recommendations.

The disclosed CDS systems and related methods relate to processing of genomic and/or proteomic data to assess activity of various cellular signaling pathways. However, it is to be understood that the disclosed CDS systems (e.g., CDS system 10) may optionally further include diverse additional capabilities, such as generating clinical decision support recommendations in accordance with stored clinical guidelines based on various patient data such as vital sign monitoring data, patient history data, patient demographic data (e.g., gender, age, or so forth), patient medical imaging data, or so forth. Alternatively, in some embodiments the capabilities of the CDS system 10 may be limited to only performing genomic and/or proteomic data analyses to assess cellular signaling pathways as disclosed herein.

With continuing reference to exemplary FIG. 4, the CDS system 10 infers activity of a cellular signaling pathway in the tissue and/or cells of the medical subject based at least on, but not restricted to, expression levels of target genes of the cellular signaling pathway measured in the extracted sample, and determines whether the cellular signaling pathway is operating abnormally in the tissue and/or cells of the medical subject based on this inferred activity. Examples disclosed herein relate to the Wnt, ER, AR and HH pathways as illustrative cellular signaling pathways. These pathways are of interest in various areas of oncology because loss of regulation of the pathways can be a cause of proliferation of a cancer. There are about 10-15 relevant signaling pathways, and each cancer is driven by in principle one dominant pathway being deregulated. Without being limited to any particular theory of operation these pathways regulate cell proliferation, and consequentially a loss of regulation of these pathways in cancer cells can lead to the pathway being "always on" thus accelerating the proliferation of cancer cells, which in turn manifests as a growth, invasion or metastasis (spread) of the cancer.

Measurement of mRNA expression levels of genes that encode for regulatory proteins of the cellular signaling pathway, such as an intermediate protein that is part of a protein cascade forming the cellular signaling pathway, is an indirect measure of the regulatory protein expression level and may or may not correlate strongly with the actual regulatory protein expression level (much less with the overall activity of the cellular signaling pathway). The cellular signaling pathway directly regulates the transcription of the target genes—hence, the expression levels of mRNA transcribed from the target genes is a direct result of this regulatory activity. Hence, the CDS system 10 infers activity of the cellular signaling pathway (e.g., the Wnt, ER, AR and HH pathways) based at least on expression levels of target genes (mRNA or protein level as a surrogate measurement) of the cellular signaling pathway. This ensures that the CDS system 10 infers the activity of the pathway based on direct information provided by the measured expression levels of the target genes.

However, although, as disclosed herein, being effective for assessing activity of the overall pathways, the measured expression levels 20 of target genes of the pathways are not especially informative as to why the pathways are operating abnormally (if indeed that is the case). Said another way, the measured expression levels 20 of target genes of a pathway can indicate that the pathway is operating abnormally, but do not indicate what portion of the pathway is malfunctioning (e.g., lacks sufficient regulation) in order to cause the overall pathway to operate abnormally.

Accordingly, if the CDS system 10 detects abnormal activity of a particular pathway, the CDS system 10 then optionally makes use of other information provided by the medical laboratories 18 for the extracted sample, such as aligned genetic sequences 22 and/or measured expression level(s) for one or more regulatory genes of the pathway 24, or select the diagnostic test to be performed next in order to assess what portion of the pathway is malfunctioning. To maximize efficiency, in some embodiments this optional assessment of why the pathway is malfunctioning is performed only if the analysis of the measured expression levels 20 of target genes of the pathway indicates that the pathway is operating abnormally. In other embodiments, this assessment is integrated into the analysis of the cellular signaling pathway described herein.

In embodiments in which the CDS system 10 assesses what portion of the pathway is malfunctioning, and is successful in doing so, the additional information enables the CDS system 10 to recommend prescribing a drug targeting for the specific malfunction (recommendation 26 shown in FIG. 4). If no specific pathway malfunction is identified (either because the optional additional assessment is not performed or because that assessment fails to identify any particular portion of the pathway that is malfunctioning), then the CDS system 10 can provide a default recommendation 28 recommending the prescription of a general suppression drug for this particular pathway (assuming that the abnormal pathway activity is overly high activity).

EXAMPLE 16

A Kit and Analysis Tools to Measure Pathway Activity

The set of target genes which are found to best indicate specific pathway activity, based on microarray/RNA sequencing based investigation using the (pseudo-)linear model, can be translated into a multiplex quantitative PCR assay to be performed on a tissue or cell sample. To develop such an FDA-approved test for pathway activity, development of a standardized test kit is required, which needs to be clinically validated in clinical trials to obtain regulatory approval.

In general, it is to be understood that while examples pertaining to the Wnt, the ER, the AR and/or the HH pathway(s) are provided as illustrative examples, the approaches for cellular signaling pathway analysis disclosed herein are readily applied to other cellular signaling pathways besides these pathways, such as to intercellular signaling pathways with receptors in the cell membrane (cf above) and intracellular signaling pathways with receptors inside the cell (cf above). In addition: This application describes several preferred embodiments. Modifications and alterations may occur to others upon reading and understanding the preceding detailed description. It is intended that the application be construed as including all such modifications and alterations insofar as they come within the scope of the appended claims or the equivalents thereof.

LITERATURE de Sousa E Melo F, C. S. (2011). Methylation of cancer-stem-cell-associated Wnt target genes predicts poor prognosis in colorectal cancer patients. Cell Stem Cell., 476-485

Hatzis P, v. d. (2008). Genome-wide pattern of TCF7L2/TCF4 chromatin occupancy in colorectal cancer cells. Mol Cell Biol., 2732-2744

Nusse, R. (2012, May 1). Wnt target genes. Retrieved from The Wnt homepage: http://www.stanford.edu/group/nusselab/cgi-bin/wnt/target_genes Söderberg O, G. M. (2006). Direct observation of individual endogenous protein complexes in situ by proximity ligation. Nat Methods., 995-1000 van de Wetering M, S. E.-P.-F. (2002). The beta-catenin/TCF-4 complex imposes a crypt progenitor phenotype on colorectal cancer cells. Cell, 241-250

---

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11306360B2). An electronic copy of the "Sequence Listing" will also be available from the USPTO upon request and payment of the fee set forth in 37 CFR 1.19(b)(3).

---

The invention claimed is:

1. A method for correcting abnormal activity of a cellular signaling pathway in a subject diagnosed with cancer, wherein the cellular signaling pathway comprises a Wnt pathway, an ER pathway, an AR pathway, or an HH pathway, the method comprising:

obtaining, by using at least one of Polymerase Chain Reaction (PCR), a microarray technique, and RNA-sequencing, expression levels of three or more target genes of the cellular signaling pathway derived from a sample extracted from the subject;

determining, by a digital processing device using a mathematical model of the cellular signaling pathway, activity of the cellular signaling pathway in a tissue and/or cells of the subject based at least on the expression levels of the three or more target genes of the cellular signaling pathway measured in an extracted sample of the tissue and/or cells of the subject, wherein the determining comprises:

determining a level of a transcription factor (TF) element in the extracted sample of the tissue and/or cells of the subject, the TF element controlling transcription of the three or more target genes of the cellular signaling pathway, the determining being based at least in part on evaluating the mathematical model relating expression levels of the three or more target genes of the cellular signaling pathway to the level of the TF element, the model being based at least in part on one or more linear combination(s) of expression levels of the three or more target genes; and determining the activity of the cellular signaling pathway in the tissue and/or cells of the subject based on the determined level of the TF element in the extracted sample of the tissue and/or cells of the subject; and determining that the cellular signaling pathway is operating abnormally in the subject based on the determined activity of the cellular signaling pathway, wherein the determined abnormal operation of the cellular signaling pathway is overactive operation of the cellular signaling pathway; and selecting, based on the determined abnormal operation of the cellular signaling pathway, a specific treatment configured to remedy the determined abnormal operation of the cellular signaling pathway, wherein the specific treatment is a signaling pathway inhibitor configured to inhibit the operation of the cellular signaling pathway; and administering, in response to the determined abnormal operation of the cellular signaling pathway and the selection of the specific treatment configured to remedy the determined abnormal operation of the cellular signaling pathway, the signaling pathway inhibitor;
wherein the signaling pathway inhibitor is a Wnt pathway inhibitor when the determined abnormal operation of the cellular signaling pathway is abnormal operation of the Wnt pathway, wherein the signaling pathway inhibitor is an ER pathway inhibitor when the determined abnormal operation of the cellular signaling pathway is abnormal operation of the ER pathway, wherein the signaling pathway inhibitor is an AR pathway inhibitor when the determined abnormal operation of the cellular signaling pathway is abnormal operation of the AR pathway, and wherein the signaling pathway inhibitor is an HH pathway inhibitor when the determined abnormal operation of the cellular signaling pathway is abnormal operation of the HH pathway.

2. The method of claim 1, wherein for each of the three or more target genes one or more expression level(s) measured in the extracted sample of the tissue and/or cells of the subject is provided, and wherein the one or more linear combination(s) comprises a linear combination of all expression levels of the one or more expression level(s) provided for the three or more target genes.

3. The method of claim 1, wherein for each of the three or more target genes one or more expression level(s) measured in the extracted sample of the tissue and/or cells of the subject is provided, and wherein the one or more linear combination(s) comprise a linear combination including for each of the three or more target genes a weighted term, each weighted term being based on only one expression level of the one or more expression level(s) provided for the respective target gene.

4. The method of claim 1, wherein for each of the three or more target genes one or more expression level(s) measured in the extracted sample of the tissue and/or cells of the subject is provided, wherein the one or more linear combination(s) comprises for each of the three or more target genes a first linear combination of all expression levels of the one or more expression level(s) provided for the respective target gene, and wherein the model is further based at least in part on a further linear combination including for each of the three or more target genes a weighted term, each weighted term being based on the first linear combination for the respective target gene.

5. The method of claim 1, wherein the determining comprises:
determining activity of a Wnt pathway in the tissue and/or cells of the subject based at least on expression levels of three or more target genes of the Wnt pathway measured in the extracted sample of the tissue and/or cells of the subject selected from the group comprising: KIAA1199, AXIN2, RNF43, TBX3, TDGF1, SOX9, ASCL2, IL8, SP5, ZNRF3, KLF6, CCND1, DEFA6 and FZD7.

6. The method of claim 1, wherein the determining comprises:
determining activity of an ER pathway in the tissue and/or cells of the subject based at least on expression levels of three or more target genes of the ER pathway measured in the extracted sample of the tissue and/or cells of the subject selected from the group comprising: CDH26, SGK3, PGR, GREB1, CA12, XBPI, CELSR2, WISP2, DSCAM, ERBB2, CTSD, TFF1 and NRIP1.

7. The method of claim 1, wherein the determining comprises: determining activity of an HH pathway in the tissue and/or cells of the subject based at least on expression levels of three or more target genes of the HH pathway measured in the extracted sample of the tissue and/or cells of the subject selected from the group comprising: GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN and CTSL1.

8. The method of claim 1, wherein the determining comprises:
determining activity of an AR pathway in the tissue and/or cells of the subject based at least on expression levels of three or more target genes of the AR pathway measured in the extracted sample of the tissue and/or cells of the subject selected from the group comprising: KLK2, PMEPA1, TMPRSS2, NKX3 1, ABCC4, KLK3, FKBPS, ELL2, UGT2B15, DHCR24, PPAP2A, NDRG1, LRIG1, CREB3L4, LCP1, GUCY1A3, AR and EAF2.

9. The method of claim 5, wherein the determining is further based on expression levels of at least one target gene of the Wnt pathway measured in the extracted sample of the tissue and/or cells of the subject selected from the group comprising: NKD1, OAT, FAT1, LEF1, GLUL, REG1B, TCF7L2, COL18A1, BMP7, SLC1A2, ADRA2C, PPARG, DKK1, HNF1A and LECT2.

10. The method of claim 6, wherein the determining is further based on expression levels of at least one target gene of the ER pathway measured in the extracted sample of the tissue and/or cells of the subject selected from the group comprising: AP1B1, ATPSJ, COL18A1, COX7A2L, EBAG9, ESR1, HSPB1, IGFBP4, KRT19, MYC, NDUFV3, PISD, PRDM15, PTMA, RARA, SOD1 and TRIM25.

11. The method of claim 7, wherein the determining is further based on expression levels of at least one target gene of the HE pathway measured in the extracted sample of the tissue and/or cells of the subject selected from the group comprising: BCL2, FOXA2, FOXF1, H19, HHIP, IL1R2, JAG2, JUP, MIF, MYLK, NKX2.2, NKX2.8, PITRM1 and TOM1.

12. The method of claim 8, wherein the determining is further based on expression levels of at least one target gene of the AR pathway measured in the extracted sample of the tissue and/or cells of the subject selected from the group comprising: APP, NTS, PLAU, CDKN1A, DRG1, FGF8, IGF1, PRKACB, PTPN1, SGK1 and TACC2.

13. The method of claim 1, further comprising:
prescribing a drug for the subject configured to remedy the determined abnormal operation of the cellular signaling pathway.

14. The method of claim 1, wherein the method is used in at least one of the following activities:
diagnosis based on the determined activity of the cellular signaling pathway in the tissue and/or cells of the subject;
prognosis based on the determined activity of the cellular signaling pathway in the tissue and/or cells of the subject;
drug prescription based on the determined activity of the cellular signaling pathway in the tissue and/or cells of the subject;
prediction of drug efficacy based on the determined activity of the cellular signaling pathway in the tissue and/or cells of the subject;
prediction of adverse effects based on the determined activity of the cellular signaling pathway in the tissue and/or cells of the subject;
monitoring of drug efficacy;
drug development;
assay development;

pathway research;
cancer staging;
enrollment of the subject in a clinical trial based on the determined activity of the cellular signaling pathway in the tissue and/or cells of the subject;
selection of subsequent test to be performed, and
selection of companion diagnostics tests.

15. The method of claim 1, further comprising:
determining activity of a Wnt pathway in tissue and/or cells of a subject based at least on expression levels of two, three or more target genes of a set of target genes of the Wnt pathway measured in an extracted sample of the tissue and/or cells of the subject,
and/or
determining activity of an ER pathway in tissue and/or cells of a subject based at least on expression levels of two, three or more target genes of a set of target genes of the ER pathway measured in an extracted sample of the tissue and/or cells of the subject,
and/or
determining activity of a HH pathway in tissue and/or cells of a subject based at least on expression levels of two, three or more target genes of a set of target genes of the HH pathway measured in an extracted sample of the tissue and/or cells of the subject,
and/or
determining activity of an AR pathway in tissue and/or cells of a subject based at least on expression levels of two, three or more target genes of a set of target genes of the AR pathway measured in an extracted sample of the tissue and/or cells of the subject.

16. The method of claim 15, wherein
the set of target genes of the Wnt pathway includes at least nine target genes selected from the group comprising: KIAA1199, AXIN2, RNF43, TBX3, TDGF1, SOX9, ASCL2, IL8, SP5, ZNRF3, KLF6, CCND1, DEFA6 and FZD7,
and/or
the set of target genes of the ER pathway includes at least nine target genes selected from the group comprising: CDH26, SGK3, PGR, GREB1, CA12, XBP1, CELSR2, WISP2, DSCAM, ERBB2, CTSD, TFF1 and NRIP1,
and/or
the set of target genes of the HH pathway includes at least nine target genes selected from the group comprising: GLI1, PTCH1, PTCH2, IGFBP6, SPP1, CCND2, FST, FOXL1, CFLAR, TSC22D1, RAB34, S100A9, S100A7, MYCN, FOXM1, GLI3, TCEA2, FYN and CTSL1,
and/or
the set of target genes of the AR pathway includes at least nine target genes selected from the group comprising: KLK2, PMEPA1, TMPRSS2, NKX3 1, ABCC4, KLK3, FKBP5, ELL2, UGT2B15, DHCR24, PPAP2A, NDRG1, LRIG1, CREB3L4, LCP1, GUCY1A3, AR and EAF2.

17. The method of claim 16, wherein
The set of target genes of the Wnt pathway further includes at least one target gene selected from the group comprising: NKD1, OAT, FAT1, LEF1, GLUL, REG1B, TCF7L2, COL18A1, BMP7, SLC1A2, ADRA2C, PPARG, DKK1, HNF1A, and LECT2,
and/or
the set of target genes of the ER pathway further includes at least one target gene selected from the group comprising: AP1B1, ATPSJ, COL18A1, COX7A2L, EBAG9, ESR1, HSPB1, IGFBP4, KRT19, MYC, NDUFV3, PISD, PRDM15, PTMA, RARA, SOD1 and TRIM25,
and/or
the set of target genes of the HH pathway further includes at least one target gene selected from the group comprising: BCL2, FOXA2, FOXF1, H19, HHIP, IL1R2, JAG2, JUP, MIF, MYLK, NKX2.2, NKX2.8, PITRM1 and TOM1,
and/or
the set of target genes of the AR pathway further includes at least one target gene selected from the group comprising: APP, NTS, PLAU, CDKN1A, DRG1, FGF8, IGF1, PRKACB, PTPN1, SGK1 and TACC2.

18. The method of claim 1, wherein the obtaining of the expression levels of the three or more target genes includes measuring the expression levels of the three or more target genes.

19. The method of claim 1,
wherein the target genes are mRNA direct target genes,
wherein the method further comprises calibrating the mathematical model, and
wherein the method further comprises:
constructing a network between the expression levels of the three or more mRNA direct target genes and the activity of the cellular signaling pathway, and
training the network by:
determining the level of the TF element in the extracted sample of the tissue and/or cells of the subject, the TF element controlling transcription of the three or more mRNA direct target genes of the cellular signaling pathway;
determining the activity of the cellular signaling pathway in the tissue and/or cells of the subject based on the determined level of the TF element in the extracted sample of the tissue and/or cells of the subject; and
measuring the nodes representing corresponding probe set nodes of the corresponding three or more mRNA direct target genes.

20. A method for correcting abnormal activity of a cellular signaling pathway in a subject diagnosed with cancer, wherein the cellular signaling pathway comprises a Wnt pathway, an ER pathway, an AR pathway, or an HH pathway, the method comprising:
obtaining, by using at least one of Polymerase Chain Reaction (PCR), a microarray technique, and RNA-sequencing, expression levels of three or more target genes of the cellular signaling pathway derived from a sample extracted from the subject;
determining, by a digital processing device using a mathematical model of the cellular signaling pathway, activity of the cellular signaling pathway in a tissue and/or cells of the subject based at least on the expression levels of the three or more target genes of the cellular signaling pathway measured in an extracted sample of the tissue and/or cells of the subject, wherein the determining comprises/:
determining a level of a transcription factor (TF) element in the extracted sample of the tissue and/or cells of the subject, the TF element controlling transcription of the three or more target genes of the cellular signaling pathway, the determining being based at least in part on evaluating the mathematical model relating expression levels of the three or more target genes of the cellular signaling pathway to the level of the TF element, the model being based at least in part on one or more linear combination(s) of expression levels of the three or more target genes; and determining the activity of the cellular signaling pathway in the tissue and/or cells of the subject based on the determined level of the TF element in the extracted sample of the tissue and/or cells of the subject; and determining that the cellular signaling pathway is operating abnormally in the subject based on the determined activity of the cellular signaling pathway, wherein the determined abnormal operation of the cellular signaling pathway is inactive or underactive operation of the cellular signaling pathway; and selecting, based on the determined abnormal operation of the cellular signaling pathway, a specific treatment configured to remedy the determined abnormal operation of the cellular signaling pathway, wherein the specific treatment is a signaling pathway upregulator configured to upregulate the operation of the cellular signaling pathway; and administering, in response to the determined abnormal operation of the cellular signaling pathway and the selection of the specific treatment configured to remedy the determined abnormal operation of the cellular signaling pathway, the signaling pathway upregulator;

wherein the signaling pathway upregulator is a Wnt pathway upregulator when the determined abnormal operation of the cellular signaling pathway is abnormal operation of the Wnt pathway, wherein the signaling pathway upregulator is an ER pathway upregulator when the determined abnormal operation of the cellular signaling pathway is abnormal operation of the ER pathway, wherein the signaling pathway upregulator is an AR pathway upregulator when the determined abnormal operation of the cellular signaling pathway is abnormal operation of the AR pathway, and wherein the signaling pathway upregulator is an HH pathway upregulator when the determined abnormal operation of the cellular signaling pathway is abnormal operation of the HH pathway.

21. A method for treating a subject diagnosed with cancer, comprising:

selecting, based on a determined abnormal operation of a cellular signaling pathway, a specific treatment configured to remedy the determined abnormal operation of the cellular signaling pathway, wherein the specific treatment is a signaling pathway inhibitor configured to inhibit the operation of the cellular signaling pathway, and wherein the cellular signaling pathway comprises a Wnt pathway, an ER pathway, an AR pathway, or an HH pathway, wherein the abnormal operation of a cellular signaling pathway is determined by:

obtaining, by using at least one of Polymerase Chain Reaction (PCR), a microarray technique, and RNA-sequencing, expression levels of three or more target genes of the cellular signaling pathway derived from a sample extracted from the subject;

determining, by a digital processing device using a mathematical model of the cellular signaling pathway, activity of the cellular signaling pathway in a tissue and/or cells of the subject based at least on the expression levels of the three or more target genes of the cellular signaling pathway measured in an extracted sample of the tissue and/or cells of the subject, wherein the determining comprises:

determining a level of a transcription factor (TF) element in the extracted sample of the tissue and/or cells of the subject, the TF element controlling transcription of the three or more target genes of the cellular signaling pathway, the determining being based at least in part on evaluating the mathematical model relating expression levels of the three or more target genes of the cellular signaling pathway to the level of the TF element, the model being based at least in part on one or more linear combination(s) of expression levels of the three or more target genes; and determining the activity of the cellular signaling pathway in the tissue and/or cells of the subject based on the determined level of the TF element in the extracted sample of the tissue and/or cells of the subject; and determining that the cellular signaling pathway is operating abnormally in the subject based on the determined activity of the cellular signaling pathway, wherein the determined abnormal operation of the cellular signaling pathway is overactive operation of the cellular signaling pathway; and administering the signaling pathway inhibitor;

wherein the signaling pathway inhibitor is a Wnt pathway inhibitor when the determined abnormal operation of the cellular signaling pathway is abnormal operation of the Wnt pathway, wherein the signaling pathway inhibitor is an ER pathway inhibitor when the determined abnormal operation of the cellular signaling pathway is abnormal operation of the ER pathway, wherein the signaling pathway inhibitor is an AR pathway inhibitor when the determined abnormal operation of the cellular signaling pathway is abnormal operation of the AR pathway, and wherein the signaling pathway inhibitor is an HH pathway inhibitor when the determined abnormal operation of the cellular signaling pathway is abnormal operation of the HH pathway.

* * * * *